(12) United States Patent
Clauda et al.

(10) Patent No.: US 11,998,230 B2
(45) Date of Patent: Jun. 4, 2024

(54) END EFFECTOR CONTROL AND CALIBRATION

(71) Applicant: Cilag GmbH International, Zug (CH)

(72) Inventors: Phillip H. Clauda, Cincinnati, OH (US); Cameron Nott, Fairfield, OH (US); John F. Cummings, Madeira, OH (US); David J. Cagle, San Francisco, CA (US); Daniel J. Ulrich, Hamilton, OH (US)

(73) Assignee: Cilag GmbH International, Zug (CH)

( * ) Notice: Subject to any disclaimer, the term of this patent is extended or adjusted under 35 U.S.C. 154(b) by 98 days.

(21) Appl. No.: 17/665,163

(22) Filed: Feb. 4, 2022

(65) Prior Publication Data

US 2022/0226014 A1 Jul. 21, 2022

Related U.S. Application Data

(63) Continuation of application No. 15/363,244, filed on Nov. 29, 2016, now Pat. No. 11,266,430.

(51) Int. Cl.
*A61B 17/32* (2006.01)
*A61B 8/14* (2006.01)
(Continued)

(52) U.S. Cl.
CPC .. *A61B 17/320092* (2013.01); *A61B 17/2909* (2013.01); *A61B 17/295* (2013.01);
(Continued)

(58) Field of Classification Search
CPC ............ A61B 18/1206; A61B 18/1445; A61B 18/1447; A61B 2018/00601;
(Continued)

(56) References Cited

U.S. PATENT DOCUMENTS 969,528 A 9/1910 Disbrow
1,570,025 A 1/1926 Young
(Continued)

FOREIGN PATENT DOCUMENTS

CA 2535467 A1 4/1993
CN 2460047 Y 11/2001
(Continued)

OTHER PUBLICATIONS

"ATM-MPLS Network Interworking Version 2.0, af-aic-0178.001" ATM Standard, The ATM Forum Technical Committee, published Aug. 2003.
(Continued)

*Primary Examiner* — Tigist S Demie

(57) ABSTRACT

Methods and apparatus for end effector control and calibration are described. The method may include detecting a signal in response to movement of a first tube relative to a second tube, the first tube driving movement of a clamp arm of the end effector. The method may further include determining a clamp arm position of the end effector relative to a ultrasonic blade of the end effector based on the signal. The method may also include adjusting a power output to the ultrasonic blade of the end effector based on the clamp arm position.

21 Claims, 34 Drawing Sheets

(51) Int. Cl.
*A61B 17/29* (2006.01)
*A61B 17/295* (2006.01)
*A61B 18/14* (2006.01)
*A61B 17/00* (2006.01)
*A61B 17/28* (2006.01)
*A61B 18/00* (2006.01)

(52) U.S. Cl.
CPC .......... *A61B 17/32* (2013.01); *A61B 18/1445* (2013.01); *A61B 2017/00026* (2013.01); *A61B 2017/00039* (2013.01); *A61B 2017/00128* (2013.01); *A61B 2017/00725* (2013.01); *A61B 2017/00977* (2013.01); *A61B 2017/2808* (2013.01); *A61B 2017/2925* (2013.01); *A61B 2017/320094* (2017.08); *A61B 2017/320095* (2017.08); *A61B 2018/00595* (2013.01); *A61B 2018/00607* (2013.01); *A61B 2018/00642* (2013.01); *A61B 2018/00666* (2013.01); *A61B 2018/00702* (2013.01); *A61B 2018/00875* (2013.01); *A61B 2018/00994* (2013.01)

(58) Field of Classification Search
CPC ........... A61B 2018/00702; A61B 2018/00714; A61B 2018/0072; A61B 2018/00761; A61B 2018/00767; A61B 2018/00875; A61B 2018/1213; A61B 2018/126; A61B 2018/1266; A61B 2018/142; A61B 2018/1452; A61F 2240/001; A61F 2/82
See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,244,371 A | 1/1981 | Farin |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,353,371 A | 10/1982 | Cosman |
| 4,409,981 A | 10/1983 | Lundberg |
| 4,445,063 A | 4/1984 | Smith |
| 4,461,304 A | 7/1984 | Kuperstein |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,608,981 A | 9/1986 | Rothfuss et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,739,759 A | 4/1988 | Rexroth et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |

(56) References Cited

U.S. PATENT DOCUMENTS

| | | |
|---|---|---|
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | Mcgurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,926,860 A | 5/1990 | Stice et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,003,693 A | 4/1991 | Atkinson et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,052,145 A | 10/1991 | Wang |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,517 A | 3/1993 | Zieve et al. |
| 5,190,518 A | 3/1993 | Takasu |
| 5,190,541 A | 3/1993 | Abele et al. |
| 5,196,007 A | 3/1993 | Ellman et al. |
| 5,203,380 A | 4/1993 | Chikama |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A | 9/1993 | DeLonzor |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,334,183 A | 8/1994 | Wuchinich |
| 5,339,723 A | 8/1994 | Huitema |
| 5,342,356 A | 8/1994 | Ellman et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,917 A | 1/1995 | Desai et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |

(56) References Cited

U.S. PATENT DOCUMENTS

| | | |
|---|---|---|
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,053 A | 9/1995 | Garrido |
| 5,451,161 A | 9/1995 | Sharp |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,536,267 A | 7/1996 | Edwards et al. |
| 5,540,681 A | 7/1996 | Strul et al. |
| 5,540,684 A | 7/1996 | Hassler, Jr. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,608 A | 5/1997 | Cuny et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,638,827 A | 6/1997 | Palmer et al. |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,042 A | 12/1997 | Boiarski et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,723,970 A | 3/1998 | Bell |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,759,183 A | 6/1998 | VanDusseldorp |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |

(56) References Cited

U.S. PATENT DOCUMENTS

| | | |
|---|---|---|
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,854,590 A | 12/1998 | Dalstein |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,987,344 A | 11/1999 | West |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,102,909 A | 8/2000 | Chen et al. |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| H1904 H | 10/2000 | Yates et al. |
| 6,126,629 A | 10/2000 | Perkins |
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |

(56) References Cited

U.S. PATENT DOCUMENTS

| | | |
|---|---|---|
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,383 B1 | 3/2001 | Hermann |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,232,899 B1 | 5/2001 | Craven |
| 6,233,476 B1 | 5/2001 | Strommer et al. |
| 6,238,366 B1 | 5/2001 | Savage et al. |
| 6,238,384 B1 | 5/2001 | Peer |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,261,286 B1 | 7/2001 | Goble et al. |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,184 B1 | 6/2002 | Bohme et al. |
| 6,405,733 B1 | 6/2002 | Fogarty et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,417,969 B1 | 7/2002 | DeLuca et al. |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,436,129 B1 | 8/2002 | Sharkey et al. |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,459,363 B1 | 10/2002 | Walker et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,270 B1 | 10/2002 | Hovda et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,558,380 B2 | 5/2003 | Lingenfelder et al. |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |

(56) References Cited

U.S. PATENT DOCUMENTS

| | | |
|---|---|---|
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |
| 6,602,252 B2 | 8/2003 | Mollenauer |
| 6,602,262 B2 | 8/2003 | Griego et al. |
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,632,221 B1 | 10/2003 | Edwards et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,730,080 B2 | 5/2004 | Harano et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |

(56) References Cited

U.S. PATENT DOCUMENTS

| | | |
|---|---|---|
| 6,981,628 B2 | 1/2006 | Wales |
| 6,984,220 B2 | 1/2006 | Wuchinich |
| 6,984,231 B2 | 1/2006 | Goble et al. |
| 6,988,295 B2 | 1/2006 | Tillim |
| 6,988,649 B2 | 1/2006 | Shelton, IV et al. |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,637 B2 | 8/2006 | Danitz et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,447 B2 | 6/2007 | Uchida et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |

(56) References Cited

U.S. PATENT DOCUMENTS

| | | |
|---|---|---|
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,507,239 B2 | 3/2009 | Shadduck |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,525,309 B2 | 4/2009 | Sherman et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,696,441 B2 | 4/2010 | Kataoka |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,708,768 B2 | 5/2010 | Danek et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |

(56) References Cited

U.S. PATENT DOCUMENTS

| | | |
|---|---|---|
| 7,726,537 B2 | 6/2010 | Olson et al. |
| 7,727,177 B2 | 6/2010 | Bayat |
| 7,731,717 B2 | 6/2010 | Odom et al. |
| 7,738,969 B2 | 6/2010 | Bleich |
| 7,740,594 B2 | 6/2010 | Hibner |
| 7,744,615 B2 | 6/2010 | Couture |
| 7,749,240 B2 | 7/2010 | Takahashi et al. |
| 7,751,115 B2 | 7/2010 | Song |
| 7,753,245 B2 | 7/2010 | Boudreaux et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,794,475 B2 | 9/2010 | Hess et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,027 B2 | 9/2010 | Hafner |
| 7,799,045 B2 | 9/2010 | Masuda |
| 7,803,151 B2 | 9/2010 | Whitman |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,238 B2 | 10/2010 | Cao |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,862,561 B2 | 1/2011 | Swanson et al. |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,029 B2 | 2/2011 | Jimenez |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Likura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,954,682 B2 | 6/2011 | Giordano et al. |
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |
| 7,972,329 B2 | 7/2011 | Refior et al. |
| 7,975,895 B2 | 7/2011 | Milliman |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,002,770 B2 | 8/2011 | Swanson et al. |
| 8,020,743 B2 | 9/2011 | Shelton, IV |
| 8,025,672 B2 | 9/2011 | Novak et al. |
| 8,028,885 B2 | 10/2011 | Smith et al. |
| 8,033,173 B2 | 10/2011 | Ehlert et al. |
| 8,034,049 B2 | 10/2011 | Odom et al. |
| 8,038,693 B2 | 10/2011 | Allen |
| 8,048,070 B2 | 11/2011 | O'Brien et al. |
| 8,048,074 B2 | 11/2011 | Masuda |
| 8,052,672 B2 | 11/2011 | Laufer et al. |
| 8,055,208 B2 | 11/2011 | Lilla et al. |
| 8,056,720 B2 | 11/2011 | Hawkes |
| 8,056,787 B2 | 11/2011 | Boudreaux et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,118,276 B2 | 2/2012 | Sanders et al. |

(56) References Cited

U.S. PATENT DOCUMENTS

| | | |
|---|---|---|
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,170,717 B2 | 5/2012 | Sutherland et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,211,100 B2 | 7/2012 | Podhajsky et al. |
| 8,216,223 B2 | 7/2012 | Wham et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,221,418 B2 | 7/2012 | Prakash et al. |
| 8,226,580 B2 | 7/2012 | Govari et al. |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,308,721 B2 | 11/2012 | Shibata et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,764 B2 | 12/2012 | Francischelli et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,144 B2 | 1/2013 | Whitman et al. |
| 8,357,149 B2 | 1/2013 | Govari et al. |
| 8,357,158 B2 | 1/2013 | McKenna et al. |
| 8,360,299 B2 | 1/2013 | Zemlok et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,393,514 B2 | 3/2013 | Shelton, IV et al. |
| 8,394,115 B2 | 3/2013 | Houser et al. |
| 8,397,971 B2 | 3/2013 | Yates et al. |
| 8,398,394 B2 | 3/2013 | Sauter et al. |
| 8,398,674 B2 | 3/2013 | Prestel |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |

(56) References Cited

U.S. PATENT DOCUMENTS

| | | |
|---|---|---|
| 8,425,410 B2 | 4/2013 | Murray et al. |
| 8,425,545 B2 | 4/2013 | Smith et al. |
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,437,832 B2 | 5/2013 | Govari et al. |
| 8,439,912 B2 | 5/2013 | Cunningham et al. |
| 8,439,939 B2 | 5/2013 | Deville et al. |
| 8,444,036 B2 | 5/2013 | Shelton, IV |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,471,685 B2 | 6/2013 | Shingai |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,337 B2 | 8/2013 | Francischelli et al. |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,517,239 B2 | 8/2013 | Scheib et al. |
| 8,518,067 B2 | 8/2013 | Masuda et al. |
| 8,521,331 B2 | 8/2013 | Itkowitz |
| 8,523,043 B2 | 9/2013 | Ullrich et al. |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,308 B2 | 9/2013 | Govari et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,556,929 B2 | 10/2013 | Harper et al. |
| 8,561,870 B2 | 10/2013 | Baxter, III et al. |
| 8,562,592 B2 | 10/2013 | Conlon et al. |
| 8,562,598 B2 | 10/2013 | Falkenstein et al. |
| 8,562,600 B2 | 10/2013 | Kirkpatrick et al. |
| 8,562,604 B2 | 10/2013 | Nishimura |
| 8,568,390 B2 | 10/2013 | Mueller |
| 8,568,397 B2 | 10/2013 | Horner et al. |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,585,727 B2 | 11/2013 | Polo |
| 8,588,371 B2 | 11/2013 | Ogawa et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,596,513 B2 | 12/2013 | Olson et al. |
| 8,597,193 B2 | 12/2013 | Grunwald et al. |
| 8,597,287 B2 | 12/2013 | Benamou et al. |
| 8,602,031 B2 | 12/2013 | Reis et al. |
| 8,602,288 B2 | 12/2013 | Shelton, IV et al. |
| 8,603,085 B2 | 12/2013 | Jimenez |
| 8,603,089 B2 | 12/2013 | Viola |
| 8,608,044 B2 | 12/2013 | Hueil et al. |
| 8,608,045 B2 | 12/2013 | Smith et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,617,152 B2 | 12/2013 | Werneth et al. |
| 8,617,194 B2 | 12/2013 | Beaupre |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,040 B2 | 1/2014 | Artsyukhovich et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,657,489 B2 | 2/2014 | Ladurner et al. |
| 8,659,208 B1 | 2/2014 | Rose et al. |
| 8,663,214 B2 | 3/2014 | Weinberg et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,696,666 B2 | 4/2014 | Sanai et al. |
| 8,696,917 B2 | 4/2014 | Petisce et al. |
| 8,702,609 B2 | 4/2014 | Hadjicostis |
| 8,702,702 B1 | 4/2014 | Edwards et al. |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,008 B2 | 4/2014 | Willis et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,733,613 B2 | 5/2014 | Huitema et al. |
| 8,733,614 B2 | 5/2014 | Ross et al. |
| 8,734,443 B2 | 5/2014 | Hixson et al. |

(56) References Cited

U.S. PATENT DOCUMENTS

| | | |
|---|---|---|
| 8,738,110 B2 | 5/2014 | Tabada et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,758,391 B2 | 6/2014 | Swayze et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,275 B2 | 8/2014 | Hafner |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,807,414 B2 | 8/2014 | Ross et al. |
| 8,808,204 B2 | 8/2014 | Irisawa et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,831,779 B2 | 9/2014 | Ortmaier et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,874,220 B2 | 10/2014 | Draghici et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,945,126 B2 | 2/2015 | Garrison et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,974,932 B2 | 3/2015 | McGahan et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,370 B2 | 4/2015 | Reschke et al. |
| 9,017,372 B2 | 4/2015 | Artale et al. |
| 9,023,035 B2 | 5/2015 | Allen, IV et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,481 B2 | 5/2015 | Behnke, II |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,691 B2 | 5/2015 | Moua et al. |
| 9,039,692 B2 | 5/2015 | Behnke, II et al. |
| 9,039,695 B2 | 5/2015 | Giordano et al. |
| 9,039,696 B2 | 5/2015 | Assmus et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |
| 9,044,230 B2 | 6/2015 | Morgan et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,083 B2 | 6/2015 | Yates et al. |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |

(56) References Cited

U.S. PATENT DOCUMENTS

| | | |
|---|---|---|
| 9,060,775 B2 | 6/2015 | Wiener et al. |
| 9,060,776 B2 | 6/2015 | Yates et al. |
| 9,060,778 B2 | 6/2015 | Condie et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,072,538 B2 | 7/2015 | Suzuki et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,333 B2 | 8/2015 | Konesky et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,186,796 B2 | 11/2015 | Ogawa |
| 9,192,380 B2 | 11/2015 | (Tarinelli) Racenet et al. |
| 9,192,421 B2 | 11/2015 | Garrison |
| 9,192,428 B2 | 11/2015 | Houser et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,718 B2 | 12/2015 | Marczyk et al. |
| 9,198,776 B2 | 12/2015 | Young |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,051 B2 | 12/2015 | Fischer et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, II et al. |
| 9,265,926 B2 | 2/2016 | Strobl et al. |
| 9,265,973 B2 | 2/2016 | Akagane |
| 9,266,310 B2 | 2/2016 | Krogdahl et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,283,054 B2 | 3/2016 | Morgan et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,305,497 B2 | 4/2016 | Seo et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,261 B2 | 4/2016 | Bales, Jr. et al. |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,767 B2 | 5/2016 | Koch, Jr. et al. |
| 9,326,787 B2 | 5/2016 | Sanai et al. |
| 9,326,788 B2 | 5/2016 | Batross et al. |
| 9,332,987 B2 | 5/2016 | Leimbach et al. |
| 9,333,025 B2 | 5/2016 | Monson et al. |
| 9,333,034 B2 | 5/2016 | Hancock |
| 9,339,289 B2 | 5/2016 | Robertson |
| 9,339,323 B2 | 5/2016 | Eder et al. |
| 9,339,326 B2 | 5/2016 | McCullagh et al. |
| 9,345,481 B2 | 5/2016 | Hall et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,726 B2 | 5/2016 | Leimbach et al. |
| 9,351,727 B2 | 5/2016 | Leimbach et al. |
| 9,351,754 B2 | 5/2016 | Vakharia et al. |
| 9,352,173 B2 | 5/2016 | Yamada et al. |
| 9,358,003 B2 | 6/2016 | Hall et al. |
| 9,358,065 B2 | 6/2016 | Ladtkow et al. |
| 9,364,171 B2 | 6/2016 | Harris et al. |
| 9,364,230 B2 | 6/2016 | Shelton, IV et al. |
| 9,364,279 B2 | 6/2016 | Houser et al. |
| 9,370,364 B2 | 6/2016 | Smith et al. |
| 9,370,400 B2 | 6/2016 | Parihar |
| 9,370,611 B2 | 6/2016 | Ross et al. |
| 9,375,206 B2 | 6/2016 | Vidal et al. |
| 9,375,230 B2 | 6/2016 | Ross et al. |
| 9,375,232 B2 | 6/2016 | Hunt et al. |
| 9,375,256 B2 | 6/2016 | Cunningham et al. |
| 9,375,264 B2 | 6/2016 | Horner et al. |
| 9,375,267 B2 | 6/2016 | Kerr et al. |
| 9,385,831 B2 | 7/2016 | Marr et al. |
| 9,386,983 B2 | 7/2016 | Swensgard et al. |
| 9,393,037 B2 | 7/2016 | Olson et al. |
| 9,393,070 B2 | 7/2016 | Gelfand et al. |
| 9,398,911 B2 | 7/2016 | Auld |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,014 B2 | 8/2016 | Ingmanson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane |
| 9,442,288 B2 | 9/2016 | Tanimura |
| 9,445,784 B2 | 9/2016 | O'Keeffe |
| 9,445,832 B2 | 9/2016 | Wiener et al. |
| 9,451,967 B2 | 9/2016 | Jordan et al. |

(56) References Cited

U.S. PATENT DOCUMENTS

| | | |
|---|---|---|
| 9,456,863 B2 | 10/2016 | Moua |
| 9,456,864 B2 | 10/2016 | Witt et al. |
| 9,468,438 B2 | 10/2016 | Baber et al. |
| 9,468,498 B2 | 10/2016 | Sigmon, Jr. |
| 9,474,542 B2 | 10/2016 | Slipszenko et al. |
| 9,474,568 B2 | 10/2016 | Akagane |
| 9,486,236 B2 | 11/2016 | Price et al. |
| 9,492,146 B2 | 11/2016 | Kostrzewski et al. |
| 9,492,224 B2 | 11/2016 | Boudreaux et al. |
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,465 B1 | 1/2017 | Liu et al. |
| 9,554,794 B2 | 1/2017 | Baber et al. |
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,572,592 B2 | 2/2017 | Price et al. |
| 9,574,644 B2 | 2/2017 | Parihar |
| 9,585,714 B2 | 3/2017 | Livneh |
| 9,592,056 B2 | 3/2017 | Mozdzierz et al. |
| 9,592,072 B2 | 3/2017 | Akagane |
| 9,597,143 B2 | 3/2017 | Madan et al. |
| 9,603,669 B2 | 3/2017 | Govari et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,629,623 B2 | 4/2017 | Lytle, IV et al. |
| 9,629,629 B2 | 4/2017 | Leimbach et al. |
| 9,632,573 B2 | 4/2017 | Ogawa et al. |
| 9,636,135 B2 | 5/2017 | Stulen |
| 9,636,165 B2 | 5/2017 | Larson et al. |
| 9,636,167 B2 | 5/2017 | Gregg |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,173 B2 | 5/2017 | Choi et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,674,949 B1 | 6/2017 | Liu et al. |
| 9,675,374 B2 | 6/2017 | Stulen et al. |
| 9,675,375 B2 | 6/2017 | Houser et al. |
| 9,681,884 B2 | 6/2017 | Clem et al. |
| 9,687,230 B2 | 6/2017 | Leimbach et al. |
| 9,687,290 B2 | 6/2017 | Keller |
| 9,690,362 B2 | 6/2017 | Leimbach et al. |
| 9,693,817 B2 | 7/2017 | Mehta et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,094 B2 | 8/2017 | Baber et al. |
| 9,724,118 B2 | 8/2017 | Schulte et al. |
| 9,724,120 B2 | 8/2017 | Faller et al. |
| 9,724,152 B2 | 8/2017 | Horlle et al. |
| 9,730,695 B2 | 8/2017 | Leimbach et al. |
| 9,733,663 B2 | 8/2017 | Leimbach et al. |
| 9,737,301 B2 | 8/2017 | Baber et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,757,128 B2 | 9/2017 | Baber et al. |
| 9,757,142 B2 | 9/2017 | Shimizu |
| 9,757,150 B2 | 9/2017 | Alexander et al. |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,169 B2 | 10/2017 | Kimsey et al. |
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,626 B2 | 10/2017 | Parihar et al. |
| 9,801,648 B2 | 10/2017 | Houser et al. |
| 9,802,033 B2 | 10/2017 | Hibner et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,815,211 B2 | 11/2017 | Cao et al. |
| 9,820,738 B2 | 11/2017 | Lytle, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,826,977 B2 | 11/2017 | Leimbach et al. |
| 9,839,443 B2 | 12/2017 | Brockman et al. |
| 9,844,368 B2 | 12/2017 | Boudreaux et al. |
| 9,844,374 B2 | 12/2017 | Lytle, IV et al. |
| 9,844,375 B2 | 12/2017 | Overmyer et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,381 B2 | 1/2018 | Johnson |
| 9,861,428 B2 | 1/2018 | Trees et al. |
| 9,867,612 B2 | 1/2018 | Parihar et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,877,782 B2 | 1/2018 | Voegele et al. |
| 9,878,184 B2 | 1/2018 | Beaupre |
| 9,883,860 B2 | 2/2018 | Leimbach et al. |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,895,148 B2 | 2/2018 | Shelton, IV et al. |
| 9,895,160 B2 | 2/2018 | Fan et al. |
| 9,901,321 B2 | 2/2018 | Harks et al. |
| 9,901,342 B2 | 2/2018 | Shelton, IV et al. |
| 9,901,383 B2 | 2/2018 | Hassler, Jr. |
| 9,901,754 B2 | 2/2018 | Yamada |
| 9,907,563 B2 | 3/2018 | Germain et al. |
| 9,913,642 B2 | 3/2018 | Leimbach et al. |
| 9,913,656 B2 | 3/2018 | Stulen |
| 9,913,680 B2 | 3/2018 | Voegele et al. |
| 9,918,730 B2 | 3/2018 | Trees et al. |
| 9,924,961 B2 | 3/2018 | Shelton, IV et al. |

(56) References Cited

U.S. PATENT DOCUMENTS

| | | |
|---|---|---|
| 9,925,003 B2 | 3/2018 | Parihar et al. |
| 9,931,118 B2 | 4/2018 | Shelton, IV et al. |
| 9,937,001 B2 | 4/2018 | Nakamura |
| 9,943,309 B2 | 4/2018 | Shelton, IV et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,968,355 B2 | 5/2018 | Shelton, IV et al. |
| 9,974,539 B2 | 5/2018 | Yates et al. |
| 9,987,000 B2 | 6/2018 | Shelton, IV et al. |
| 9,987,033 B2 | 6/2018 | Neurohr et al. |
| 9,993,248 B2 | 6/2018 | Shelton, IV et al. |
| 9,993,258 B2 | 6/2018 | Shelton, IV et al. |
| 9,993,289 B2 | 6/2018 | Sobajima et al. |
| 10,004,497 B2 | 6/2018 | Overmyer et al. |
| 10,004,501 B2 | 6/2018 | Shelton, IV et al. |
| 10,004,526 B2 | 6/2018 | Dycus et al. |
| 10,004,527 B2 | 6/2018 | Gee et al. |
| D822,206 S | 7/2018 | Shelton, IV et al. |
| 10,010,339 B2 | 7/2018 | Witt et al. |
| 10,010,341 B2 | 7/2018 | Houser et al. |
| 10,013,049 B2 | 7/2018 | Leimbach et al. |
| 10,016,199 B2 | 7/2018 | Baber et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| D826,405 S | 8/2018 | Shelton, IV et al. |
| 10,039,588 B2 | 8/2018 | Harper et al. |
| 10,041,822 B2 | 8/2018 | Zemlok |
| 10,045,776 B2 | 8/2018 | Shelton, IV et al. |
| 10,045,779 B2 | 8/2018 | Savage et al. |
| 10,045,794 B2 | 8/2018 | Witt et al. |
| 10,045,810 B2 | 8/2018 | Schall et al. |
| 10,045,819 B2 | 8/2018 | Jensen et al. |
| 10,052,044 B2 | 8/2018 | Shelton, IV et al. |
| 10,052,102 B2 | 8/2018 | Baxter, III et al. |
| 10,070,916 B2 | 9/2018 | Artale |
| 10,080,609 B2 | 9/2018 | Hancock et al. |
| 10,085,748 B2 | 10/2018 | Morgan et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,347 B2 | 10/2018 | Weisshaupt et al. |
| 10,092,348 B2 | 10/2018 | Boudreaux |
| 10,092,350 B2 | 10/2018 | Rothweiler et al. |
| 10,105,140 B2 | 10/2018 | Malinouskas et al. |
| 10,111,679 B2 | 10/2018 | Baber et al. |
| 10,111,699 B2 | 10/2018 | Boudreaux |
| 10,111,703 B2 | 10/2018 | Cosman, Jr. et al. |
| 10,117,649 B2 | 11/2018 | Baxter, III et al. |
| 10,117,667 B2 | 11/2018 | Robertson et al. |
| 10,117,702 B2 | 11/2018 | Danziger et al. |
| 10,123,835 B2 | 11/2018 | Keller et al. |
| 10,130,367 B2 | 11/2018 | Cappola et al. |
| 10,130,410 B2 | 11/2018 | Strobl et al. |
| 10,130,412 B2 | 11/2018 | Wham |
| 10,135,242 B2 | 11/2018 | Baber et al. |
| 10,136,887 B2 | 11/2018 | Shelton, IV et al. |
| 10,149,680 B2 | 12/2018 | Parihar et al. |
| 10,154,848 B2 | 12/2018 | Chernov et al. |
| 10,154,852 B2 | 12/2018 | Conlon et al. |
| 10,159,483 B2 | 12/2018 | Beckman et al. |
| 10,159,524 B2 | 12/2018 | Yates et al. |
| 10,166,060 B2 | 1/2019 | Johnson et al. |
| 10,172,665 B2 | 1/2019 | Heckel et al. |
| 10,172,669 B2 | 1/2019 | Felder et al. |
| 10,178,992 B2 | 1/2019 | Wise et al. |
| 10,179,022 B2 | 1/2019 | Yates et al. |
| 10,180,463 B2 | 1/2019 | Beckman et al. |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,188,455 B2 | 1/2019 | Hancock et al. |
| 10,194,907 B2 | 2/2019 | Marczyk et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,364 B2 | 2/2019 | Leimbach et al. |
| 10,201,365 B2 | 2/2019 | Boudreaux et al. |
| 10,201,382 B2 | 2/2019 | Wiener et al. |
| 10,206,676 B2 | 2/2019 | Shelton, IV |
| 10,226,250 B2 | 3/2019 | Beckman et al. |
| 10,226,273 B2 | 3/2019 | Messerly et al. |
| 10,231,747 B2 | 3/2019 | Stulen et al. |
| 10,238,385 B2 | 3/2019 | Yates et al. |
| 10,238,391 B2 | 3/2019 | Leimbach et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,095 B2 | 4/2019 | Boudreaux |
| 10,245,097 B2 | 4/2019 | Honda et al. |
| 10,245,104 B2 | 4/2019 | McKenna et al. |
| 10,251,664 B2 | 4/2019 | Shelton, IV et al. |
| 10,258,331 B2 | 4/2019 | Shelton, IV et al. |
| 10,258,505 B2 | 4/2019 | Ovchinnikov |
| 10,263,171 B2 | 4/2019 | Wiener et al. |
| 10,265,068 B2 | 4/2019 | Harris et al. |
| 10,265,117 B2 | 4/2019 | Wiener et al. |
| 10,265,118 B2 | 4/2019 | Gerhardt |
| 10,271,840 B2 | 4/2019 | Sapre |
| 10,271,851 B2 | 4/2019 | Shelton, IV et al. |
| D847,989 S | 5/2019 | Shelton, IV et al. |
| 10,278,721 B2 | 5/2019 | Dietz et al. |
| 10,285,705 B2 | 5/2019 | Shelton, IV et al. |
| 10,285,724 B2 | 5/2019 | Faller et al. |
| 10,285,750 B2 | 5/2019 | Coulson et al. |
| 10,292,704 B2 | 5/2019 | Harris et al. |
| 10,299,810 B2 | 5/2019 | Robertson et al. |
| 10,299,821 B2 | 5/2019 | Shelton, IV et al. |
| D850,617 S | 6/2019 | Shelton, IV et al. |
| D851,762 S | 6/2019 | Shelton, IV et al. |
| 10,307,159 B2 | 6/2019 | Harris et al. |
| 10,314,579 B2 | 6/2019 | Chowaniec et al. |
| 10,314,582 B2 | 6/2019 | Shelton, IV et al. |
| 10,314,638 B2 | 6/2019 | Gee et al. |
| 10,321,907 B2 | 6/2019 | Shelton, IV et al. |
| 10,321,950 B2 | 6/2019 | Yates et al. |
| D854,151 S | 7/2019 | Shelton, IV et al. |
| 10,335,149 B2 | 7/2019 | Baxter, II et al. |
| 10,335,182 B2 | 7/2019 | Stulen et al. |
| 10,335,183 B2 | 7/2019 | Worrell et al. |
| 10,335,614 B2 | 7/2019 | Messerly et al. |
| 10,342,543 B2 | 7/2019 | Shelton, IV et al. |
| 10,342,606 B2 | 7/2019 | Cosman et al. |
| 10,342,623 B2 | 7/2019 | Huelman et al. |
| 10,348,941 B2 | 7/2019 | Elliot, Jr. et al. |
| 10,349,999 B2 | 7/2019 | Yates et al. |
| 10,350,016 B2 | 7/2019 | Burbank et al. |
| 10,350,025 B1 | 7/2019 | Loyd et al. |
| 10,357,246 B2 | 7/2019 | Shelton, IV et al. |
| 10,357,247 B2 | 7/2019 | Shelton, IV et al. |
| 10,357,303 B2 | 7/2019 | Conlon et al. |
| 10,363,084 B2 | 7/2019 | Friedrichs |
| 10,368,861 B2 | 8/2019 | Baxter, II et al. |
| 10,368,865 B2 | 8/2019 | Harris et al. |
| 10,376,263 B2 | 8/2019 | Morgan et al. |
| 10,376,305 B2 | 8/2019 | Yates et al. |
| 10,390,841 B2 | 8/2019 | Shelton, IV et al. |
| 10,398,439 B2 | 9/2019 | Cabrera et al. |
| 10,398,466 B2 | 9/2019 | Stulen et al. |
| 10,398,497 B2 | 9/2019 | Batross et al. |
| 10,405,857 B2 | 9/2019 | Shelton, IV et al. |
| 10,405,863 B2 | 9/2019 | Wise et al. |
| 10,413,291 B2 | 9/2019 | Worthington et al. |

(56) References Cited

U.S. PATENT DOCUMENTS

| | | |
|---|---|---|
| 10,413,293 B2 | 9/2019 | Shelton, IV et al. |
| 10,413,297 B2 | 9/2019 | Harris et al. |
| 10,413,352 B2 | 9/2019 | Thomas et al. |
| 10,413,353 B2 | 9/2019 | Kerr et al. |
| 10,420,552 B2 | 9/2019 | Shelton, IV et al. |
| 10,420,579 B2 | 9/2019 | Wiener et al. |
| 10,420,607 B2 | 9/2019 | Woloszko et al. |
| D865,175 S | 10/2019 | Widenhouse et al. |
| 10,426,471 B2 | 10/2019 | Shelton, IV et al. |
| 10,426,507 B2 | 10/2019 | Wiener et al. |
| 10,426,546 B2 | 10/2019 | Graham et al. |
| 10,426,978 B2 | 10/2019 | Akagane |
| 10,433,837 B2 | 10/2019 | Worthington et al. |
| 10,433,849 B2 | 10/2019 | Shelton, IV et al. |
| 10,433,865 B2 | 10/2019 | Witt et al. |
| 10,433,866 B2 | 10/2019 | Witt et al. |
| 10,433,900 B2 | 10/2019 | Harris et al. |
| 10,441,279 B2 | 10/2019 | Shelton, IV et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,448,986 B2 | 10/2019 | Zikorus et al. |
| 10,456,140 B2 | 10/2019 | Shelton, IV et al. |
| 10,456,193 B2 | 10/2019 | Yates et al. |
| 10,463,421 B2 | 11/2019 | Boudreaux et al. |
| 10,463,887 B2 | 11/2019 | Witt et al. |
| 10,470,762 B2 | 11/2019 | Leimbach et al. |
| 10,470,764 B2 | 11/2019 | Baxter, III et al. |
| 10,478,182 B2 | 11/2019 | Taylor |
| 10,478,190 B2 | 11/2019 | Miller et al. |
| 10,485,542 B2 | 11/2019 | Shelton, IV et al. |
| 10,485,543 B2 | 11/2019 | Shelton, IV et al. |
| 10,485,607 B2 | 11/2019 | Strobl et al. |
| D869,655 S | 12/2019 | Shelton, IV et al. |
| 10,492,785 B2 | 12/2019 | Overmyer et al. |
| 10,492,849 B2 | 12/2019 | Juergens et al. |
| 10,499,914 B2 | 12/2019 | Huang et al. |
| 10,507,033 B2 | 12/2019 | Dickerson et al. |
| 10,512,795 B2 | 12/2019 | Voegele et al. |
| 10,517,595 B2 | 12/2019 | Hunter et al. |
| 10,517,596 B2 | 12/2019 | Hunter et al. |
| 10,517,627 B2 | 12/2019 | Timm et al. |
| 10,524,787 B2 | 1/2020 | Shelton, IV et al. |
| 10,524,789 B2 | 1/2020 | Swayze et al. |
| 10,524,854 B2 | 1/2020 | Woodruff et al. |
| 10,524,872 B2 | 1/2020 | Stewart et al. |
| 10,531,874 B2 | 1/2020 | Morgan et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,543,008 B2 | 1/2020 | Vakharia et al. |
| 10,548,504 B2 | 2/2020 | Shelton, IV et al. |
| 10,548,655 B2 | 2/2020 | Scheib et al. |
| 10,555,769 B2 | 2/2020 | Worrell et al. |
| 10,561,560 B2 | 2/2020 | Boutoussov et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,575,892 B2 | 3/2020 | Danziger et al. |
| 10,582,928 B2 | 3/2020 | Hunter et al. |
| 10,588,625 B2 | 3/2020 | Weaner et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,595,929 B2 | 3/2020 | Boudreaux et al. |
| 10,595,930 B2 | 3/2020 | Scheib et al. |
| 10,603,036 B2 | 3/2020 | Hunter et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,420 B2 | 4/2020 | Shelton, IV et al. |
| 10,617,464 B2 | 4/2020 | Duppuis |
| 10,624,635 B2 | 4/2020 | Harris et al. |
| 10,624,691 B2 | 4/2020 | Wiener et al. |
| 10,631,858 B2 | 4/2020 | Burbank |
| 10,631,859 B2 | 4/2020 | Shelton, IV et al. |
| 10,631,928 B2 | 4/2020 | Basu et al. |
| 10,632,630 B2 | 4/2020 | Cao et al. |
| RE47,996 E | 5/2020 | Turner et al. |
| 10,639,034 B2 | 5/2020 | Harris et al. |
| 10,639,035 B2 | 5/2020 | Shelton, IV et al. |
| 10,639,037 B2 | 5/2020 | Shelton, IV et al. |
| 10,639,092 B2 | 5/2020 | Corbett et al. |
| 10,639,098 B2 | 5/2020 | Cosman et al. |
| 10,646,269 B2 | 5/2020 | Worrell et al. |
| 10,646,292 B2 | 5/2020 | Solomon et al. |
| 10,653,413 B2 | 5/2020 | Worthington et al. |
| 10,660,692 B2 | 5/2020 | Lesko et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,677,764 B2 | 6/2020 | Ross et al. |
| 10,682,136 B2 | 6/2020 | Harris et al. |
| 10,682,138 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,688,321 B2 | 6/2020 | Wiener et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,119 B2 | 6/2020 | Smith |
| 10,702,270 B2 | 7/2020 | Shelton, IV et al. |
| 10,702,329 B2 | 7/2020 | Strobl et al. |
| 10,709,446 B2 | 7/2020 | Harris et al. |
| 10,709,469 B2 | 7/2020 | Shelton, IV et al. |
| 10,709,906 B2 | 7/2020 | Nield |
| 10,716,615 B2 | 7/2020 | Shelton, IV et al. |
| 10,722,233 B2 | 7/2020 | Wellman |
| D893,717 S | 8/2020 | Messerly et al. |
| 10,729,458 B2 | 8/2020 | Stoddard et al. |
| 10,729,494 B2 | 8/2020 | Parihar et al. |
| 10,736,629 B2 | 8/2020 | Shelton, IV et al. |
| 10,736,685 B2 | 8/2020 | Wiener et al. |
| 10,751,108 B2 | 8/2020 | Yates et al. |
| 10,751,138 B2 | 8/2020 | Giordano et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,294 B2 | 9/2020 | Jones |
| 10,765,427 B2 | 9/2020 | Shelton, IV et al. |
| 10,765,470 B2 | 9/2020 | Yates et al. |
| 10,772,629 B2 | 9/2020 | Shelton, IV et al. |
| 10,772,630 B2 | 9/2020 | Wixey |
| 10,779,821 B2 | 9/2020 | Harris et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,845 B2 | 9/2020 | Timm et al. |
| 10,779,849 B2 | 9/2020 | Shelton, IV et al. |
| 10,779,879 B2 | 9/2020 | Yates et al. |
| 10,786,253 B2 | 9/2020 | Shelton, IV et al. |
| 10,786,276 B2 | 9/2020 | Hirai et al. |
| 10,806,454 B2 | 10/2020 | Kopp |
| 10,813,638 B2 | 10/2020 | Shelton, IV et al. |
| 10,820,938 B2 | 11/2020 | Fischer et al. |
| 10,828,032 B2 | 11/2020 | Leimbach et al. |
| 10,828,058 B2 | 11/2020 | Shelton, IV et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |

(56) References Cited

U.S. PATENT DOCUMENTS

| | | |
|---|---|---|
| 10,835,307 B2 | 11/2020 | Shelton, IV et al. |
| 10,842,492 B2 | 11/2020 | Shelton, IV et al. |
| 10,842,523 B2 | 11/2020 | Shelton, IV et al. |
| 10,842,563 B2 | 11/2020 | Gilbert et al. |
| D906,355 S | 12/2020 | Messerly et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,856,896 B2 | 12/2020 | Eichmann et al. |
| 10,856,929 B2 | 12/2020 | Yates et al. |
| 10,856,934 B2 | 12/2020 | Trees et al. |
| 10,874,465 B2 | 12/2020 | Weir et al. |
| D908,216 S | 1/2021 | Messerly et al. |
| 10,881,399 B2 | 1/2021 | Shelton, IV et al. |
| 10,881,401 B2 | 1/2021 | Baber et al. |
| 10,881,409 B2 | 1/2021 | Cabrera |
| 10,881,449 B2 | 1/2021 | Boudreaux et al. |
| 10,888,322 B2 | 1/2021 | Morgan et al. |
| 10,888,347 B2 | 1/2021 | Witt et al. |
| 10,893,863 B2 | 1/2021 | Shelton, IV et al. |
| 10,893,864 B2 | 1/2021 | Harris et al. |
| 10,893,883 B2 | 1/2021 | Dannaher |
| 10,898,186 B2 | 1/2021 | Bakos et al. |
| 10,898,256 B2 | 1/2021 | Yates et al. |
| 10,912,559 B2 | 2/2021 | Harris et al. |
| 10,912,580 B2 | 2/2021 | Green et al. |
| 10,912,603 B2 | 2/2021 | Boudreaux et al. |
| 10,918,385 B2 | 2/2021 | Overmyer et al. |
| 10,925,659 B2 | 2/2021 | Shelton, IV et al. |
| 10,926,022 B2 | 2/2021 | Hickey et al. |
| D914,878 S | 3/2021 | Shelton, IV et al. |
| 10,932,766 B2 | 3/2021 | Tesar et al. |
| 10,932,847 B2 | 3/2021 | Yates et al. |
| 10,945,727 B2 | 3/2021 | Shelton, IV et al. |
| 10,952,788 B2 | 3/2021 | Asher et al. |
| 10,959,727 B2 | 3/2021 | Hunter et al. |
| 10,966,741 B2 | 4/2021 | Illizaliturri-Sanchez et al. |
| 10,966,747 B2 | 4/2021 | Worrell et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,980,536 B2 | 4/2021 | Weaner et al. |
| 10,987,105 B2 | 4/2021 | Cappola et al. |
| 10,987,123 B2 | 4/2021 | Weir et al. |
| 10,987,156 B2 | 4/2021 | Trees et al. |
| 10,993,715 B2 | 5/2021 | Shelton, IV et al. |
| 10,993,716 B2 | 5/2021 | Shelton, IV et al. |
| 10,993,763 B2 | 5/2021 | Batross et al. |
| 11,000,278 B2 | 5/2021 | Shelton, IV et al. |
| 11,000,279 B2 | 5/2021 | Shelton, IV et al. |
| 11,020,114 B2 | 6/2021 | Shelton, IV et al. |
| 11,020,140 B2 | 6/2021 | Gee et al. |
| 11,033,322 B2 | 6/2021 | Wiener et al. |
| 11,039,834 B2 | 6/2021 | Harris et al. |
| 11,045,191 B2 | 6/2021 | Shelton, IV et al. |
| 11,045,192 B2 | 6/2021 | Harris et al. |
| 11,045,275 B2 | 6/2021 | Boudreaux et al. |
| 11,051,840 B2 | 7/2021 | Shelton, IV et al. |
| 11,051,873 B2 | 7/2021 | Wiener et al. |
| 11,058,424 B2 | 7/2021 | Shelton, IV et al. |
| 11,058,447 B2 | 7/2021 | Houser |
| 11,058,448 B2 | 7/2021 | Shelton, IV et al. |
| 11,058,475 B2 | 7/2021 | Wiener et al. |
| 11,064,997 B2 | 7/2021 | Shelton, IV et al. |
| 11,065,048 B2 | 7/2021 | Messerly et al. |
| 11,083,455 B2 | 8/2021 | Shelton, IV et al. |
| 11,083,458 B2 | 8/2021 | Harris et al. |
| 11,090,048 B2 | 8/2021 | Fanelli et al. |
| 11,090,049 B2 | 8/2021 | Bakos et al. |
| 11,090,104 B2 | 8/2021 | Wiener et al. |
| 11,096,688 B2 | 8/2021 | Shelton, IV et al. |
| 11,096,752 B2 | 8/2021 | Stulen et al. |
| 11,109,866 B2 | 9/2021 | Shelton, IV et al. |
| 11,129,611 B2 | 9/2021 | Shelton, IV et al. |
| 11,129,666 B2 | 9/2021 | Messerly et al. |
| 11,129,669 B2 | 9/2021 | Stulen et al. |
| 11,129,670 B2 | 9/2021 | Shelton, IV et al. |
| 11,134,942 B2 | 10/2021 | Harris et al. |
| 11,134,978 B2 | 10/2021 | Shelton, IV et al. |
| 11,141,154 B2 | 10/2021 | Shelton, IV et al. |
| 11,141,213 B2 | 10/2021 | Yates et al. |
| 11,147,551 B2 | 10/2021 | Shelton, IV |
| 11,147,553 B2 | 10/2021 | Shelton, IV |
| 11,160,551 B2 | 11/2021 | Shelton, IV et al. |
| 11,166,716 B2 | 11/2021 | Shelton, IV et al. |
| 11,172,929 B2 | 11/2021 | Shelton, IV |
| 11,179,155 B2 | 11/2021 | Shelton, IV et al. |
| 11,179,173 B2 | 11/2021 | Price et al. |
| 11,191,539 B2 | 12/2021 | Overmyer et al. |
| 11,191,540 B2 | 12/2021 | Aronhalt et al. |
| 11,197,668 B2 | 12/2021 | Shelton, IV et al. |
| 11,202,670 B2 | 12/2021 | Worrell et al. |
| 11,207,065 B2 | 12/2021 | Harris et al. |
| 11,207,067 B2 | 12/2021 | Shelton, IV et al. |
| 11,213,293 B2 | 1/2022 | Worthington et al. |
| 11,213,294 B2 | 1/2022 | Shelton, IV et al. |
| 11,219,453 B2 | 1/2022 | Shelton, IV et al. |
| 11,224,426 B2 | 1/2022 | Shelton, IV et al. |
| 11,224,497 B2 | 1/2022 | Shelton, IV et al. |
| 11,229,437 B2 | 1/2022 | Shelton, IV et al. |
| 11,229,450 B2 | 1/2022 | Shelton, IV et al. |
| 11,229,471 B2 | 1/2022 | Shelton, IV et al. |
| 11,229,472 B2 | 1/2022 | Shelton, IV et al. |
| 11,234,698 B2 | 2/2022 | Shelton, IV et al. |
| 11,241,235 B2 | 2/2022 | Shelton, IV et al. |
| 11,246,592 B2 | 2/2022 | Shelton, IV et al. |
| 11,246,625 B2 | 2/2022 | Kane et al. |
| 11,246,678 B2 | 2/2022 | Shelton, IV et al. |
| 11,253,256 B2 | 2/2022 | Harris et al. |
| 11,259,803 B2 | 3/2022 | Shelton, IV et al. |
| 11,259,805 B2 | 3/2022 | Shelton, IV et al. |
| 11,259,806 B2 | 3/2022 | Shelton, IV et al. |
| 11,259,807 B2 | 3/2022 | Shelton, IV et al. |
| 11,266,405 B2 | 3/2022 | Shelton, IV et al. |
| 11,266,430 B2 | 3/2022 | Clauda et al. |
| 11,272,931 B2 | 3/2022 | Boudreaux et al. |
| 11,278,280 B2 | 3/2022 | Shelton, IV et al. |
| 11,284,890 B2 | 3/2022 | Nalagatla et al. |
| 11,291,440 B2 | 4/2022 | Harris et al. |
| 11,291,444 B2 | 4/2022 | Boudreaux et al. |
| 11,291,445 B2 | 4/2022 | Shelton, IV et al. |
| 11,291,447 B2 | 4/2022 | Shelton, IV et al. |
| 11,291,451 B2 | 4/2022 | Shelton, IV |
| 11,298,127 B2 | 4/2022 | Shelton, IV |
| 11,298,129 B2 | 4/2022 | Bakos et al. |
| 11,298,130 B2 | 4/2022 | Bakos et al. |
| 11,304,695 B2 | 4/2022 | Shelton, IV et al. |
| 11,304,696 B2 | 4/2022 | Shelton, IV et al. |
| 11,304,699 B2 | 4/2022 | Shelton, IV et al. |
| 11,311,306 B2 | 4/2022 | Shelton, IV et al. |
| 11,311,326 B2 | 4/2022 | Boudreaux |
| 11,311,342 B2 | 4/2022 | Parihar et al. |
| D950,728 S | 5/2022 | Bakos et al. |
| D952,144 S | 5/2022 | Boudreaux |
| 11,317,915 B2 | 5/2022 | Boudreaux et al. |
| 11,324,503 B2 | 5/2022 | Shelton, IV et al. |
| 11,324,527 B2 | 5/2022 | Aldridge et al. |
| 11,324,557 B2 | 5/2022 | Shelton, IV et al. |
| 11,331,100 B2 | 5/2022 | Boudreaux et al. |
| 11,331,101 B2 | 5/2022 | Harris et al. |
| 11,337,747 B2 | 5/2022 | Voegele et al. |
| 11,344,362 B2 | 5/2022 | Yates et al. |
| 11,350,938 B2 | 6/2022 | Shelton, IV et al. |
| 11,357,503 B2 | 6/2022 | Bakos et al. |
| 11,361,176 B2 | 6/2022 | Shelton, IV et al. |
| 11,369,377 B2 | 6/2022 | Boudreaux et al. |
| 11,376,098 B2 | 7/2022 | Shelton, IV et al. |
| 11,382,642 B2 | 7/2022 | Robertson et al. |
| 11,389,161 B2 | 7/2022 | Shelton, IV et al. |
| 11,389,164 B2 | 7/2022 | Yates et al. |
| 11,399,837 B2 | 8/2022 | Shelton, IV et al. |
| 11,399,855 B2 | 8/2022 | Boudreaux et al. |
| 11,406,382 B2 | 8/2022 | Shelton, IV et al. |

(56) References Cited

U.S. PATENT DOCUMENTS

| | | |
|---|---|---|
| 11,406,386 B2 | 8/2022 | Baber et al. |
| 11,413,060 B2 | 8/2022 | Faller et al. |
| 11,419,606 B2 | 8/2022 | Overmyer et al. |
| 11,419,626 B2 | 8/2022 | Timm et al. |
| 11,424,027 B2 | 8/2022 | Shelton, IV |
| 11,426,167 B2 | 8/2022 | Shelton, IV et al. |
| 11,426,191 B2 | 8/2022 | Vakharia et al. |
| D964,564 S | 9/2022 | Boudreaux |
| 11,446,029 B2 | 9/2022 | Shelton, IV et al. |
| 11,452,525 B2 | 9/2022 | Shelton, IV et al. |
| 11,464,511 B2 | 10/2022 | Timm et al. |
| 11,464,512 B2 | 10/2022 | Shelton, IV et al. |
| 11,464,601 B2 | 10/2022 | Shelton, IV et al. |
| 11,471,155 B2 | 10/2022 | Shelton, IV et al. |
| 11,471,156 B2 | 10/2022 | Shelton, IV et al. |
| 11,471,206 B2 | 10/2022 | Henderson et al. |
| 11,471,209 B2 | 10/2022 | Yates et al. |
| 11,478,242 B2 | 10/2022 | Shelton, IV et al. |
| 11,484,310 B2 | 11/2022 | Shelton, IV et al. |
| 11,497,547 B2 | 11/2022 | McKenna et al. |
| 11,504,122 B2 | 11/2022 | Shelton, IV et al. |
| 11,517,309 B2 | 12/2022 | Bakos et al. |
| 11,529,137 B2 | 12/2022 | Shelton, IV et al. |
| 11,529,139 B2 | 12/2022 | Shelton, IV et al. |
| 11,553,971 B2 | 1/2023 | Shelton, IV et al. |
| 11,559,304 B2 | 1/2023 | Boudreaux et al. |
| 11,559,307 B2 | 1/2023 | Shelton, IV et al. |
| 11,559,308 B2 | 1/2023 | Yates et al. |
| 11,559,347 B2 | 1/2023 | Wiener et al. |
| 11,571,210 B2 | 2/2023 | Shelton, IV et al. |
| 11,576,672 B2 | 2/2023 | Shelton, IV et al. |
| 11,576,677 B2 | 2/2023 | Shelton, IV et al. |
| 11,583,306 B2 | 2/2023 | Olson et al. |
| 11,589,865 B2 | 2/2023 | Shelton, IV et al. |
| 11,589,888 B2 | 2/2023 | Shelton, IV et al. |
| 11,589,916 B2 | 2/2023 | Shelton, IV et al. |
| 11,607,219 B2 | 3/2023 | Shelton, IV et al. |
| 11,638,587 B2 | 5/2023 | Shelton, IV et al. |
| 11,653,920 B2 | 5/2023 | Shelton, IV et al. |
| 11,659,023 B2 | 5/2023 | Shelton, IV et al. |
| 11,660,089 B2 | 5/2023 | Shelton, IV et al. |
| 11,660,163 B2 | 5/2023 | Shelton, IV et al. |
| 11,666,368 B2 | 6/2023 | Henderson et al. |
| 11,666,375 B2 | 6/2023 | Scheib et al. |
| 11,678,880 B2 | 6/2023 | Shelton, IV et al. |
| 11,678,925 B2 | 6/2023 | Henderson et al. |
| 11,684,402 B2 | 6/2023 | Shelton, IV et al. |
| 11,684,412 B2 | 6/2023 | Shelton, IV et al. |
| 11,684,434 B2 | 6/2023 | Shelton, IV |
| 11,696,759 B2 | 7/2023 | Shelton, IV et al. |
| 11,696,761 B2 | 7/2023 | Shelton, IV |
| 11,696,776 B2 | 7/2023 | Shelton, IV et al. |
| 11,701,111 B2 | 7/2023 | Shelton, IV et al. |
| 11,707,318 B2 | 7/2023 | Shelton, IV et al. |
| 11,717,311 B2 | 8/2023 | Weir et al. |
| 11,717,706 B2 | 8/2023 | Wiener et al. |
| 11,723,716 B2 | 8/2023 | Fiebig et al. |
| 11,744,636 B2 | 9/2023 | Shelton, IV et al. |
| 11,751,872 B2 | 9/2023 | Zeiner et al. |
| 11,751,929 B2 | 9/2023 | Shelton, IV et al. |
| 11,759,251 B2 | 9/2023 | Shelton, IV et al. |
| 11,766,287 B2 | 9/2023 | Wiener et al. |
| 11,771,419 B2 | 10/2023 | Shelton, IV et al. |
| 11,779,329 B2 | 10/2023 | Shelton, IV et al. |
| 11,779,387 B2 | 10/2023 | Salguero et al. |
| 11,786,291 B2 | 10/2023 | Sarley et al. |
| 11,786,294 B2 | 10/2023 | Shelton, IV et al. |
| 11,812,957 B2 | 11/2023 | Shelton, IV et al. |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0019649 A1 | 2/2002 | Sikora et al. |
| 2002/0022836 A1 | 2/2002 | Goble et al. |
| 2002/0029036 A1 | 3/2002 | Goble et al. |
| 2002/0029055 A1 | 3/2002 | Bonutti |
| 2002/0032452 A1 | 3/2002 | Tierney et al. |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0123749 A1 | 9/2002 | Jain |
| 2002/0133152 A1 | 9/2002 | Strul |
| 2002/0151884 A1 | 10/2002 | Hoey et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2002/0177373 A1 | 11/2002 | Shibata et al. |
| 2002/0177862 A1 | 11/2002 | Aranyi et al. |
| 2003/0009164 A1 | 1/2003 | Woloszko et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0073981 A1 | 4/2003 | Whitman et al. |
| 2003/0109778 A1 | 6/2003 | Rashidi |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0176778 A1 | 9/2003 | Messing et al. |
| 2003/0181898 A1 | 9/2003 | Bowers |
| 2003/0199794 A1 | 10/2003 | Sakurai et al. |
| 2003/0204199 A1 | 10/2003 | Novak et al. |
| 2003/0208186 A1 | 11/2003 | Moreyra |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0094597 A1 | 5/2004 | Whitman et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0143263 A1 | 7/2004 | Schechter et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0181242 A1 | 9/2004 | Stack et al. |
| 2004/0193150 A1 | 9/2004 | Sharkey et al. |
| 2004/0193153 A1 | 9/2004 | Sartor et al. |
| 2004/0193212 A1 | 9/2004 | Taniguchi et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |

(56) References Cited

U.S. PATENT DOCUMENTS

| | | |
|---|---|---|
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0080427 A1 | 4/2005 | Govari et al. |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0107777 A1 | 5/2005 | West et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0171533 A1 | 8/2005 | Latterell et al. |
| 2005/0177184 A1 | 8/2005 | Easley |
| 2005/0182339 A1 | 8/2005 | Lee et al. |
| 2005/0187576 A1 | 8/2005 | Whitman et al. |
| 2005/0188743 A1 | 9/2005 | Land |
| 2005/0192610 A1 | 9/2005 | Houser et al. |
| 2005/0192611 A1 | 9/2005 | Houser |
| 2005/0206583 A1 | 9/2005 | Lemelson et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0262175 A1 | 11/2005 | Iino et al. |
| 2005/0267464 A1 | 12/2005 | Truckai et al. |
| 2005/0271807 A1 | 12/2005 | Iljima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0142656 A1 | 6/2006 | Malackowski et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217700 A1 | 9/2006 | Garito et al. |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0259026 A1 | 11/2006 | Godara et al. |
| 2006/0259102 A1 | 11/2006 | Slatkine |
| 2006/0264809 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0129726 A1 | 6/2007 | Eder et al. |
| 2007/0130771 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175955 A1 | 8/2007 | Shelton et al. |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0013809 A1 | 1/2008 | Zhu et al. |
| 2008/0015473 A1 | 1/2008 | Shimizu |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0046122 A1 | 2/2008 | Manzo et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0161809 A1 | 7/2008 | Schmitz et al. |
| 2008/0167670 A1 | 7/2008 | Shelton et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0275440 A1 | 11/2008 | Kratoska et al. |
| 2008/0281200 A1 | 11/2008 | Voic et al. |
| 2008/0281315 A1 | 11/2008 | Gines |
| 2008/0287944 A1 | 11/2008 | Pearson et al. |

(56) References Cited

U.S. PATENT DOCUMENTS

| | | |
|---|---|---|
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0036913 A1 | 2/2009 | Wiener et al. |
| 2009/0043293 A1 | 2/2009 | Pankratov et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0065565 A1 | 3/2009 | Cao |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088745 A1 | 4/2009 | Hushka et al. |
| 2009/0088785 A1 | 4/2009 | Masuda |
| 2009/0090763 A1 | 4/2009 | Zemlok et al. |
| 2009/0101692 A1 | 4/2009 | Whitman et al. |
| 2009/0105750 A1 | 4/2009 | Price et al. |
| 2009/0112206 A1 | 4/2009 | Dumbauld et al. |
| 2009/0118751 A1 | 5/2009 | Wiener et al. |
| 2009/0131885 A1 | 5/2009 | Akahoshi |
| 2009/0131934 A1 | 5/2009 | Odom et al. |
| 2009/0138025 A1 | 5/2009 | Stahler et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0157064 A1 | 6/2009 | Hodel |
| 2009/0163807 A1 | 6/2009 | Sliwa |
| 2009/0177119 A1 | 7/2009 | Heidner et al. |
| 2009/0179923 A1 | 7/2009 | Amundson et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0182333 A1 | 7/2009 | Eder et al. |
| 2009/0192441 A1 | 7/2009 | Gelbart et al. |
| 2009/0198272 A1 | 8/2009 | Kerver et al. |
| 2009/0204114 A1 | 8/2009 | Odom |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |
| 2009/0248022 A1 | 10/2009 | Falkenstein et al. |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0292283 A1 | 11/2009 | Odom |
| 2009/0299141 A1 | 12/2009 | Downey et al. |
| 2009/0306639 A1 | 12/2009 | Nevo et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0036373 A1 | 2/2010 | Ward |
| 2010/0042093 A9 | 2/2010 | Wham et al. |
| 2010/0049180 A1 | 2/2010 | Wells et al. |
| 2010/0057081 A1 | 3/2010 | Hanna |
| 2010/0057118 A1 | 3/2010 | Dietz et al. |
| 2010/0063437 A1 | 3/2010 | Nelson et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0145335 A1 | 6/2010 | Johnson et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0193566 A1 | 8/2010 | Scheib et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0225209 A1 | 9/2010 | Goldberg et al. |
| 2010/0228249 A1 | 9/2010 | Mohr et al. |
| 2010/0228250 A1 | 9/2010 | Brogna |
| 2010/0234906 A1 | 9/2010 | Koh |
| 2010/0256635 A1 | 10/2010 | McKenna et al. |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0305564 A1 | 12/2010 | Livneh |
| 2010/0331742 A1 | 12/2010 | Masuda |
| 2010/0331871 A1 | 12/2010 | Nield et al. |
| 2011/0004233 A1 | 1/2011 | Muir et al. |
| 2011/0015632 A1 | 1/2011 | Artale |
| 2011/0015650 A1 | 1/2011 | Choi et al. |
| 2011/0022032 A1 | 1/2011 | Zemlok et al. |
| 2011/0028964 A1 | 2/2011 | Edwards |
| 2011/0071523 A1 | 3/2011 | Dickhans |
| 2011/0082494 A1 | 4/2011 | Kerr et al. |
| 2011/0106141 A1 | 5/2011 | Nakamura |
| 2011/0112400 A1 | 5/2011 | Emery et al. |
| 2011/0125149 A1 | 5/2011 | El-Galley et al. |
| 2011/0125151 A1 | 5/2011 | Strauss et al. |
| 2011/0144640 A1 | 6/2011 | Heinrich et al. |
| 2011/0160725 A1 | 6/2011 | Kabaya et al. |
| 2011/0238010 A1 | 9/2011 | Kirschenman et al. |
| 2011/0238079 A1 | 9/2011 | Hannaford et al. |
| 2011/0273465 A1 | 11/2011 | Konishi et al. |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022528 A1 | 1/2012 | White et al. |
| 2012/0022583 A1 | 1/2012 | Sugalski et al. |
| 2012/0041358 A1 | 2/2012 | Mann et al. |
| 2012/0053597 A1 | 3/2012 | Anvari et al. |
| 2012/0059286 A1 | 3/2012 | Hastings et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0080344 A1 | 4/2012 | Shelton, IV |
| 2012/0101493 A1 | 4/2012 | Masuda et al. |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0136279 A1 | 5/2012 | Tanaka et al. |
| 2012/0136347 A1 | 5/2012 | Brustad et al. |
| 2012/0136386 A1 | 5/2012 | Kishida et al. |
| 2012/0143182 A1 | 6/2012 | Ullrich et al. |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0191091 A1 | 7/2012 | Allen |
| 2012/0193396 A1 | 8/2012 | Zemlok et al. |
| 2012/0211542 A1 | 8/2012 | Racenet |
| 2012/0226266 A1 | 9/2012 | Ghosal et al. |

(56) References Cited

U.S. PATENT DOCUMENTS

| | | |
|---|---|---|
| 2012/0234893 A1 | 9/2012 | Schuckmann et al. |
| 2012/0253328 A1 | 10/2012 | Cunningham et al. |
| 2012/0253329 A1 | 10/2012 | Zemlok et al. |
| 2012/0265241 A1 | 10/2012 | Hart et al. |
| 2012/0296239 A1 | 11/2012 | Chernov et al. |
| 2012/0296325 A1 | 11/2012 | Takashino |
| 2012/0296371 A1 | 11/2012 | Kappus et al. |
| 2013/0023925 A1 | 1/2013 | Mueller |
| 2013/0071282 A1 | 3/2013 | Fry |
| 2013/0085510 A1 | 4/2013 | Stefanchik et al. |
| 2013/0103031 A1 | 4/2013 | Garrison |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0190760 A1 | 7/2013 | Allen, IV et al. |
| 2013/0214025 A1 | 8/2013 | Zemlok et al. |
| 2013/0253256 A1 | 9/2013 | Griffith et al. |
| 2013/0253480 A1 | 9/2013 | Kimball et al. |
| 2013/0264369 A1 | 10/2013 | Whitman |
| 2013/0267874 A1 | 10/2013 | Marcotte et al. |
| 2013/0277410 A1 | 10/2013 | Fernandez et al. |
| 2013/0296843 A1 | 11/2013 | Boudreaux et al. |
| 2013/0321425 A1 | 12/2013 | Greene et al. |
| 2013/0334989 A1 | 12/2013 | Kataoka |
| 2013/0345701 A1 | 12/2013 | Allen, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005663 A1 | 1/2014 | Heard et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0077426 A1 | 3/2014 | Park |
| 2014/0107538 A1 | 4/2014 | Wiener et al. |
| 2014/0121569 A1 | 5/2014 | Schafer et al. |
| 2014/0135804 A1 | 5/2014 | Weisenburgh, II et al. |
| 2014/0163541 A1 | 6/2014 | Shelton, IV et al. |
| 2014/0163549 A1 | 6/2014 | Yates et al. |
| 2014/0180274 A1 | 6/2014 | Kabaya et al. |
| 2014/0180310 A1 | 6/2014 | Blumenkranz et al. |
| 2014/0194868 A1 | 7/2014 | Sanai et al. |
| 2014/0194874 A1 | 7/2014 | Dietz et al. |
| 2014/0194875 A1 | 7/2014 | Reschke et al. |
| 2014/0207124 A1 | 7/2014 | Aldridge et al. |
| 2014/0207135 A1 | 7/2014 | Winter |
| 2014/0221994 A1 | 8/2014 | Reschke |
| 2014/0236152 A1 | 8/2014 | Walberg et al. |
| 2014/0246475 A1 | 9/2014 | Hall et al. |
| 2014/0249557 A1 | 9/2014 | Koch, Jr. et al. |
| 2014/0263541 A1 | 9/2014 | Leimbach et al. |
| 2014/0263552 A1 | 9/2014 | Hall et al. |
| 2014/0276794 A1 | 9/2014 | Batchelor et al. |
| 2014/0276797 A1 | 9/2014 | Batchelor et al. |
| 2014/0276798 A1 | 9/2014 | Batchelor et al. |
| 2014/0303605 A1 | 10/2014 | Boyden et al. |
| 2014/0303612 A1 | 10/2014 | Williams |
| 2014/0357984 A1 | 12/2014 | Wallace et al. |
| 2014/0373003 A1 | 12/2014 | Grez et al. |
| 2015/0014392 A1 | 1/2015 | Williams et al. |
| 2015/0025528 A1 | 1/2015 | Arts |
| 2015/0032150 A1 | 1/2015 | Ishida et al. |
| 2015/0048140 A1 | 2/2015 | Penna et al. |
| 2015/0066027 A1 | 3/2015 | Garrison et al. |
| 2015/0080876 A1 | 3/2015 | Worrell et al. |
| 2015/0080887 A1 | 3/2015 | Sobajima et al. |
| 2015/0080889 A1 | 3/2015 | Cunningham et al. |
| 2015/0088122 A1 | 3/2015 | Jensen |
| 2015/0100056 A1 | 4/2015 | Nakamura |
| 2015/0112335 A1 | 4/2015 | Boudreaux et al. |
| 2015/0119901 A1 | 4/2015 | Steege |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0230796 A1 | 8/2015 | Calderoni |
| 2015/0238260 A1 | 8/2015 | Nau, Jr. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272657 A1 | 10/2015 | Yates et al. |
| 2015/0272659 A1 | 10/2015 | Boudreaux et al. |
| 2015/0282879 A1 | 10/2015 | Ruelas |
| 2015/0289364 A1 | 10/2015 | Ilkko et al. |
| 2015/0313667 A1 | 11/2015 | Allen, IV |
| 2015/0317899 A1 | 11/2015 | Dumbauld et al. |
| 2015/0351765 A1 | 12/2015 | Valentine et al. |
| 2015/0351857 A1 | 12/2015 | Vander Poorten et al. |
| 2015/0374430 A1 | 12/2015 | Weiler et al. |
| 2015/0374457 A1 | 12/2015 | Colby |
| 2016/0000437 A1 | 1/2016 | Giordano et al. |
| 2016/0038228 A1 | 2/2016 | Daniel et al. |
| 2016/0044841 A1 | 2/2016 | Chamberlain |
| 2016/0045248 A1 | 2/2016 | Unger et al. |
| 2016/0051314 A1 | 2/2016 | Batchelor et al. |
| 2016/0051316 A1 | 2/2016 | Boudreaux |
| 2016/0066913 A1 | 3/2016 | Swayze et al. |
| 2016/0120601 A1 | 5/2016 | Boudreaux et al. |
| 2016/0175025 A1 | 6/2016 | Strobl |
| 2016/0175029 A1 | 6/2016 | Witt et al. |
| 2016/0206342 A1 | 7/2016 | Robertson et al. |
| 2016/0228171 A1 | 8/2016 | Boudreaux |
| 2016/0249910 A1 | 9/2016 | Shelton, IV et al. |
| 2016/0262786 A1 | 9/2016 | Madan et al. |
| 2016/0270841 A1* | 9/2016 | Strobl .............. A61B 18/1233 |
| 2016/0270842 A1 | 9/2016 | Strobl et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0317216 A1 | 11/2016 | Hermes et al. |
| 2016/0331455 A1 | 11/2016 | Hancock et al. |
| 2016/0358849 A1 | 12/2016 | Jur et al. |
| 2017/0020614 A1 | 1/2017 | Jackson et al. |
| 2017/0065331 A1 | 3/2017 | Mayer et al. |
| 2017/0086909 A1 | 3/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0164997 A1 | 6/2017 | Johnson et al. |
| 2017/0189095 A1 | 7/2017 | Danziger et al. |
| 2017/0202595 A1 | 7/2017 | Shelton, IV |
| 2017/0209145 A1 | 7/2017 | Swayze et al. |
| 2017/0224332 A1 | 8/2017 | Hunter et al. |
| 2017/0224405 A1 | 8/2017 | Takashino et al. |
| 2017/0231628 A1 | 8/2017 | Shelton, IV et al. |
| 2017/0281186 A1 | 10/2017 | Shelton, IV et al. |
| 2017/0296169 A1 | 10/2017 | Yates et al. |
| 2017/0296177 A1 | 10/2017 | Harris et al. |
| 2017/0296180 A1 | 10/2017 | Harris et al. |
| 2017/0303954 A1 | 10/2017 | Ishii |
| 2017/0312018 A1 | 11/2017 | Trees et al. |
| 2017/0325874 A1 | 11/2017 | Noack et al. |
| 2017/0333073 A1 | 11/2017 | Faller et al. |
| 2017/0348043 A1 | 12/2017 | Wang et al. |
| 2017/0348044 A1 | 12/2017 | Wang et al. |
| 2017/0367772 A1 | 12/2017 | Gunn et al. |
| 2018/0014872 A1 | 1/2018 | Dickerson |
| 2018/0085157 A1 | 3/2018 | Batchelor et al. |
| 2018/0132850 A1 | 5/2018 | Leimbach et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |

(56) References Cited

U.S. PATENT DOCUMENTS

| | | |
|---|---|---|
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0188125 A1 | 7/2018 | Park et al. |
| 2018/0206904 A1 | 7/2018 | Felder et al. |
| 2018/0221045 A1 | 8/2018 | Zimmerman et al. |
| 2018/0250066 A1 | 9/2018 | Ding et al. |
| 2018/0271578 A1 | 9/2018 | Coulombe |
| 2018/0289432 A1 | 10/2018 | Kostrzewski et al. |
| 2018/0303493 A1 | 10/2018 | Chapolini |
| 2018/0325517 A1 | 11/2018 | Wingardner et al. |
| 2018/0333179 A1 | 11/2018 | Weisenburgh, II et al. |
| 2018/0353245 A1 | 12/2018 | Mccloud et al. |
| 2018/0368844 A1 | 12/2018 | Bakos et al. |
| 2019/0000459 A1 | 1/2019 | Shelton, IV et al. |
| 2019/0000461 A1 | 1/2019 | Shelton, IV et al. |
| 2019/0029746 A1 | 1/2019 | Dudhedia et al. |
| 2019/0038283 A1 | 2/2019 | Shelton, IV et al. |
| 2019/0053818 A1 | 2/2019 | Nelson et al. |
| 2019/0104919 A1 | 4/2019 | Shelton, IV et al. |
| 2019/0117293 A1 | 4/2019 | Kano et al. |
| 2019/0125361 A1 | 5/2019 | Shelton, IV et al. |
| 2019/0125384 A1 | 5/2019 | Scheib et al. |
| 2019/0125390 A1 | 5/2019 | Shelton, IV et al. |
| 2019/0175258 A1 | 6/2019 | Tsuruta |
| 2019/0183504 A1 | 6/2019 | Shelton, IV et al. |
| 2019/0200844 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0200987 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201045 A1 | 7/2019 | Yates et al. |
| 2019/0201048 A1 | 7/2019 | Stulen et al. |
| 2019/0201104 A1 | 7/2019 | Shelton, IV et al. |
| 2019/0201594 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0209201 A1 | 7/2019 | Boudreaux et al. |
| 2019/0223941 A1 | 7/2019 | Kitamura et al. |
| 2019/0269455 A1 | 9/2019 | Mensch et al. |
| 2019/0290265 A1 | 9/2019 | Shelton, IV et al. |
| 2019/0298353 A1 | 10/2019 | Shelton, IV et al. |
| 2019/0366562 A1 | 12/2019 | Zhang et al. |
| 2019/0388091 A1 | 12/2019 | Eschbach et al. |
| 2020/0054321 A1 | 2/2020 | Harris et al. |
| 2020/0078085 A1 | 3/2020 | Yates et al. |
| 2020/0078609 A1 | 3/2020 | Messerly et al. |
| 2020/0100825 A1 | 4/2020 | Henderson et al. |
| 2020/0113622 A1 | 4/2020 | Honegger |
| 2020/0129261 A1 | 4/2020 | Eschbach |
| 2020/0138473 A1 | 5/2020 | Shelton, IV et al. |
| 2020/0188047 A1 | 6/2020 | Itkowitz et al. |
| 2020/0222111 A1 | 7/2020 | Yates et al. |
| 2020/0222112 A1 | 7/2020 | Hancock et al. |
| 2020/0268430 A1 | 8/2020 | Takei et al. |
| 2020/0315623 A1 | 10/2020 | Eisinger et al. |
| 2020/0315712 A1 | 10/2020 | Jasperson et al. |
| 2020/0405302 A1 | 12/2020 | Shelton, IV et al. |
| 2020/0410177 A1 | 12/2020 | Shelton, IV |
| 2021/0100579 A1 | 4/2021 | Shelton, IV et al. |
| 2021/0153927 A1 | 5/2021 | Ross et al. |
| 2021/0177481 A1 | 6/2021 | Shelton, IV et al. |
| 2021/0177494 A1 | 6/2021 | Houser et al. |
| 2021/0177496 A1 | 6/2021 | Shelton, IV et al. |
| 2021/0186492 A1 | 6/2021 | Shelton, IV et al. |
| 2021/0186497 A1 | 6/2021 | Shelton, IV et al. |
| 2021/0186499 A1 | 6/2021 | Shelton, IV et al. |
| 2021/0186501 A1 | 6/2021 | Shelton, IV et al. |
| 2021/0186553 A1 | 6/2021 | Green et al. |
| 2021/0186554 A1 | 6/2021 | Green et al. |
| 2021/0196266 A1 | 7/2021 | Shelton, IV et al. |
| 2021/0196267 A1 | 7/2021 | Shelton, IV et al. |
| 2021/0196269 A1 | 7/2021 | Shelton, IV et al. |
| 2021/0196270 A1 | 7/2021 | Shelton, IV et al. |
| 2021/0196302 A1 | 7/2021 | Shelton, IV et al. |
| 2021/0196305 A1 | 7/2021 | Strobl |
| 2021/0196306 A1 | 7/2021 | Estera et al. |
| 2021/0196307 A1 | 7/2021 | Shelton, IV |
| 2021/0196334 A1 | 7/2021 | Sarley et al. |
| 2021/0196335 A1 | 7/2021 | Messerly et al. |
| 2021/0196336 A1 | 7/2021 | Faller et al. |
| 2021/0196344 A1 | 7/2021 | Shelton, IV et al. |
| 2021/0196345 A1 | 7/2021 | Messerly et al. |
| 2021/0196346 A1 | 7/2021 | Leuck et al. |
| 2021/0196349 A1 | 7/2021 | Fiebig et al. |
| 2021/0196352 A1 | 7/2021 | Messerly et al. |
| 2021/0196353 A1 | 7/2021 | Gee et al. |
| 2021/0196354 A1 | 7/2021 | Shelton, IV et al. |
| 2021/0196357 A1 | 7/2021 | Shelton, IV et al. |
| 2021/0196358 A1 | 7/2021 | Shelton, IV et al. |
| 2021/0196359 A1 | 7/2021 | Shelton, IV et al. |
| 2021/0196361 A1 | 7/2021 | Shelton, IV et al. |
| 2021/0196362 A1 | 7/2021 | Shelton, IV et al. |
| 2021/0196363 A1 | 7/2021 | Shelton, IV et al. |
| 2021/0196364 A1 | 7/2021 | Shelton, IV et al. |
| 2021/0212754 A1 | 7/2021 | Olson |
| 2021/0220036 A1 | 7/2021 | Shelton, IV et al. |
| 2021/0236195 A1 | 8/2021 | Asher et al. |
| 2021/0282804 A1 | 9/2021 | Worrell et al. |
| 2021/0393288 A1 | 12/2021 | Shelton, IV et al. |
| 2021/0393314 A1 | 12/2021 | Wiener et al. |
| 2021/0393319 A1 | 12/2021 | Shelton, IV et al. |
| 2022/0039891 A1 | 2/2022 | Stulen et al. |
| 2022/0071655 A1 | 3/2022 | Price et al. |
| 2022/0167982 A1 | 6/2022 | Shelton, IV et al. |
| 2022/0168005 A1 | 6/2022 | Aldridge et al. |
| 2022/0168039 A1 | 6/2022 | Worrell et al. |
| 2022/0304736 A1 | 9/2022 | Boudreaux |
| 2022/0313297 A1 | 10/2022 | Aldridge et al. |
| 2022/0346863 A1 | 11/2022 | Yates et al. |
| 2022/0387067 A1 | 12/2022 | Faller et al. |
| 2022/0406452 A1 | 12/2022 | Shelton, IV |
| 2023/0038162 A1 | 2/2023 | Timm et al. |
| 2023/0048996 A1 | 2/2023 | Vakharia et al. |
| 2023/0270486 A1 | 8/2023 | Wiener et al. |
| 2023/0277205 A1 | 9/2023 | Olson et al. |
| 2023/0372743 A1 | 11/2023 | Wiener et al. |
| 2023/0380880 A1 | 11/2023 | Wiener et al. |

FOREIGN PATENT DOCUMENTS

| | | |
|---|---|---|
| CN | 1634601 A | 7/2005 |
| CN | 1775323 A | 5/2006 |
| CN | 1922563 A | 2/2007 |
| CN | 2868227 Y | 2/2007 |
| CN | 201029899 Y | 3/2008 |
| CN | 101474081 A | 7/2009 |
| CN | 101516285 A | 8/2009 |
| CN | 101522112 A | 9/2009 |
| CN | 102100582 A | 6/2011 |
| CN | 102149312 A | 8/2011 |
| CN | 202027624 U | 11/2011 |
| CN | 102792181 A | 11/2012 |
| CN | 103281982 A | 9/2013 |
| CN | 103379853 A | 10/2013 |
| CN | 203468630 U | 3/2014 |
| CN | 104001276 A | 8/2014 |
| CN | 104013444 A | 9/2014 |
| CN | 104434298 A | 3/2015 |
| CN | 107374752 A | 11/2017 |
| DE | 3904558 A1 | 8/1990 |
| DE | 9210327 U1 | 11/1992 |
| DE | 4300307 A1 | 7/1994 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| DE | 102012109037 A1 | 4/2014 |
| EP | 0171967 A2 | 2/1986 |
| EP | 0336742 A2 | 10/1989 |

(56) References Cited

FOREIGN PATENT DOCUMENTS

| | | |
|---|---|---|
| EP | 0136855 B1 | 11/1989 |
| EP | 0705571 A1 | 4/1996 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 2510891 A1 | 10/2012 |
| EP | 1767164 B1 | 1/2013 |
| EP | 2578172 A2 | 4/2013 |
| EP | 2668922 A1 | 12/2013 |
| EP | 2076195 B1 | 12/2015 |
| EP | 3476302 A2 | 5/2019 |
| EP | 3476331 A1 | 5/2019 |
| EP | 3694298 A1 | 8/2020 |
| GB | 2032221 A | 4/1980 |
| GB | 2317566 A | 4/1998 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H 0541716 A | 2/1993 |
| JP | H0576482 A | 3/1993 |
| JP | H0595955 A | 4/1993 |
| JP | H05115490 A | 5/1993 |
| JP | H0670938 A | 3/1994 |
| JP | H06104503 A | 4/1994 |
| JP | H0824266 A | 1/1996 |
| JP | H08229050 A | 9/1996 |
| JP | H08275951 A | 10/1996 |
| JP | H08299351 A | 11/1996 |
| JP | H08336545 A | 12/1996 |
| JP | H09130655 A | 5/1997 |
| JP | H09135553 A | 5/1997 |
| JP | H09140722 A | 6/1997 |
| JP | H105237 A | 1/1998 |
| JP | 10127654 A | 5/1998 |
| JP | H10295700 A | 11/1998 |
| JP | H11128238 A | 5/1999 |
| JP | H11169381 A | 6/1999 |
| JP | 2000210299 A | 8/2000 |
| JP | 2000271142 A | 10/2000 |
| JP | 2000271145 A | 10/2000 |
| JP | 2000287987 A | 10/2000 |
| JP | 2001029353 A | 2/2001 |
| JP | 2002059380 A | 2/2002 |
| JP | 2002186901 A | 7/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003339730 A | 12/2003 |
| JP | 2004129871 A | 4/2004 |
| JP | 2004147701 A | 5/2004 |
| JP | 2005003496 A | 1/2005 |
| JP | 2005027026 A | 1/2005 |
| JP | 2005074088 A | 3/2005 |
| JP | 2005337119 A | 12/2005 |
| JP | 2006068396 A | 3/2006 |
| JP | 2006081664 A | 3/2006 |
| JP | 2006114072 A | 4/2006 |
| JP | 2006217716 A | 8/2006 |
| JP | 2006288431 A | 10/2006 |
| JP | 2007037568 A | 2/2007 |
| JP | 200801876 A | 1/2008 |
| JP | 2008017876 A | 1/2008 |
| JP | 200833644 A | 2/2008 |
| JP | 2008188160 A | 8/2008 |
| JP | D1339835 S | 8/2008 |
| JP | 2010009686 A | 1/2010 |
| JP | 2010121865 A | 6/2010 |
| JP | 2012071186 A | 4/2012 |
| JP | 2012223582 A | 11/2012 |
| JP | 2012235658 A | 11/2012 |
| JP | 2013126430 A | 6/2013 |
| KR | 100789356 B1 | 12/2007 |
| KR | 101298237 B1 | 8/2013 |
| RU | 2154437 C1 | 8/2000 |
| RU | 22035 U1 | 3/2002 |
| RU | 2201169 C2 | 3/2003 |
| RU | 2405603 C1 | 12/2010 |
| RU | 2013119977 A | 11/2014 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9712557 A1 | 4/1997 |
| WO | WO-9800069 A1 | 1/1998 |
| WO | WO-9840015 A2 | 9/1998 |
| WO | WO-9920213 A1 | 4/1999 |
| WO | WO-9923960 A1 | 5/1999 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0172251 A1 | 10/2001 |
| WO | WO-0195810 A2 | 12/2001 |
| WO | WO-02080793 A1 | 10/2002 |
| WO | WO-03095028 A1 | 11/2003 |
| WO | WO-2004037095 A2 | 5/2004 |
| WO | WO-2004078051 A2 | 9/2004 |
| WO | WO-2004098426 A1 | 11/2004 |
| WO | WO-2006091494 A1 | 8/2006 |
| WO | WO-2007008710 A2 | 1/2007 |
| WO | WO-2008118709 A1 | 10/2008 |
| WO | WO-2008130793 A1 | 10/2008 |
| WO | WO-2010027109 A1 | 3/2010 |
| WO | WO-2010104755 A1 | 9/2010 |
| WO | WO-2011008672 A2 | 1/2011 |
| WO | WO-2011044343 A2 | 4/2011 |
| WO | WO-2011052939 A2 | 5/2011 |
| WO | WO-2011060031 A1 | 5/2011 |
| WO | WO-2011092464 A1 | 8/2011 |
| WO | WO-2012044606 A2 | 4/2012 |
| WO | WO-2012061722 A2 | 5/2012 |
| WO | WO-2012088535 A1 | 6/2012 |
| WO | WO-2012150567 A1 | 11/2012 |
| WO | WO-2016130844 A1 | 8/2016 |
| WO | WO-2019130090 A1 | 7/2019 |
| WO | WO-2019130113 A1 | 7/2019 |

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

AST Products, Inc., "Principles of Video Contact Angle Analysis," 20 pages, (2006).

(56) References Cited

OTHER PUBLICATIONS

Campbell et al., "Thermal Imaging in Surgery," p. 19-3, in Medical Infrared Imaging, N. A. Diakides and J. D. Bronzino, Eds. (2008).
Chen et al, "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Heat-induced changes in the mechanics of a collagenous tissue: pseudoelastic behavior at 37° C," Journal of Biomechanics, 31, pp. 211-216 (1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Covidien 501(k) Summary Sonicision, dated Feb. 24, 2011 (7 pages).
Covidien Brochure, [Value Analysis Brief], LigaSure Advance™ Pistol Grip, dated Rev. Apr. 2010 (7 pages).
Covidien Brochure, LigaSure Atlas™ Hand Switching Instruments, dated Dec. 2008 (2 pages).
Covidien Brochure, LigaSure Impact™ Instrument LF4318, dated Feb. 2013 (3 pages).
Covidien Brochure, The LigaSure Precise™ Instrument, dated Mar. 2011 (2 pages).
Covidien Brochure, The LigaSure™ 5 mm Blunt Tip Sealer/Divider Family, dated Apr. 2013 (2 pages).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
Douglas, S.C. "Introduction to Adaptive Filter". Digital Signal Processing Handbook. Ed. Vijay K. Madisetti and Douglas B. Williams. Boca Raton: CRC Press LLC, 1999.
Erbe Electrosurgery VIO® 200 S, (2012), p. 7, 12 pages, accessed Mar. 31, 2014 at http://www. erbe-med. com/erbe/media/Marketing materialien/85140170 ERBE EN VIO 200 S D027541.
F. A. Duck, "Optical Properties of Tissue Including Ultraviolet and Infrared Radiation," pp. 43-71 in Physical Properties of Tissue (1990).
Fowler, K.R., "A Programmable, Arbitrary Waveform Electrosurgical Device," IEEE Engineering in Medicine and Biology Society 10th Annual International Conference, pp. 1324, 1325 (1988).
Gerhard, Glen C., "Surgical Electrotechnology: Quo Vadis?," IEEE Transactions on Biomedical Engineering, vol. BME-31, No. 12, pp. 787-792, Dec. 1984.
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Glaser and Subak-Sharpe, Integrated Circuit Engineering, Addison-Wesley Publishing, Reading, MA (1979). (book—not attached).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Graff, K.F., "Elastic Wave Propagation in a Curved Sonic Transmission Line, " IEEE Transactions on Sonics and Ultrasonics, SU-17(1), 1-6 (1970).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Henriques. F.C., "Studies in thermal injury V. The predictability and the significance of thermally induced rate processes leading to irreversible epidermal injury." Archives of Pathology, 434, pp. 489-502 (1947).
http://www.4-traders.com/JOHNSON-JOHNSON-4832/news/Johnson-Johnson-Ethicon-E . . . .
http://www.apicalinstr.com/generators.htm.
http://www.dotmed.com/listing/electrosurical-unit/ethicon/ultracision-g110-/1466724.
http://www.medicalexpo.com/medical-manufacturer/electrosurgical-generator-6951.html.
http://www.megadyne.com/es_generator.php.
http://www.valleylab.com/product/es/generators/index.html.
http:/www.ethicon.com/gb-en/healthcare-professionals/products/energy-devices/capital//ge . . . .
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Humphrey, J.D., "Continuum Thermomechanics and the Clinical Treatment of Disease and Injury," Appl. Mech. Rev., vol. 56, No. 2 pp. 231-260 (Mar. 2003).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Hörmann et al., "Reversible and irreversible denaturation of collagen fibers." Biochemistry, 10, pp. 932-937 (1971).
IEEE Std 802.3-2012 (Revision of IEEE Std 802.3-2008, published Dec. 28, 2012.
Incropera et al., Fundamentals of Heat and Mass Transfer, Wiley, New York (1990). (Book—not attached).
Jang, J. et al. "Neuro-fuzzy and Soft Computing." Prentice Hall, 1997, pp. 13-89, 199-293, 335-393, 453-496, 535-549.
Kurt Gieck & Reiner Gieck, *Engineering Formulas* § Z.7 (7th ed. 1997).
Lacourse, J.R.; Vogt, M.C .; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Lee et al., "A multi-sample denaturation temperature tester for collagenous biomaterials," Med. Eng. Phy., vol. 17, No. 2, pp. 115-121 (Mar. 1995).
Leonard I. Malis, M.D., "The Value of Irrigation During Bipolar Coagulation," 1989.
Lim et al., "A Review of Mechanism Used in Laparoscopic Surgical Instruments," Mechanism and Machine Theory, vol. 38, pp. 1133-1147, (2003).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Missinne, et al. "Stretchable Optical Waveguides," vol. 22, No. 4, Feb. 18, 2014, pp. 4168-4179 (12 pages).
Moraleda et al., A Temperature Sensor Based on a Polymer Optical Fiber Macro-Bend, Sensors 2013, 13, 13076-13089, doi: 10.3390/s131013076, ISSN 1424-8220.
Moran et al., "Thermally Induced Shrinkage of Joint Capsule," Clinical Orthopaedics and Related Research, No. 281, pp. 248-255 (Dec. 2000).
Morley, L. S. D., "Elastic Waves in a Naturally Curved Rod," Quarterly Journal of Mechanics and Applied Mathematics, 14: 155-172 (1961).
National Semiconductors Temperature Sensor Handbook—http://www.national.com/appinfo/tempsensors/files/temphb.pdf; accessed online: Apr. 1, 2011.
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

(56) References Cited

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Technology Overview, printed from www.harmonicscalpel.com, Internet site, website accessed on Jun. 13, 2007, (3 pages).
Wall et al., "Thermal modification of collagen," J Shoulder Elbow Surg, No. 8, pp. 339-344 (Jul./Aug. 1999).
Walsh, S. J., White, R. G., "Vibrational Power Transmission in Curved Beams," Journal of Sound and Vibration, 233(3), 455-488 (2000).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Wright, et al., "Time-Temperature Equivalence of Heat-Induced Changes in Cells and Proteins," Feb. 1998. ASME Journal of Biomechanical Engineering, vol. 120, pp. 22-26.

\* cited by examiner

END EFFECTOR CONTROL AND CALIBRATION

CROSS REFERENCE TO RELATED APPLICATION

This application is a continuation application claiming priority under 35 U.S.C. § 120 to U.S. patent application Ser. No. 15/363,244, entitled END EFFECTOR CONTROL AND CALIBRATION, filed on Nov. 29, 2016, which issued on Mar. 8, 2022 as U.S. Pat. No. 11,266,430, the entire disclosure of which is hereby incorporated by reference herein.

TECHNICAL FIELD

The technical field may generally relate to controlling surgical instruments, and in particular, controlling and calibrating end effectors of surgical instruments.

BACKGROUND

Various aspects are directed to surgical instruments, and controlling and calibrating end effectors of surgical instruments.

For example, ultrasonic surgical devices are finding increasingly widespread applications in surgical procedures by virtue of their unique performance characteristics. Depending upon specific device configurations and operational parameters, ultrasonic surgical devices can provide substantially simultaneous transection of tissue and homeostasis by coagulation, desirably minimizing patient trauma. An ultrasonic surgical device may comprise a handpiece containing an ultrasonic transducer, and an instrument coupled to the ultrasonic transducer having a distally mounted end effector (e.g., an ultrasonic blade and a clamp arm, where the clamp arm may comprise a non-stick tissue pad) to cut and seal tissue. In some cases, the instrument may be permanently affixed to the handpiece. In other cases, the instrument may be detachable from the handpiece, as in the case of a disposable instrument or an instrument that is interchangeable between different handpieces. The end effector transmits ultrasonic energy to tissue brought into contact with the end effector to realize cutting and sealing action. Ultrasonic surgical devices of this nature can be configured for open surgical use, laparoscopic, or endoscopic surgical procedures including robotic-assisted procedures.

Ultrasonic energy cuts and coagulates tissue using temperatures lower than those used in electro surgical procedures. Vibrating at high frequencies (e.g., 55,500 times per second), the ultrasonic blade denatures protein in the tissue to form a sticky coagulum. Pressure exerted on tissue by the ultrasonic blade surface collapses blood vessels and allows the coagulum to form a hemostatic seal. A surgeon can control the cutting speed and coagulation by the force applied to the tissue by the end effector, the time over which the force is applied and the selected excursion level of the end effector.

SUMMARY

In one aspect, a method for controlling an end effector may include detecting a signal in response to movement of a first tube relative to a second tube, the first tube driving movement of a clamp arm of the end effector. The method may also include determining a clamp arm position of the end effector relative to a ultrasonic blade of the end effector based on the signal. The method may additionally include adjusting a power output to the ultrasonic blade of the end effector based on the clamp arm position.

One or more of the following features may be included. The first tube may be an inner tube and the second tube may be an outer tube, the inner tube being moveable relative to the outer tube, the outer tube being static relative to the inner tube. The method may further include detecting the signal using a Hall-effect sensor and a magnet positioned on the first tube. The method may also include moving a magnet positioned on the first tube relative to a Hall-effect sensor as the first tube drives movement of the clamp arm of the end effector. The method may additionally include adjusting the power output to the ultrasonic blade of the end effector using an ultrasonic transducer based on a voltage change in a Hall-effect sensor. Moreover, the method may include adjusting the power output to the ultrasonic blade of the end effector dynamically, based on a travel ratio that changes as the clamp arm approaches the ultrasonic blade. Furthermore, the method may include adjusting the power output to the ultrasonic blade of the end effector dynamically, using a proportional-integral controller, based on a travel ratio that changes as the clamp arm approaches the ultrasonic blade.

In one or more implementations, the method may include determining a type of tissue between the clamp arm and the ultrasonic blade based on the signal. The method may also include adjusting the power output to the ultrasonic blade of the end effector based on the type of tissue. The method may additionally include, in response to determining that the type of tissue between the clamp and the ultrasonic blade is a small vessel, reducing the power output to the ultrasonic blade of the end effector by an amount less than for a large vessel. Moreover, the method may include in response to determining that the type of tissue between the clamp and the ultrasonic blade is a large vessel, reducing the power output to the ultrasonic blade of the end effector by an amount more than for a small vessel.

In one aspect, an apparatus for controlling an end effector may include a sensor configured to detect a signal in response to movement of a first tube relative to a second tube, the first tube driving movement of a clamp arm of the end effector. The apparatus may also include a processor configured to determine a clamp arm position of the end effector relative to a ultrasonic blade of the end effector based on the signal. The apparatus may further include a transducer configured to adjust a power output to the ultrasonic blade of the end effector based on the clamp arm position.

One or more of the following features may be included. The first tube may be an inner tube and the second tube may be an outer tube, the inner tube being moveable relative to the outer tube, the outer tube being static relative to the inner tube. The apparatus may further include a magnet positioned on the first tube wherein the sensor is a Hall-effect sensor used to detect the signal based on a position of the magnet. The magnet may be positioned on the first tube moves relative to a Hall-effect sensor as the first tube drives movement of the clamp arm of the end effector. The transducer may be an ultrasonic transducer configured to adjust the power output to the ultrasonic blade of the end effector based on a voltage change in a Hall-effect sensor. The apparatus may also include a proportional-integral controller configured to adjust the power output to the ultrasonic blade of the end effector dynamically, based on a travel ratio that changes as the clamp arm approaches the ultrasonic blade.

In one aspect, a method for calibrating an apparatus for controlling an end effector may include detecting a first signal corresponding to a fully open position of a clamp arm and a ultrasonic blade of the end effector. The method may also include detecting a second signal corresponding to an intermediate position of the clamp arm and the ultrasonic blade of the end effector, the intermediate position resulting from clamping a rigid body between the clamp arm and the ultrasonic blade. The method may additionally include detecting a third signal corresponding to a fully closed position of the clamp arm and the ultrasonic blade of the end effector. The method may further include determining a best fit curve to represent signal strength as a function of sensor displacement based on at least the first, second, and third signals, the fully open, intermediate, and fully closed positions, and a dimension of the rigid body. Moreover, the method may include creating a lookup table based on at least the first, second, and third signals, and the fully open, intermediate, and fully closed positions.

In one aspect, an apparatus for controlling an end effector comprising a clamp arm is disclosed. The apparatus includes a sensor configured to generate signals in response to movement of a first tube relative to a second tube, the first tube driving movement of the clamp arm of the end effector; and a control circuit configured to receive a first signal, a second signal, and a third signal from the sensor, generate a fit curve based on the first signal, the second signal, and the third signal, receive a fourth signal from the sensor, and generate a conclusion associated with a relative position of the clamp arm based on the fourth signal and the generated fit curve. The first signal, the second signal, and the third signal are associated with positions of the clamp arm of the end effector as it moves. The fourth signal is associated with a current position of the clamp arm of the end effector as it moves.

In one aspect, an apparatus for controlling an end effector comprising a clamp arm and an ultrasonic blade is disclosed. The apparatus comprises a sensor configured to generate signals in response to movement of a first tube relative to a second tube, the first tube driving movement of the clamp arm of the end effector, and a control circuit configured to receive a first signal, a second signal, and a third signal from the sensor, generate a fit curve based on the first signal, the second signal, and the third signal, receive a fourth signal from the sensor, generate a conclusion associated with a relative position of the clamp arm based on the fourth signal and the generated fit curve, determine an impedance of the ultrasonic blade in contact with tissue, and determine a type of the tissue based on the impedance. The first signal, the second signal, and the third signal are associated with positions of the clamp arm of the end effector as it moves. The fourth signal is associated with a current position of the clamp arm of the end effector as it moves.

In one aspect, a computer-implemented method of controlling an end effector comprising a clamp arm and an ultrasonic blade is disclosed. The method includes receiving, via a control circuit, a first signal, a second signal, and a third signal from a sensor configured to generate signals in response to movement of a first tube of the end effector relative to a second tube of the end effector, the first tube driving movement of the clamp arm of the end effector, generating, via the control circuit, a fit curve based on the first signal, the second signal, and the third signal, receiving, via the control circuit, a fourth signal from the sensor, generating, via the control circuit, a conclusion associated with a relative position of the clamp arm based on the fourth signal and the generated fit curve, determining, via the control circuit, a thickness of a tissue based on the generated conclusion, determining, via the control circuit, an impedance of the ultrasonic blade in contact with the tissue, and determining, via the control circuit, a type of the tissue based on the impedance. The first signal, the second signal, and the third signal are associated with positions of the clamp arm of the end effector as it moves. The fourth signal is associated with a current position of the clamp arm of the end effector as it moves.

The details of one or more implementations are set forth in the accompanying drawings and the description below. Other features and advantages will become apparent from the description, the drawings, and the claims.

BRIEF DESCRIPTION OF THE DRAWINGS

FIG. 25 illustrates an end effector in a fully open configuration to record a first data point (1) in accordance with one aspect of the present disclosure;

FIG. 26 illustrates an end effector in a second intermediate configuration grasping a first gage pin of a known diameter to record a second data point (2) in accordance with one aspect of the present disclosure;

FIG. 27 illustrates an end effector in a third intermediate configuration grasping a second gage pin of a known diameter to record a third data point (3) in accordance with one aspect of the present disclosure; and FIG. 28 illustrates an end effector in a fully closed configuration to record a fourth data point (4) in accordance with one aspect of the present disclosure;

FIG. 29A is a schematic diagram of surgical instrument configured to seal small and large vessels in accordance with one aspect of the present disclosure;

FIG. 29B is a diagram of an example range of a small vessel and a large vessel and the relative position of a clamp arm of the end effector in accordance with one aspect of the present disclosure;

FIG. 29C is a graph that depicts a process for sealing small vessels by applying various ultrasonic energy levels for a different periods of time in accordance with one aspect of the present disclosure; and FIG. 29D is a graph that depicts a process for sealing large vessels by applying various ultrasonic energy levels for different periods of time in accordance with one aspect of the present disclosure;

DESCRIPTION

Various aspects described herein are directed to surgical instruments comprising distally positioned, articulatable jaw assemblies. The jaw assemblies may be utilized in lieu of or in addition to shaft articulation. For example, the jaw assemblies may be utilized to grasp tissue and move it towards an ultrasonic blade, RF electrodes or other component for treating tissue.

In one aspect, a surgical instrument may comprise an end effector with an ultrasonic blade extending distally therefrom. The jaw assembly may be articulatable and may pivot about at least two axes. A first axis, or wrist pivot axis, may be substantially perpendicular to a longitudinal axis of the instrument shaft. The jaw assembly may pivot about the wrist pivot axis from a first position where the jaw assembly is substantially parallel to the ultrasonic blade to a second position where the jaw assembly is not substantially parallel to the ultrasonic blade. In addition, the jaw assembly may comprise first and second jaw members that are pivotable about a second axis or jaw pivot axis. The jaw pivot axis may be substantially perpendicular to the wrist pivot axis. In some aspects, the jaw pivot axis itself may pivot as the jaw assembly pivots about the wrist pivot axis. The first and second jaw members may be pivotably relative to one another about the jaw pivot axis such that the first and second jaw members may "open" and "close." Additionally, in some aspects, the first and second jaw members are also pivotable about the jaw pivot axis together such that the direction of the first and second jaw members may change.

Reference will now be made in detail to several aspects, including aspects showing example implementations of manual and robotic surgical instruments with end effectors comprising ultrasonic and/or electro surgical elements. Wherever practicable similar or like reference numbers may be used in the figures and may indicate similar or like functionality. The figures depict example aspects of the disclosed surgical instruments and/or methods of use for purposes of illustration only. One skilled in the art will readily recognize from the following description that alternative example aspects of the structures and methods illustrated herein may be employed without departing from the principles described herein.

Figure 1:
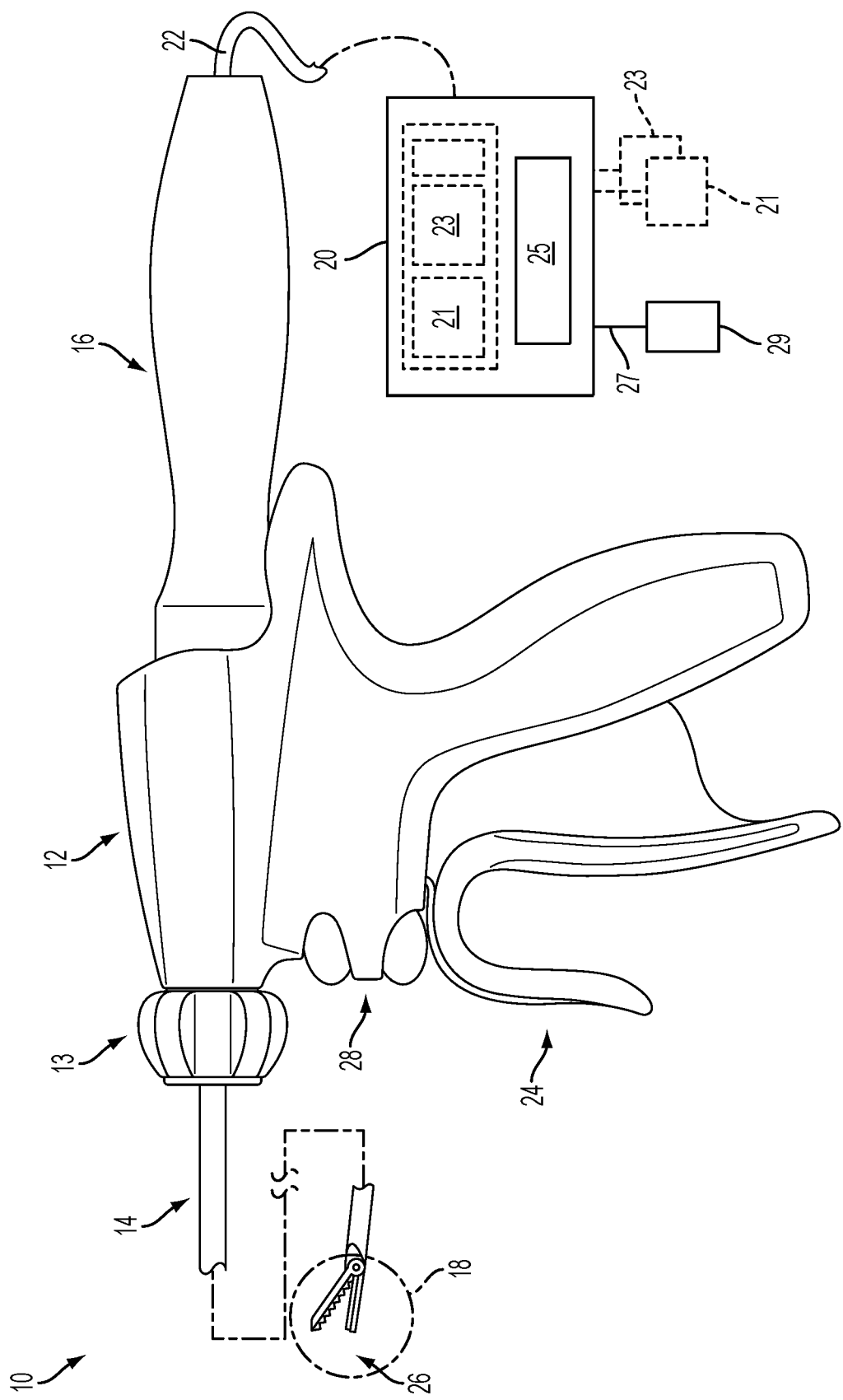
FIG. 1 is an elevation view of an example surgical instrument in accordance with one aspect of the present disclosure

FIG. 1 is a right side view of one aspect of an ultrasonic surgical instrument 10. In the illustrated aspect, the ultrasonic surgical instrument 10 may be employed in various surgical procedures including endoscopic or traditional open surgical procedures. In one aspect, the ultrasonic surgical instrument 10 comprises a handle assembly 12, an elongated shaft assembly 14, and an ultrasonic transducer 16. The handle assembly 12 comprises a trigger assembly 24, a distal rotation assembly 13, and a switch assembly 28. The elongated shaft assembly 14 comprises an end effector assembly 26, which comprises elements to dissect tissue or mutually grasp, cut, and coagulate vessels and/or tissue, and actuating elements to actuate the end effector assembly 26. The handle assembly 12 is adapted to receive the ultrasonic transducer 16 at the proximal end. The ultrasonic transducer 16 is mechanically engaged to the elongated shaft assembly 14 and portions of the end effector assembly 26. The ultrasonic transducer 16 is electrically coupled to a generator 20 via a cable 22. Although the majority of the drawings depict a multiple end effector assembly 26 for use in connection with laparoscopic surgical procedures, the ultrasonic surgical instrument 10 may be employed in more traditional open surgical procedures and in other aspects, may be configured for use in endoscopic procedures. For the purposes herein, the ultrasonic surgical instrument 10 is described in terms of an endoscopic instrument; however, it is contemplated that an open and/or laparoscopic version of the ultrasonic surgical instrument 10 also may include the same or similar operating components and features as described herein.

In various aspects, the generator 20 comprises several functional elements, such as modules and/or blocks. Different functional elements or modules may be configured for driving different kinds of surgical devices. For example, an ultrasonic generator module 21 may drive an ultrasonic device, such as the ultrasonic surgical instrument 10. In some example aspects, the generator 20 also comprises an electrosurgery/RF generator module 23 for driving an electrosurgical device (or an electro surgical aspect of the ultrasonic surgical instrument 10). In the example aspect illustrated in FIG. 1, the generator 20 includes a control system 25 integral with the generator 20, and a foot switch 29 connected to the generator via a cable 27. The generator 20 may also comprise a triggering mechanism for activating a surgical instrument, such as the instrument 10. The triggering mechanism may include a power switch (not shown) as well as a foot switch 29. When activated by the foot switch 29, the generator 20 may provide energy to drive the acoustic assembly of the surgical instrument 10 and to drive the end effector 18 at a predetermined excursion level. The generator 20 drives or excites the acoustic assembly at any suitable resonant frequency of the acoustic assembly and/or derives the therapeutic/sub-therapeutic electromagnetic/RF energy. In one aspect, the electrosurgical/RF generator module 23 may be implemented as an electrosurgery unit (ESU) capable of supplying power sufficient to perform bipolar electrosurgery using radio frequency (RF) energy. In one aspect, the ESU can be a bipolar ERBE ICC 350 sold by ERBE USA, Inc. of Marietta, Ga. In bipolar electrosurgery applications, as previously discussed, a surgical instrument having an active electrode and a return electrode can be utilized, wherein the active electrode and the return electrode can be positioned against, or adjacent to, the tissue to be treated such that current can flow from the active electrode to the return electrode through the tissue. Accordingly, the electrosurgical/RF module 23 generator may be configured for therapeutic purposes by applying electrical energy to the tissue T sufficient for treating the tissue (e.g., cauterization). For example, in some aspects, the active and/or return electrode may be positioned on the jaw assembly described herein.

In one aspect, the electrosurgical/RF generator module 23 may be configured to deliver a subtherapeutic RF signal to implement a tissue impedance measurement module. In one aspect, the electrosurgical/RF generator module 23 comprises a bipolar radio frequency generator. In one aspect, the electrosurgical/RF generator module 23 may be configured to monitor electrical impedance Z, of tissue T and to control the characteristics of time and power level based on the tissue T by way of a return electrode provided on a clamp member of the end effector assembly 26. Accordingly, the electrosurgical/RF generator module 23 may be configured for subtherapeutic purposes for measuring the impedance or other electrical characteristics of the tissue T. Techniques and circuit configurations for measuring the impedance or other electrical characteristics of tissue T are discussed in more detail in commonly assigned U.S. Patent Publication No. 2011/0015631, titled "Electrosurgical Generator for Ultrasonic Surgical Instrument," the disclosure of which is herein incorporated by reference in its entirety.

A suitable ultrasonic generator module 21 may be configured to functionally operate in a manner similar to the GEN300 sold by Ethicon Endo-Surgery, Inc. of Cincinnati, Ohio as is disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting a Loose Blade in a Hand Piece Connected to an Ultrasonic Surgical System); U.S. Pat. No. 6,662,127 (Method for Detecting Presence of a Blade in an Ultrasonic System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Ultrasonic Blade Resonance Frequency at Startup); and U.S. Pat. No. 7,273,483 (Apparatus and Method for Alerting Generator Function in an Ultrasonic Surgical System).

It will be appreciated that in various aspects, the generator 20 may be configured to operate in several modes. In one mode, the generator 20 may be configured such that the ultrasonic generator module 21 and the electrosurgical/RF generator module 23 may be operated independently.

For example, the ultrasonic generator module 21 may be activated to apply ultrasonic energy to the end effector assembly 26 and subsequently, either therapeutic sub-therapeutic RF energy may be applied to the end effector assembly 26 by the electrosurgical/RF generator module 23. As previously discussed, the sub-therapeutic electrosurgical/RF energy may be applied to tissue clamped between claim elements of the end effector assembly 26 to measure tissue impedance to control the activation, or modify the activation, of the ultrasonic generator module 21. Tissue impedance feedback from the application of the sub-therapeutic energy also may be employed to activate a therapeutic level of the electrosurgical/RF generator module 23 to seal the tissue (e.g., vessel) clamped between claim elements of the end effector assembly 26.

In another aspect, the ultrasonic generator module 21 and the electrosurgical/RF generator module 23 may be activated simultaneously. In one example, the ultrasonic generator module 21 is simultaneously activated with a sub-therapeutic RF energy level to measure tissue impedance simultaneously while the ultrasonic blade of the end effector assembly 26 cuts and coagulates the tissue (or vessel) clamped between the clamp elements of the end effector assembly 26. Such feedback may be employed, for example, to modify the drive output of the ultrasonic generator module 21. In another example, the ultrasonic generator module 21 may be driven simultaneously with electrosurgical/RF generator module 23 such that the ultrasonic blade portion of the end effector assembly 26 is employed for cutting the damaged tissue while the electrosurgical/RF energy is applied to electrode portions of the end effector clamp assembly 26 for sealing the tissue (or vessel).

When the generator 20 is activated via the triggering mechanism, electrical energy is continuously applied by the generator 20 to a transducer stack or assembly of the acoustic assembly. In another aspect, electrical energy is intermittently applied (e.g., pulsed) by the generator 20. A phaselocked loop in the control system of the generator 20 may monitor feedback from the acoustic assembly. The phase lock loop adjusts the frequency of the electrical energy sent by the generator 20 to match the resonant frequency of the selected longitudinal mode of vibration of the acoustic assembly. In addition, a second feedback loop in the control system 25 maintains the electrical current supplied to the acoustic assembly at a pre-selected constant level in order to achieve substantially constant excursion at the end effector 18 of the acoustic assembly. In yet another aspect, a third feedback loop in the control system 25 monitors impedance between electrodes located in the end effector assembly 26. Although FIGS. 1-5 show a manually operated ultrasonic surgical instrument, it will be appreciated that ultrasonic surgical instruments may also be used in robotic applications, for example, as described herein as well as combinations of manual and robotic applications.

In ultrasonic operation mode, the electrical signal supplied to the acoustic assembly may cause the distal end of the end effector 18, to vibrate longitudinally in the range of, for example, approximately 20 kHz to 250 kHz. According to various aspects, the ultrasonic blade 22 may vibrate in the range of about 54 kHz to 56 kHz, for example, at about 55.5 kHz. In other aspects, the ultrasonic blade 22 may vibrate at other frequencies including, for example, about 31 kHz or about 80 kHz. The excursion of the vibrations at the ultrasonic blade can be controlled by, for example, controlling the amplitude of the electrical signal applied to the transducer assembly of the acoustic assembly by the generator 20. As noted above, the triggering mechanism of the generator 20 allows a user to activate the generator 20 so that electrical energy may be continuously or intermittently supplied to the acoustic assembly. The generator 20 also has a power line for insertion in an electro-surgical unit or conventional electrical outlet. It is contemplated that the generator 20 can also be powered by a direct current (DC) source, such as a battery. The generator 20 can comprise any suitable generator, such as Model No. GEN04, and/or Model No. GEN11 available from Ethicon Endo-Surgery, Inc.

Figure 2:
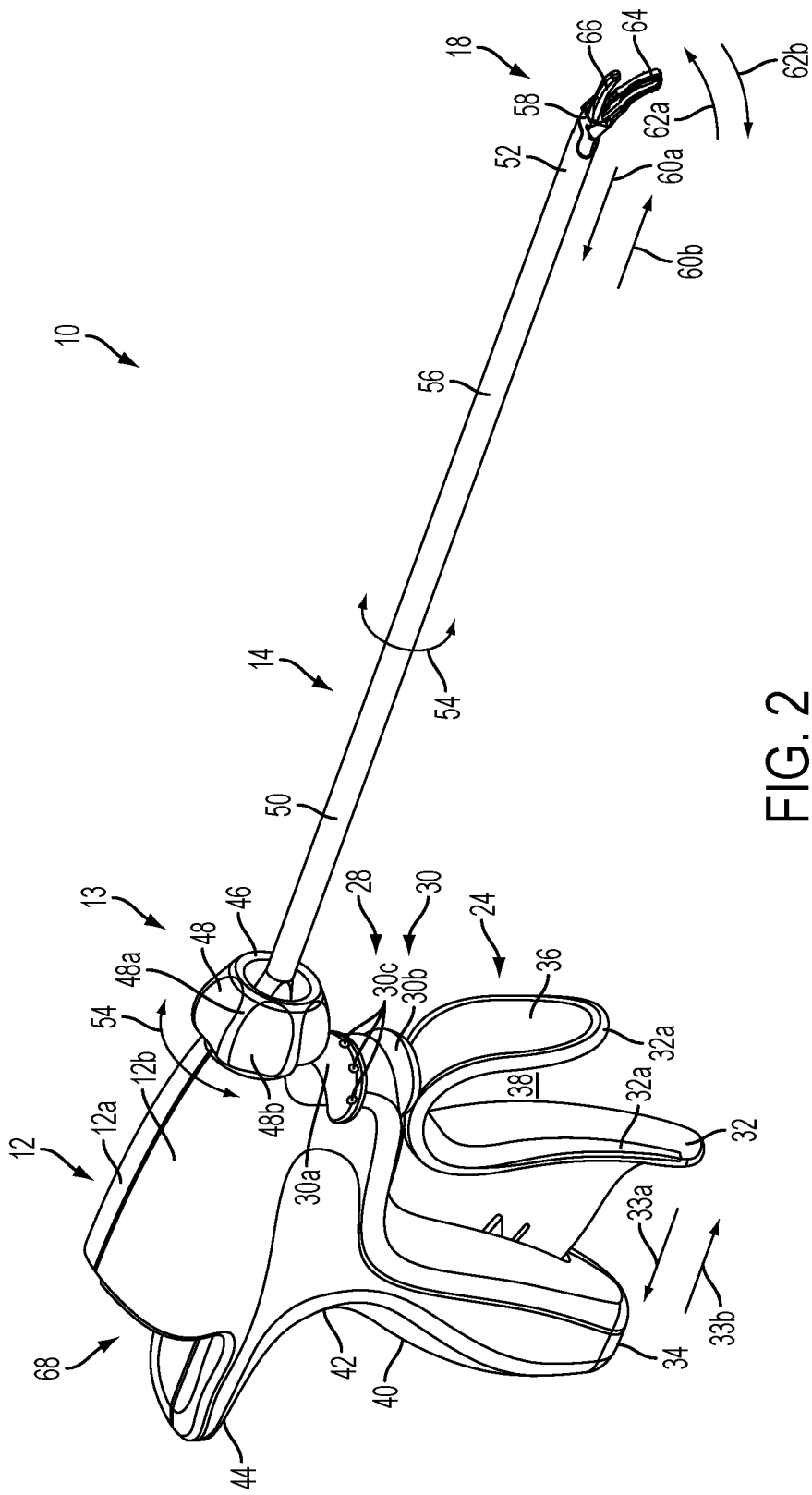
FIG. 2 is a perspective view of an example surgical instrument in accordance with one aspect of the present disclosure.
Figure 3:
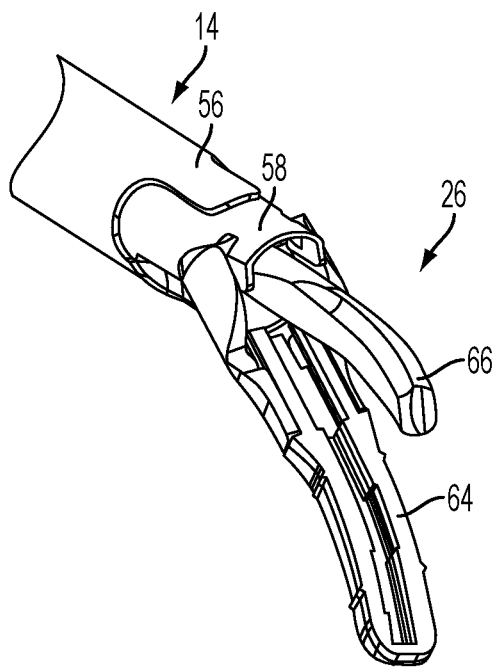
FIG. 3 illustrates an example end effector of a surgical instruments in accordance with one aspect of the present disclosure.

FIG. 2 is a left perspective view of one example aspect of the ultrasonic surgical instrument 10 showing the handle assembly 12, the distal rotation assembly 13, and the elongated shaft assembly 14. FIG. 3 shows the end effector assembly 26. In the illustrated aspect the elongated shaft assembly 14 comprises a distal end 52 dimensioned to mechanically engage the end effector assembly 26 and a proximal end 50 that mechanically engages the handle assembly 12 and the distal rotation assembly 13. The proximal end 50 of the elongated shaft assembly 14 is received within the handle assembly 12 and the distal rotation assembly 13. More details relating to the connections between the elongated shaft assembly 14, the handle assembly 12, and the distal rotation assembly 13 are provided in the description of FIG. 5. In the illustrated aspect, the trigger assembly 24 comprises a trigger 32 that operates in conjunction with a fixed handle 34. The fixed handle 34 and the trigger 32 are ergonomically formed and adapted to interface comfortably with the user. The fixed handle 34 is integrally associated with the handle assembly 12. The trigger 32 is pivotally movable relative to the fixed handle 34 as explained in more detail below with respect to the operation of the ultrasonic surgical instrument 10. The trigger 32 is pivotally movable in direction 33a toward the fixed handle 34 when the user applies a squeezing force against the trigger 32. A spring element 98 (FIG. 5) causes the trigger 32 to pivotally move in direction 33b when the user releases the squeezing force against the trigger 32.

In one example aspect, the trigger 32 comprises an elongated trigger hook 36, which defines an aperture 38 between the elongated trigger hook 36 and the trigger 32. The aperture 38 is suitably sized to receive one or multiple fingers of the user therethrough. The trigger 32 also may comprise a resilient portion 32a molded over the trigger 32 substrate. The overmolded resilient portion 32a is formed to provide a more comfortable contact surface for control of the trigger 32 in outward direction 33b. In one example aspect, the overmolded resilient portion 32a may be provided over a portion of the elongated trigger hook 36. The proximal surface of the elongated trigger hook 32 remains uncoated or coated with a non-resilient substrate to enable the user to easily slide their fingers in and out of the aperture 38. In another aspect, the geometry of the trigger forms a fully closed loop which defines an aperture suitably sized to receive one or multiple fingers of the user therethrough. The fully closed loop trigger also may comprise a resilient portion molded over the trigger substrate.

In one example aspect, the fixed handle 34 comprises a proximal contact surface 40 and a grip anchor or saddle surface 42. The saddle surface 42 rests on the web where the thumb and the index finger are joined on the hand. The proximal contact surface 40 has a pistol grip contour that receives the palm of the hand in a normal pistol grip with no rings or apertures. The profile curve of the proximal contact surface 40 may be contoured to accommodate or receive the palm of the hand. A stabilization tail 44 is located towards a more proximal portion of the handle assembly 12. The stabilization tail 44 may be in contact with the uppermost web portion of the hand located between the thumb and the index finger to stabilize the handle assembly 12 and make the handle assembly 12 more controllable.

In one example aspect, the switch assembly 28 may comprise a toggle switch 30. The toggle switch 30 may be implemented as a single component with a central pivot 304 located within inside the handle assembly 12 to eliminate the possibility of simultaneous activation. In one example aspect, the toggle switch 30 comprises a first projecting knob 30a and a second projecting knob 30b to set the power setting of the ultrasonic transducer 16 between a minimum power level (e.g., MIN) and a maximum power level (e.g., MAX). In another aspect, the rocker switch may pivot between a standard setting and a special setting. The special setting may allow one or more special programs, processes, or algorithms and described herein to be implemented by the device. The toggle switch 30 rotates about the central pivot as the first projecting knob 30a and the second projecting knob 30b are actuated The one or more projecting knobs 30a, 30b are coupled to one or more arms that move through a small arc and cause electrical contacts to close or open an electric circuit to electrically energize or de-energize the ultrasonic transducer 16 in accordance with the activation of the first or second projecting knobs 30a, 30b. The toggle switch 30 is coupled to the generator 20 to control the activation of the ultrasonic transducer 16. The toggle switch 30 comprises one or more electrical power setting switches to activate the ultrasonic transducer 16 to set one or more power settings for the ultrasonic transducer 16. The forces required to activate the toggle switch 30 are directed substantially toward the saddle point 42, thus avoiding any tendency of the instrument to rotate in the hand when the toggle switch 30 is activated.

In one example aspect, the first and second projecting knobs 30a, 30b are located on the distal end of the handle assembly 12 such that they can be easily accessible by the user to activate the power with minimal, or substantially no, repositioning of the hand grip, making it suitable to maintain control and keep attention focused on the surgical site (e.g., a monitor in a laparoscopic procedure) while activating the toggle switch 30. The projecting knobs 30a, 30b may be configured to wrap around the side of the handle assembly 12 to some extent to be more easily accessible by variable finger lengths and to allow greater freedom of access to activation in awkward positions or for shorter fingers. In the illustrated aspect, the first projecting knob 30a comprises a plurality of tactile elements 30c, e.g., textured projections or "bumps" in the illustrated aspect, to allow the user to differentiate the first projecting knob 30a from the second projecting knob 30b. It will be appreciated by those skilled in the art that several ergonomic features may be incorporated into the handle assembly 12. Such ergonomic features are described in U.S. Pat. App. Pub. No. 2009/0105750 entitled "Ergonomic Surgical Instruments" which is incorporated by reference herein in its entirety.

In one example aspect, the toggle switch 30 may be operated by the hand of the user. The user may easily access the first and second projecting knobs 30a, 30b at any point while also avoiding inadvertent or unintentional activation at any time. The toggle switch 30 may readily be operated with a finger to control the power to the ultrasonic assembly 16 and/or to the ultrasonic assembly 16. For example, the index finger may be employed to activate the first contact portion 30a to turn on the ultrasonic assembly 16 to a maximum (MAX) power level. The index finger may be employed to activate the second contact portion 30b to turn on the ultrasonic assembly 16 to a minimum (MIN) power level. In another aspect, the rocker switch may pivot the instrument 10 between a standard setting and a special setting. The special setting may allow one or more special programs to be implemented by the instrument 10. The toggle switch 30 may be operated without the user having to look at the first or second projecting knob 30a, 30b. For example, the first projecting knob 30a or the second projecting knob 30b may comprise a texture or projections to tactilely differentiate between the first and second projecting knobs 30a, 30b without looking.

In one example aspect, the distal rotation assembly 13 is rotatable without limitation in either direction about a longitudinal axis "T." The distal rotation assembly 13 is mechanically engaged to the elongated shaft assembly 14. The distal rotation assembly 13 is located on a distal end of the handle assembly 12. The distal rotation assembly 13 comprises a cylindrical hub 46 and a rotation knob 48 formed over the hub 46. The hub 46 mechanically engages the elongated shaft assembly 14. The rotation knob 48 may comprise fluted polymeric features and may be engaged by a finger (e.g., an index finger) to rotate the elongated shaft assembly 14. The hub 46 may comprise a material molded over the primary structure to form the rotation knob 48. The rotation knob 48 may be overmolded over the hub 46. The hub 46 comprises an end cap portion 46a that is exposed at the distal end. The end cap portion 46a of the hub 46 may contact the surface of a trocar during laparoscopic procedures. The hub 46 may be formed of a hard durable plastic such as polycarbonate to alleviate any friction that may occur between the end cap portion 46a and the trocar. The rotation knob 48 may comprise "scallops" or flutes formed of raised ribs 48a and concave portions 48b located between the ribs 48a to provide a more precise rotational grip. In one example aspect, the rotation knob 48 may comprise a plurality of flutes (e.g., three or more flutes). In other aspects, any suitable number of flutes may be employed. The rotation knob 48 may be formed of a softer polymeric material overmolded onto the hard plastic material. For example, the rotation knob 48 may be formed of pliable, resilient, flexible polymeric materials including Versaflex® TPE alloys made by GLS Corporation, for example. This softer overmolded material may provide a greater grip and more precise control of the movement of the rotation knob 48. It will be appreciated that any materials that provide adequate resistance to sterilization, are biocompatible, and provide adequate frictional resistance to surgical gloves may be employed to form the rotation knob 48.

In one example aspect, the handle assembly 12 is formed from two (2) housing portions or shrouds comprising a first portion 12a and a second portion 12b. From the perspective of a user viewing the handle assembly 12 from the distal end towards the proximal end, the first portion 12a is considered the right portion and the second portion 12b is considered the left portion. Each of the first and second portions 12a, 12b includes a plurality of interfaces 69 (FIG. 5) dimensioned to mechanically align and engage each another to form the handle assembly 12 and enclosing the internal working components thereof. The fixed handle 34, which is integrally associated with the handle assembly 12, takes shape upon the assembly of the first and second portions 12a and 12b of the handle assembly 12. A plurality of additional interfaces (not shown) may be disposed at various points around the periphery of the first and second portions 12a and 12b of the handle assembly 12 for ultrasonic welding purposes, e.g., energy direction/deflection points. The first and second portions 12a and 12b (as well as the other components described below) may be assembled together in any fashion known in the art. For example, alignment pins, snap-like interfaces, tongue and groove interfaces, locking tabs, adhesive ports, may all be utilized either alone or in combination for assembly purposes.

In one example aspect, the elongated shaft assembly 14 comprises a proximal end 50 adapted to mechanically engage the handle assembly 12 and the distal rotation assembly 13; and a distal end 52 adapted to mechanically engage the end effector assembly 26. The elongated shaft assembly 14 comprises an outer tubular sheath 56 and a reciprocating tubular actuating member 58 located within the outer tubular sheath 56. The proximal end of the tubular reciprocating tubular actuating member 58 is mechanically engaged to the trigger 32 of the handle assembly 12 to move in either direction 60A or 60B in response to the actuation and/or release of the trigger 32. The pivotably moveable trigger 32 may generate reciprocating motion along the longitudinal axis "T." Such motion may be used, for example, to actuate the jaws or clamping mechanism of the end effector assembly 26. A series of linkages translate the pivotal rotation of the trigger 32 to axial movement of a yoke coupled to an actuation mechanism, which controls the opening and closing of the jaws of the clamping mechanism of the end effector assembly 26. The distal end of the tubular reciprocating tubular actuating member 58 is mechanically engaged to the end effector assembly 26. In the illustrated aspect, the distal end of the tubular reciprocating tubular actuating member 58 is mechanically engaged to a clamp arm assembly 64, which is pivotable about a pivot point 70 (FIG. 4), to open and close the clamp arm assembly 64 in response to the actuation and/or release of the trigger 32. For example, in the illustrated aspect, the clamp arm assembly 64 is movable in direction 62A from an open position to a closed position about a pivot point 70 when the trigger 32 is squeezed in direction 33a. The clamp arm assembly 64 is movable in direction 62B from a closed position to an open position about the pivot point 70 when the trigger 32 is released or outwardly contacted in direction 33b.

In one example aspect, the end effector assembly 26 is attached at the distal end 52 of the elongated shaft assembly 14 and includes a clamp arm assembly 64 and a ultrasonic blade 66. The jaws of the clamping mechanism of the end effector assembly 26 are formed by clamp arm assembly 64 and the ultrasonic blade 66. The ultrasonic blade 66 is ultrasonically actuatable and is acoustically coupled to the ultrasonic transducer 16. The trigger 32 on the handle assembly 12 is ultimately connected to a drive assembly, which together, mechanically cooperate to effect movement of the clamp arm assembly 64. Squeezing the trigger 32 in direction 33a moves the clamp arm assembly 64 in direction 62A from an open position, wherein the clamp arm assembly 64 and the ultrasonic blade 66 are disposed in a spaced relation relative to one another, to a clamped or closed position, wherein the clamp arm assembly 64 and the ultrasonic blade 66 cooperate to grasp tissue therebetween. The clamp arm assembly 64 may comprise a clamp pad 69 to engage tissue between the ultrasonic blade 66 and the clamp arm 64. Releasing the trigger 32 in direction 33b moves the clamp arm assembly 64 in direction 62B from a closed relationship, to an open position, wherein the clamp arm assembly 64 and the ultrasonic blade 66 are disposed in a spaced relation relative to one another.

The proximal portion of the handle assembly 12 comprises a proximal opening 68 to receive the distal end of the ultrasonic assembly 16. The ultrasonic assembly 16 is inserted in the proximal opening 68 and is mechanically engaged to the elongated shaft assembly 14.

In one example aspect, the elongated trigger hook 36 portion of the trigger 32 provides a longer trigger lever with a shorter span and rotation travel. The longer lever of the elongated trigger hook 36 allows the user to employ multiple fingers within the aperture 38 to operate the elongated trigger hook 36 and cause the trigger 32 to pivot in direction 33b to open the jaws of the end effector assembly 26. For example, the user may insert three fingers (e.g., the middle, ring, and little fingers) in the aperture 38. Multiple fingers allows the surgeon to exert higher input forces on the trigger 32 and the elongated trigger hook 326 to activate the end effector assembly 26. The shorter span and rotation travel creates a more comfortable grip when closing or squeezing the trigger 32 in direction 33a or when opening the trigger 32 in the outward opening motion in direction 33b lessening the need to extend the fingers further outward. This substantially lessens hand fatigue and strain associated with the outward opening motion of the trigger 32 in direction 33b. The outward opening motion of the trigger may be spring-assisted by spring element 98 (FIG. 5) to help alleviate fatigue. The opening spring force is sufficient to assist the ease of opening, but not strong enough to adversely impact the tactile feedback of tissue tension during spreading dissection.

For example, during a surgical procedure either the index finger may be used to control the rotation of the elongated shaft assembly 14 to locate the jaws of the end effector assembly 26 in a suitable orientation. The middle and/or the other lower fingers may be used to squeeze the trigger 32 and grasp tissue within the jaws. Once the jaws are located in the desired position and the jaws are clamped against the tissue, the index finger can be used to activate the toggle switch 30 to adjust the power level of the ultrasonic transducer 16 to treat the tissue. Once the tissue has been treated, the user then may release the trigger 32 by pushing outwardly in the distal direction against the elongated trigger hook 36 with the middle and/or lower fingers to open the jaws of the end effector assembly 26. This basic procedure may be performed without the user having to adjust their grip of the handle assembly 12.

Figure 4:
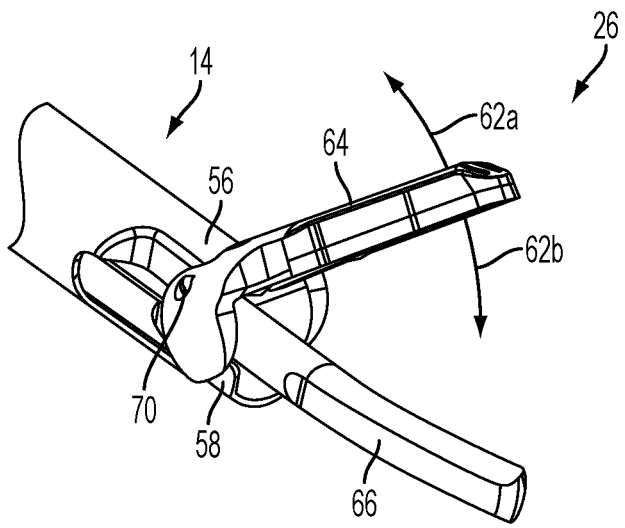
FIG. 4 illustrates an example end effector of a surgical instruments in accordance with one aspect of the present disclosure.

FIGS. 3-4 illustrate the connection of the elongated shaft assembly 14 relative to the end effector assembly 26. As previously described, in the illustrated aspect, the end effector assembly 26 comprises a clamp arm assembly 64 and a ultrasonic blade 66 to form the jaws of the clamping mechanism. The ultrasonic blade 66 may be an ultrasonically actuatable ultrasonic blade acoustically coupled to the ultrasonic transducer 16. The trigger 32 is mechanically connected to a drive assembly. Together, the trigger 32 and the drive assembly mechanically cooperate to move the clamp arm assembly 64 to an open position in direction 62A wherein the clamp arm assembly 64 and the ultrasonic blade 66 are disposed in spaced relation relative to one another, to a clamped or closed position in direction 62B wherein the clamp arm assembly 64 and the ultrasonic blade 66 cooperate to grasp tissue therebetween. The clamp arm assembly 64 may comprise a clamp pad 69 to engage tissue between the ultrasonic blade 66 and the clamp arm 64. The distal end of the tubular reciprocating tubular actuating member 58 is mechanically engaged to the end effector assembly 26. In the illustrated aspect, the distal end of the tubular reciprocating tubular actuating member 58 is mechanically engaged to the clamp arm assembly 64, which is pivotable about the pivot point 70, to open and close the clamp arm assembly 64 in response to the actuation and/or release of the trigger 32. For example, in the illustrated aspect, the clamp arm assembly 64 is movable from an open position to a closed position in direction 62B about a pivot point 70 when the trigger 32 is squeezed in direction 33a. The clamp arm assembly 64 is movable from a closed position to an open position in direction 62A about the pivot point 70 when the trigger 32 is released or outwardly contacted in direction 33b.

As previously discussed, the clamp arm assembly 64 may comprise electrodes electrically coupled to the electrosurgical/RF generator module 23 to receive therapeutic and/or sub-therapeutic energy, where the electrosurgical/RF energy may be applied to the electrodes either simultaneously or non simultaneously with the ultrasonic energy being applied to the ultrasonic blade 66. Such energy activations may be applied in any suitable combinations to achieve a desired tissue effect in cooperation with an algorithm or other control logic.

Figure 5:
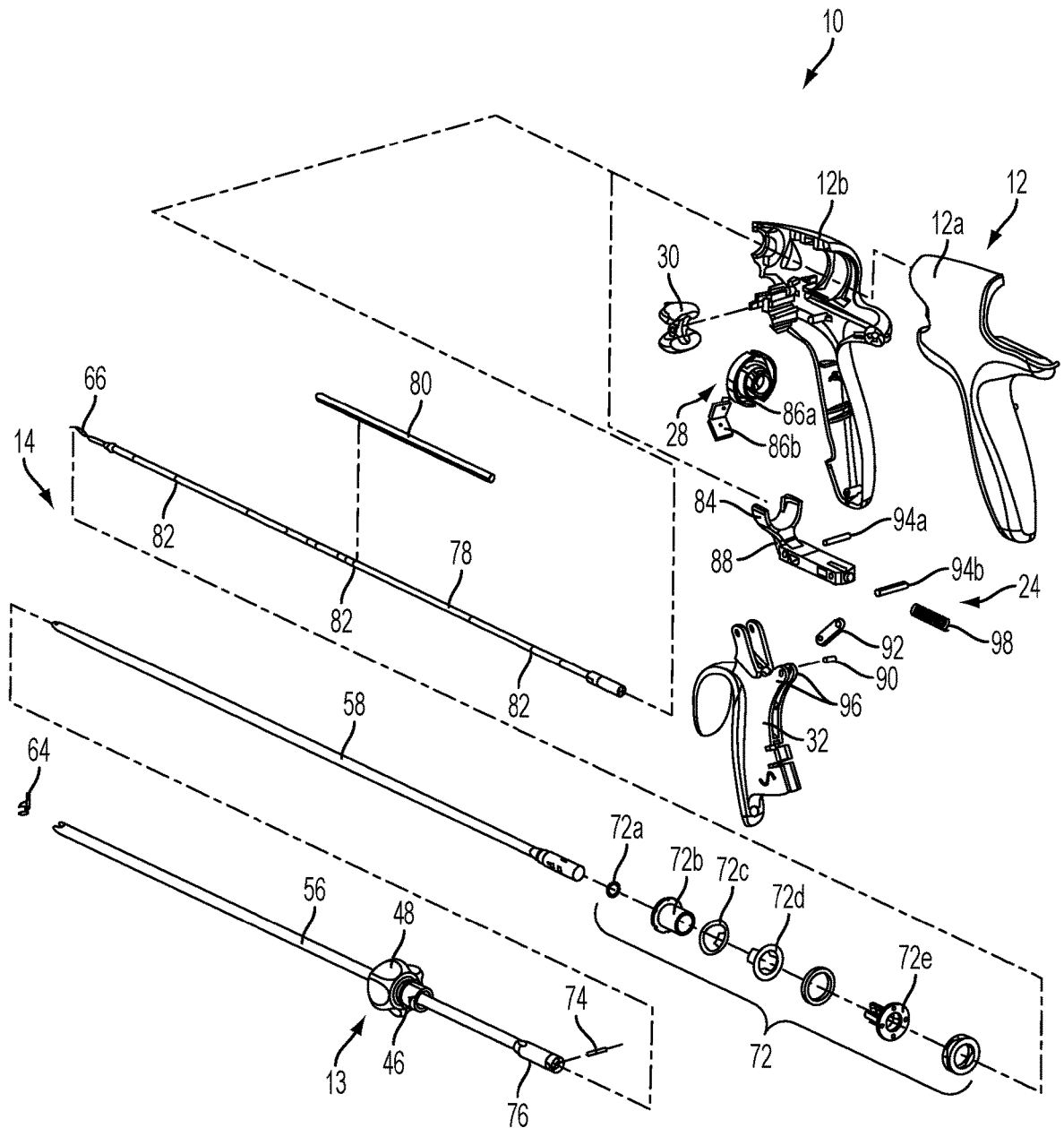
FIG. 5 is an exploded view of one aspect of a surgical instrument in accordance with one aspect of the present disclosure.

FIG. 5 is an exploded view of the ultrasonic surgical instrument 10 shown in FIG. 2. In the illustrated aspect, the exploded view shows the internal elements of the handle assembly 12, the handle assembly 12, the distal rotation assembly 13, the switch assembly 28, and the elongated shaft assembly 14. In the illustrated aspect, the first and second portions 12a, 12b mate to form the handle assembly 12. The first and second portions 12a, 12b each comprises a plurality of interfaces 69 dimensioned to mechanically align and engage one another to form the handle assembly 12 and enclose the internal working components of the ultrasonic surgical instrument 10. The rotation knob 48 is mechanically engaged to the outer tubular sheath 56 so that it may be rotated in circular direction 54 up to 360°. The outer tubular sheath 56 is located over the reciprocating tubular actuating member 58, which is mechanically engaged to and retained within the handle assembly 12 via a plurality of coupling elements 72. The coupling elements 72 may comprise an 0-ring 72a, a tube collar cap 72b, a distal washer 72c, a proximal washer 72d, and a thread tube collar 72e. The reciprocating tubular actuating member 58 is located within a reciprocating yoke 84, which is retained between the first and second portions 12a, 12b of the handle assembly 12. The yoke 84 is part of a reciprocating yoke assembly 88. A series of linkages translate the pivotal rotation of the elongated trigger hook 32 to the axial movement of the reciprocating yoke 84, which controls the opening and closing of the jaws of the clamping mechanism of the end effector assembly 26 at the distal end of the ultrasonic surgical instrument 10. In one example aspect, a four-link design provides mechanical advantage in a relatively short rotation span, for example.

In one example aspect, an ultrasonic transmission waveguide 78 is disposed inside the reciprocating tubular actuating member 58. The distal end 52 of the ultrasonic transmission waveguide 78 is acoustically coupled (e.g., directly or indirectly mechanically coupled) to the ultrasonic blade 66 and the proximal end 50 of the ultrasonic transmission waveguide 78 is received within the handle assembly 12. The proximal end 50 of the ultrasonic transmission waveguide 78 is adapted to acoustically couple to the distal end of the ultrasonic transducer 16. The ultrasonic transmission waveguide 78 is isolated from the other elements of the elongated shaft assembly 14 by a protective sheath 80 and a plurality of isolation elements 82, such as silicone rings. The outer tubular sheath 56, the reciprocating tubular actuating member 58, and the ultrasonic transmission waveguide 78 are mechanically engaged by a pin 74. The switch assembly 28 comprises the toggle switch 30 and electrical elements 86a,b to electrically energize the ultrasonic transducer 16 in accordance with the activation of the first or second projecting knobs 30a, 30b.

In one example aspect, the outer tubular sheath 56 isolates the user or the patient from the ultrasonic vibrations of the ultrasonic transmission waveguide 78. The outer tubular sheath 56 generally includes a hub 76. The outer tubular sheath 56 is threaded onto the distal end of the handle assembly 12. The ultrasonic transmission waveguide 78 extends through the opening of the outer tubular sheath 56 and the isolation elements 82 isolate the ultrasonic transmission waveguide 24 from the outer tubular sheath 56. The outer tubular sheath 56 may be attached to the waveguide 78 with the pin 74. The hole to receive the pin 74 in the waveguide 78 may occur nominally at a displacement node. The waveguide 78 may screw or snap into the hand piece handle assembly 12 by a stud. Flat portions on the hub 76 may allow the assembly to be torqued to a required level. In one example aspect, the hub 76 portion of the outer tubular sheath 56 is preferably constructed from plastic and the tubular elongated portion of the outer tubular sheath 56 is fabricated from stainless steel. Alternatively, the ultrasonic transmission waveguide 78 may comprise polymeric material surrounding it to isolate it from outside contact.

In one example aspect, the distal end of the ultrasonic transmission waveguide 78 may be coupled to the proximal end of the ultrasonic blade 66 by an internal threaded connection, preferably at or near an antinode. It is contemplated that the ultrasonic blade 66 may be attached to the ultrasonic transmission waveguide 78 by any suitable means, such as a welded joint or the like. Although the ultrasonic blade 66 may be detachable from the ultrasonic transmission waveguide 78, it is also contemplated that the single element end effector (e.g., the ultrasonic blade 66) and the ultrasonic transmission waveguide 78 may be formed as a single unitary piece.

In one example aspect, the trigger 32 is coupled to a linkage mechanism to translate the rotational motion of the trigger 32 in directions 33a and 33b to the linear motion of the reciprocating tubular actuating member 58 in corresponding directions 60a and 60b (FIG. 2). The trigger 32 comprises a first set of flanges 98 with openings formed therein to receive a first yoke pin 94a. The first yoke pin 94a is also located through a set of openings formed at the distal end of the yoke 84. The trigger 32 also comprises a second set of flanges 96 to receive a first end of a link 92. A trigger pin 90 is received in openings formed in the link 92 and the second set of flanges 96. The trigger pin 90 is received in the openings formed in the link 92 and the second set of flanges 96 and is adapted to couple to the first and second portions 12a, 12b of the handle assembly 12 to form a trigger pivot point for the trigger 32. A second end of the link 92 is received in a slot formed in a proximal end of the yoke 84 and is retained therein by a second yoke pin 94b. As the trigger 32 is pivotally rotated about a pivot point formed by the trigger pin 90, the yoke translates horizontally along a longitudinal axis "T" in a direction indicated by arrows 60a,b.

Figure 6:
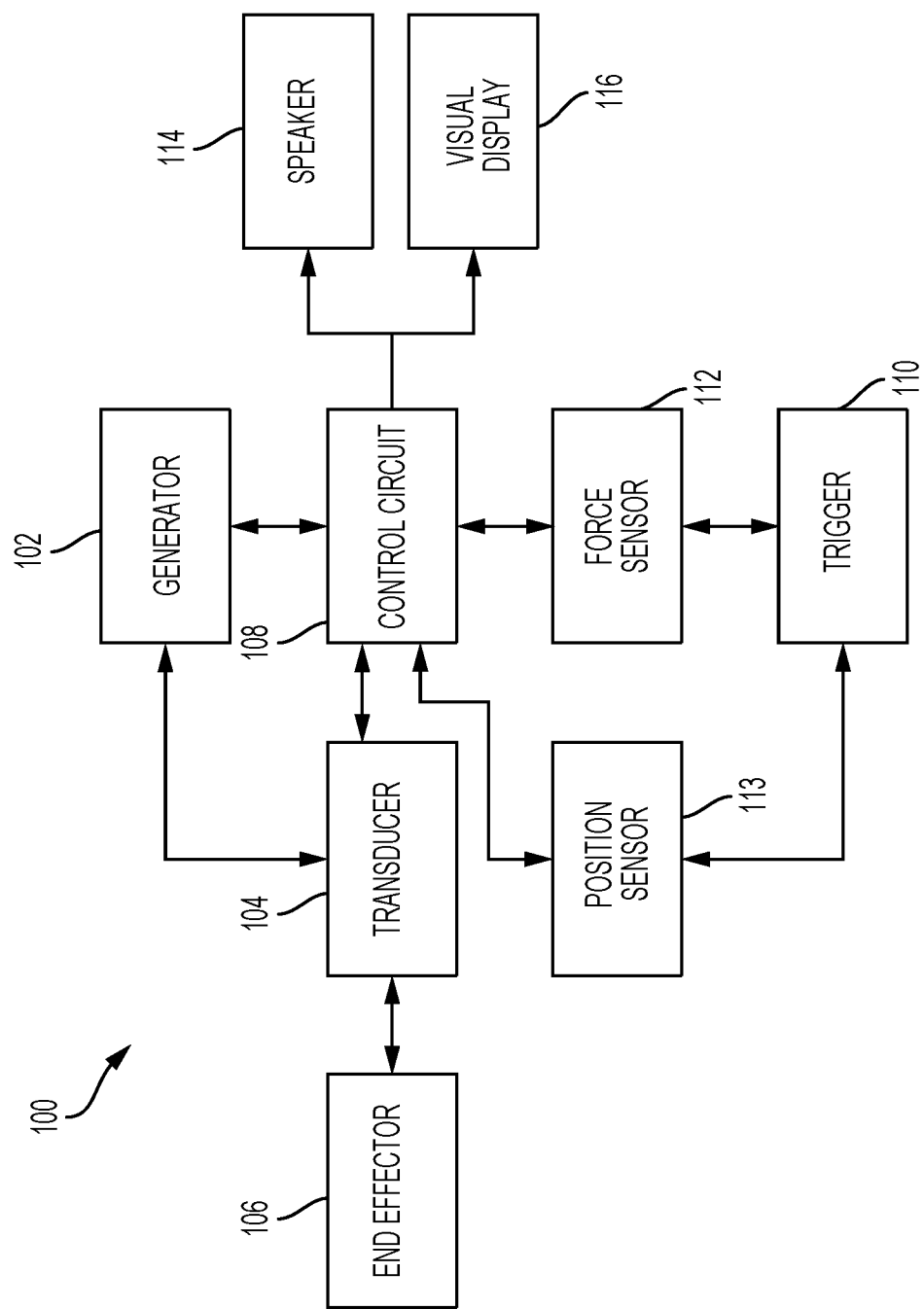
FIG. 6 illustrates a diagram of a surgical instrument in accordance with one aspect of the present disclosure.

FIG. 6 illustrates a diagram of one aspect of a force feedback surgical device 100 which may include or implement many of the features described herein. For example, in one aspect, surgical device 100 may be similar to or representative of surgical instrument 10. The surgical device 100 may include a generator 102. The surgical device 100 may also include an ultrasonic end effector 106, which may be activated when a clinician operates a trigger 110. When the trigger 110 is actuated, a force sensor 112 may generate a signal indicating the amount of force being applied to the trigger 110. In addition to, or instead of force sensor 112, the device 100 may include a position sensor 113, which may generate a signal indicating the position of the trigger 110 (e.g., how far the trigger has been depressed or otherwise actuated). In one aspect, the position sensor 113 may be a sensor positioned with the outer tubular sheath 56 described above or reciprocating tubular actuating member 58 located within the outer tubular sheath 56 described above In one aspect, the sensor may be a Hall-effect sensor or any suitable transducer that varies its output voltage in response to a magnetic field. The Hall effect sensor may be used for proximity switching, positioning, speed detection, and current sensing applications. In one aspect, the Hall-effect sensor operates as an analog transducer, directly returning a voltage. With a known magnetic field, its distance from the Hall plate can be determined.

A control circuit 108 may receive the signals from the sensors 112 and/or 113. The control circuit 108 may include any suitable analog or digital circuit components. The control circuit 108 also may communicate with the generator 102 and/or the transducer 104 to modulate the power delivered to the end effector 106 and/or the generator level or ultrasonic blade amplitude of the end effector 106 based on the force applied to the trigger 110 and/or the position of the trigger 110 and/or the position of the outer tubular sheath 56 described above relative to the reciprocating tubular actuating member 58 located within the outer tubular sheath 56 described above (e.g., as measured by a Hall-effect sensor and magnet combination). For example, as more force is applied to the trigger 110, more power and/or a higher ultrasonic blade amplitude may be delivered to the end effector 106. According to various aspects, the force sensor 112 may be replaced by a multi-position switch.

According to various aspects, the end effector 106 may include a clamp or clamping mechanism, for example, such as that described above with respect to FIGS. 1-5. When the trigger 110 is initially actuated, the clamping mechanism may close, clamping tissue between a clamp arm and the end effector 106. As the force applied to the trigger increases (e.g., as sensed by force sensor 112) the control circuit 608 may increase the power delivered to the end effector 106 by the transducer 104 and/or the generator level or ultrasonic blade amplitude brought about in the end effector 106. In one aspect, trigger position, as sensed by position sensor 113 or clamp or clamp arm position, as sensed by position sensor 113 (e.g., with a Hall-effect sensor), may be used by the control circuit 108 to set the power and/or amplitude of the end effector 106. For example, as the trigger is moved further towards a fully actuated position, or the clamp or clamp arm moves further towards the ultrasonic blade (or end effector 106), the power and/or amplitude of the end effector 106 may be increased.

According to various aspects, the surgical device 100 also may include one or more feedback devices for indicating the amount of power delivered to the end effector 106. For example, a speaker 114 may emit a signal indicative of the end effector power. According to various aspects, the speaker 114 may emit a series of pulse sounds, where the frequency of the sounds indicates power. In addition to, or instead of the speaker 114, the device may include a visual display 116. The visual display 116 may indicate end effector power according to any suitable method. For example, the visual display 116 may include a series of light emitting diodes (LEDs), where end effector power is indicated by the number of illuminated LEDs. The speaker 114 and/or visual display 116 may be driven by the control circuit 108.

According to various aspects, the device 100 may include a ratcheting device (not shown) connected to the trigger 110. The ratcheting device may generate an audible sound as more force is applied to the trigger 110, providing an indirect indication of end effector power. The device 100 may include other features that may enhance safety. For example, the control circuit 108 may be configured to prevent power from being delivered to the end effector 106 in excess of a predetermined threshold. Also, the control circuit 108 may implement a delay between the time when a change in end effector power is indicated (e.g., by speaker 114 or display 116), and the time when the change in end effector power is delivered. In this way, a clinician may have ample warning that the level of ultrasonic power that is to be delivered to the end effector 106 is about to change.

Figure 7:
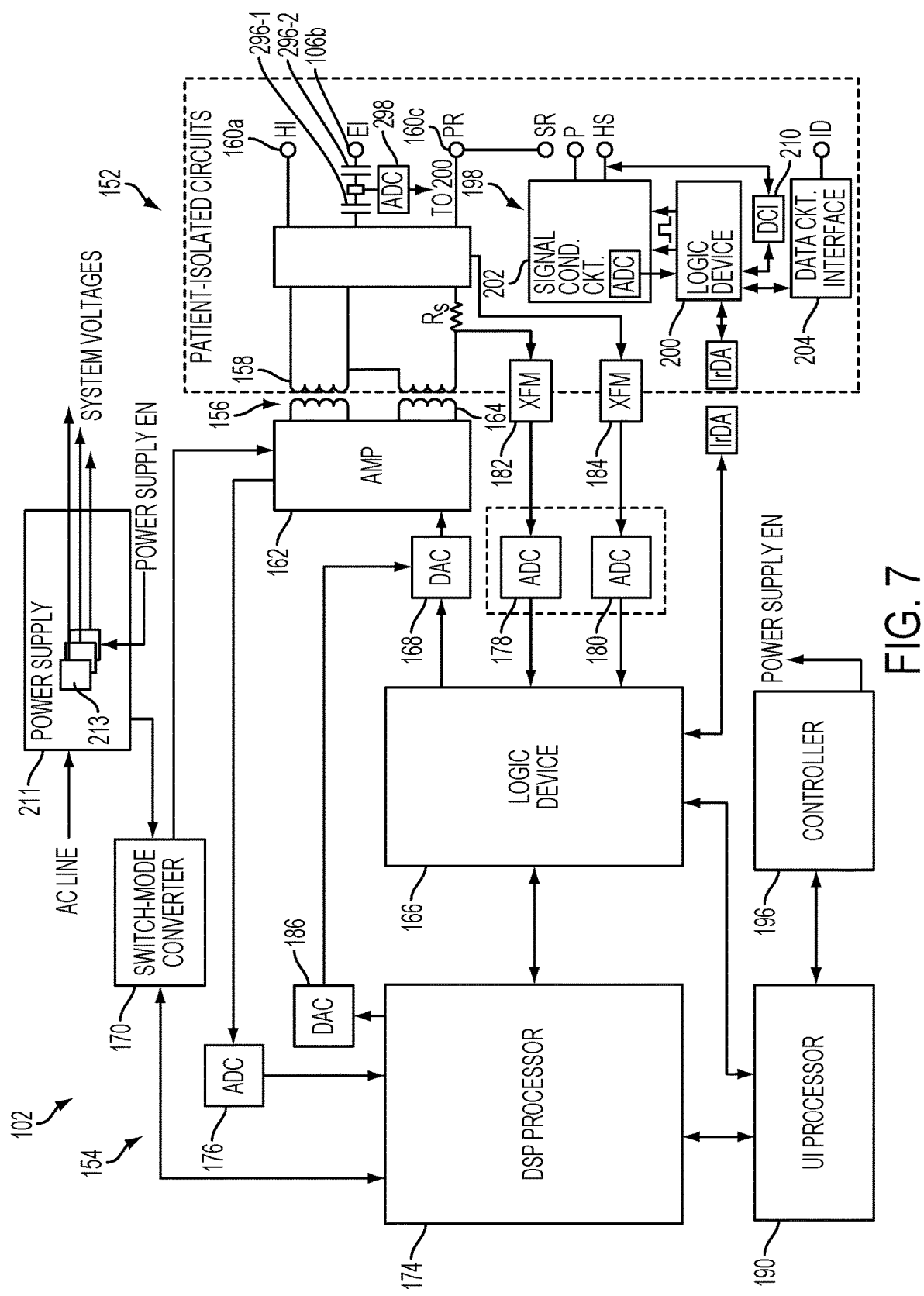
FIG. 7 illustrates a structural view of a generator architecture in accordance with one aspect of the present disclosure.
Figure 8A:
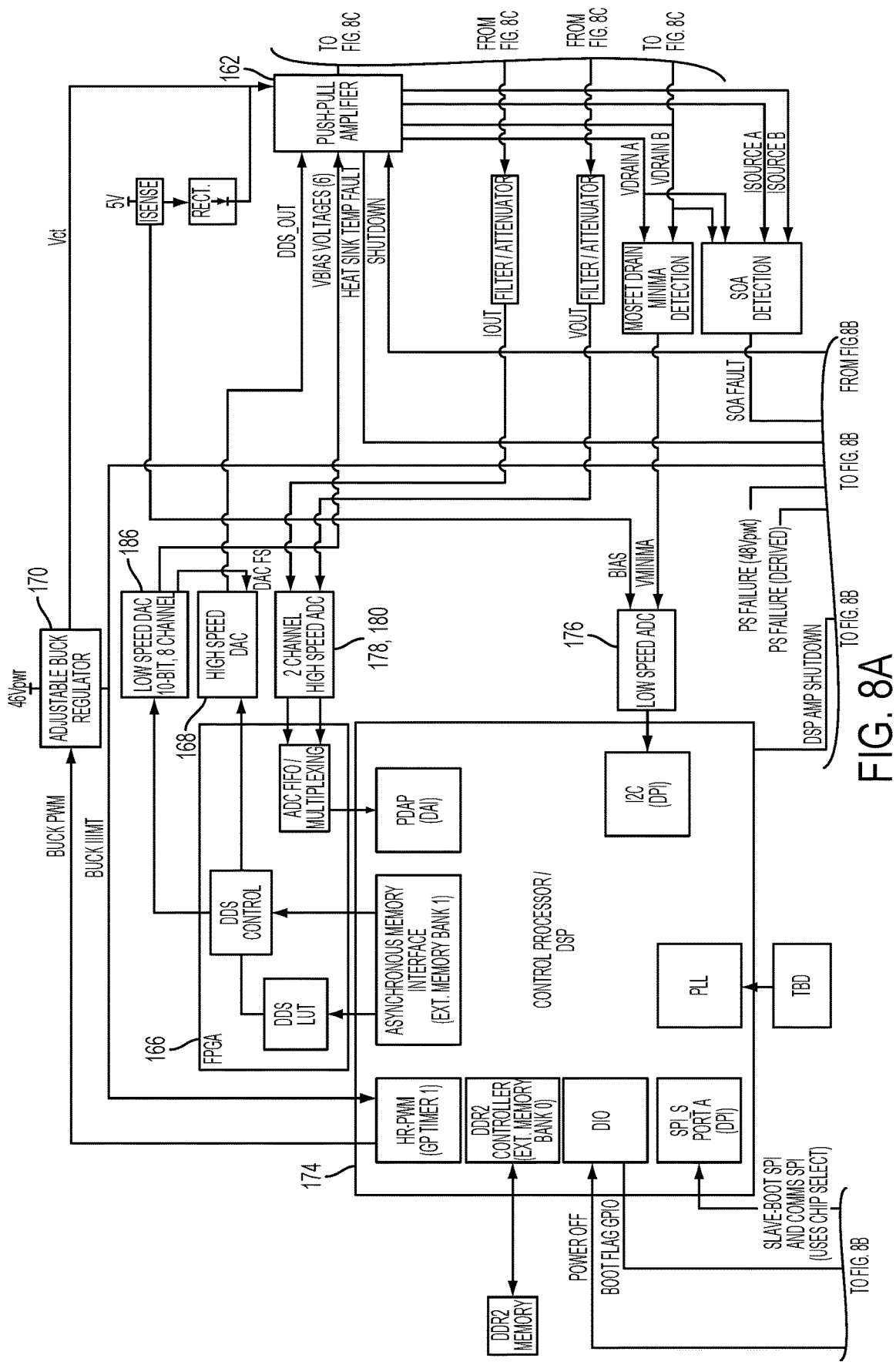
FIGS. 8A-8C illustrate functional views of a generator architecture in accordance with one aspect of the present disclosure.
Figure 8B:
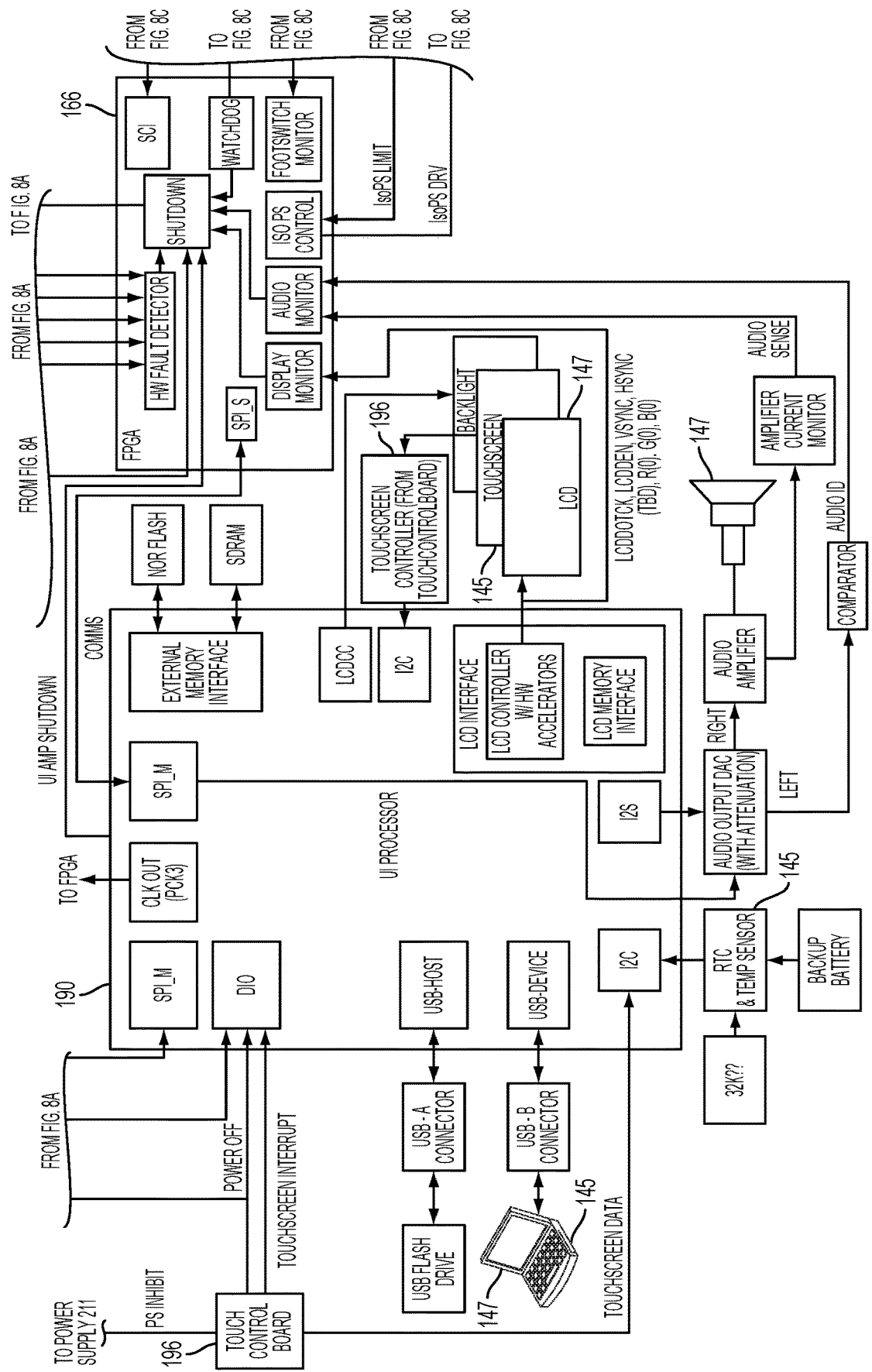
Figure 8C:
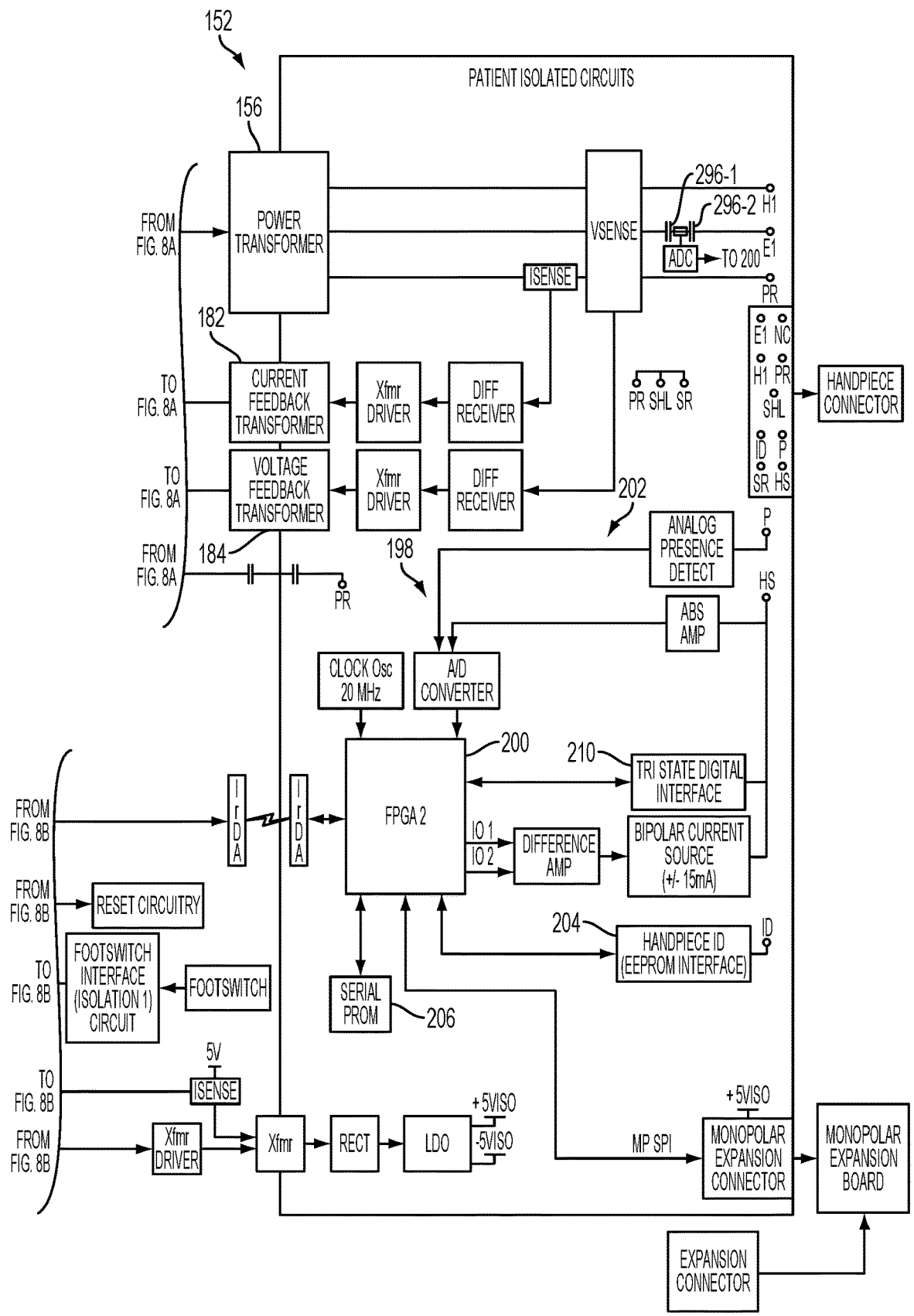
Figure 9:
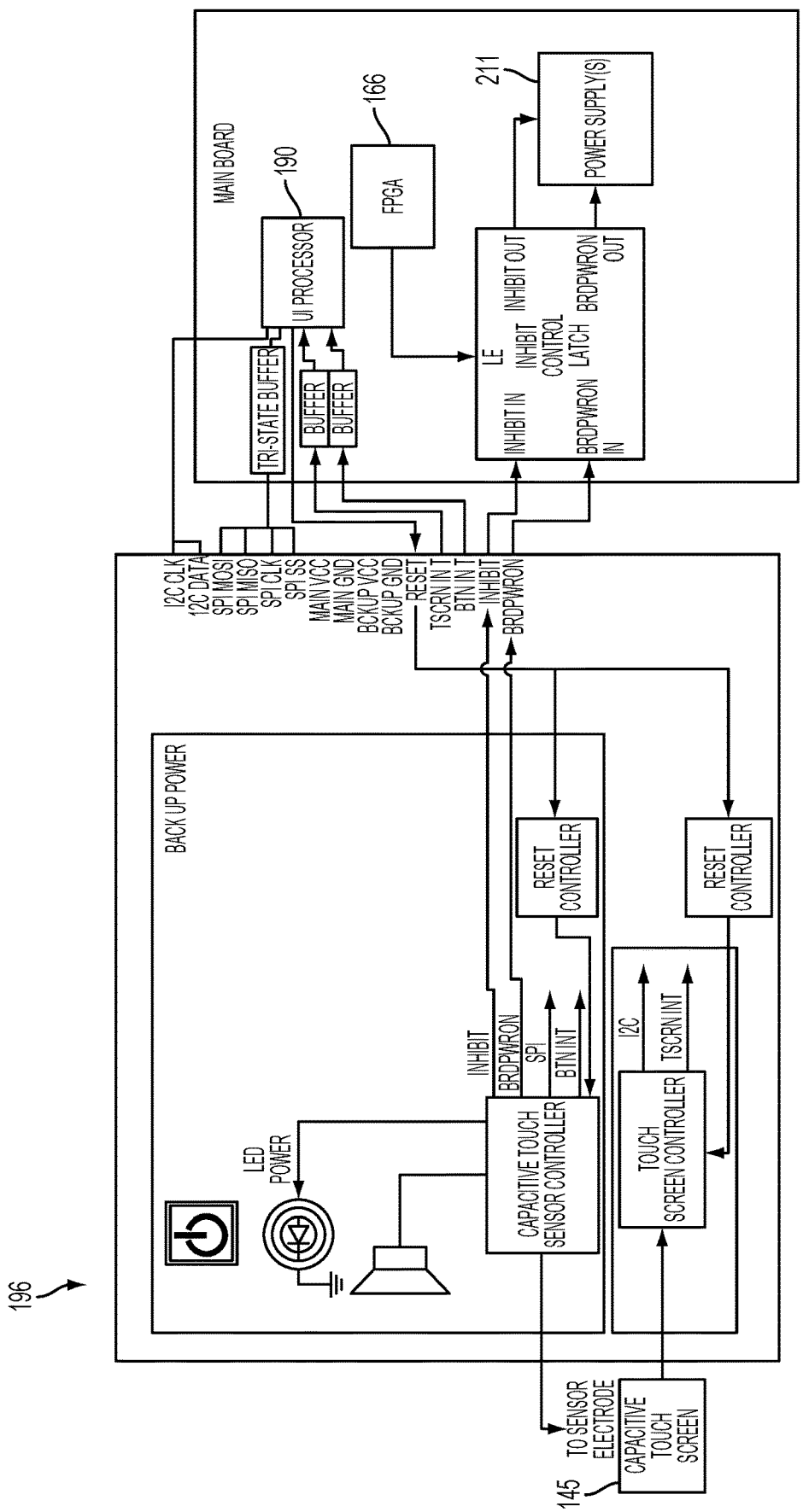
FIG. 9 illustrates a controller for monitoring input devices and controlling output devices in accordance with one aspect of the present disclosure.

FIG. 7 is a simplified diagram of one aspect of the generator 102 which may provide for inductorless tuning, among other benefits. FIGS. 8A-8C illustrate an architecture of the generator 102 of FIG. 7 according to one aspect of the present disclosure. FIG. 9 illustrates a controller 196 for monitoring input devices and controlling output devices in accordance with one aspect of the present disclosure. With reference now to FIGS. 7-9, the generator 102 may comprise a patient isolated stage 152 in communication with a non-isolated stage 154 via a power transformer 156. A secondary winding 158 of the power transformer 156 is contained in the isolated stage 152 and may comprise a tapped configuration (e.g., a center-tapped or non-center tapped configuration) to define drive signal outputs 160a, 160b, 160c for outputting drive signals to different surgical devices, such as, for example, a surgical device 100, ultrasonic surgical instrument 10, or an electrosurgical device. In particular, drive signal outputs 160a, 160c may output a drive signal (e.g., a 420V RMS drive signal) to an ultrasonic instrument 10, and drive signal outputs 160b, 160c may output a drive signal (e.g., a 100V RMS drive signal) to an electro surgical device, with output 160b corresponding to the center tap of the power transformer 156. The non-isolated stage 154 may comprise a power amplifier 162 having an output connected to a primary winding 164 of the power transformer 156. In certain aspects the power amplifier 162 may comprise a push-pull amplifier, for example. The non-isolated stage 154 may further comprise a programmable logic device 166 for supplying a digital output to a digital-to-analog converter (DAC) 168, which in turn supplies a corresponding analog signal to an input of the power amplifier 162. In certain aspects the programmable logic device 166 may comprise a field-programmable gate array (FPGA), for example. The programmable logic device 166, by virtue of controlling the power amplifier's 162 input via the DAC 168, may therefore control any of a number of parameters (e.g., frequency, waveform shape, waveform amplitude) of drive signals appearing at the drive signal outputs 160a, 160b, 160c. In certain aspects and as discussed below, the programmable logic device 166, in conjunction with a processor (e.g., processor 174 discussed below), may implement a number of digital signal processing (DSP)-based and/or other control algorithms to control parameters of the drive signals output by the generator 102.

Power may be supplied to a power rail of the power amplifier 162 by a switch-mode regulator 170. In certain aspects the switch-mode regulator 170 may comprise an adjustable buck regulator, for example. The non-isolated stage 154 may further comprise a processor 174, which in one aspect may comprise a DSP processor such as an Analog Devices ADSP-21469 SHARC DSP, available from Analog Devices, Norwood, Mass., for example. In certain aspects the processor 174 may control operation of the switch-mode power converter 170 responsive to voltage feedback data received from the power amplifier 162 by the processor 174 via an analog-to-digital converter (ADC) 176. In one aspect, for example, the processor 174 may receive as input, via the ADC 176, the waveform envelope of a signal (e.g., an RF signal) being amplified by the power amplifier 162. The processor 174 may then control the switch-mode regulator 170 (e.g., via a pulse-width modulated (PWM) output) such that the rail voltage supplied to the power amplifier 162 tracks the waveform envelope of the amplified signal. By dynamically modulating the rail voltage of the power amplifier 162 based on the waveform envelope, the efficiency of the power amplifier 162 may be significantly improved relative to a fixed rail voltage amplifier schemes.

In certain aspects and as discussed in further detail in connection with FIGS. 10A and 10B, the programmable logic device 166, in conjunction with the processor 174, may implement a direct digital synthesizer (DDS) control scheme to control the waveform shape, frequency and/or amplitude of drive signals output by the generator 102. In one aspect, for example, the programmable logic device 166 may implement a DDS control algorithm 268 by recalling waveform samples stored in a dynamically-updated lookup table (LUT), such as a RAM LUT which may be embedded in an FPGA. This control algorithm is particularly useful for ultrasonic applications in which an ultrasonic transducer may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 102 is impacted by various sources of distortion present in the output drive circuit (e.g., the power transformer 156, the power amplifier 162), voltage and current feedback data based on the drive signal may be input into an algorithm, such as an error control algorithm implemented by the processor 174, which compensates for distortion by suitably pre-distorting or modifying the waveform samples stored in the LUT on a dynamic, ongoing basis (e.g., in real-time). In one aspect, the amount or degree of pre-distortion applied to the LUT samples may be based on the error between a computed motional branch current and a desired current waveform shape, with the error being determined on a sample-by sample basis. In this way, the predistorted LUT samples, when processed through the drive circuit, may result in a motional branch drive signal having the desired waveform shape (e.g., sinusoidal) for optimally driving the ultrasonic transducer. In such aspects, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 154 may further comprise an ADC 178 and an ADC 180 coupled to the output of the power transformer 156 via respective isolation transformers 182, 184 for respectively sampling the voltage and current of drive signals output by the generator 102. In certain aspects, the ADCs 178, 180 may be configured to sample at high speeds (e.g., 80 Msps) to enable oversampling of the drive signals. In one aspect, for example, the sampling speed of the ADCs 178, 180 may enable approximately 200× (depending on drive frequency) oversampling of the drive signals. In certain aspects, the sampling operations of the ADCs 178, 180 may be performed by a single ADC receiving input voltage and current signals via a two-way multiplexer. The use of high-speed sampling in aspects of the generator 102 may enable, among other things, calculation of the complex current flowing through the motional branch (which may be used in certain aspects to implement DDS based waveform shape control described above), accurate digital filtering of the sampled signals, and calculation of real power consumption with a high degree of precision. Voltage and current feedback data output by the ADCs 178, 180 may be received and processed (e.g., FIFO buffering, multiplexing) by the programmable logic device 166 and stored in data memory for subsequent retrieval by, for example, the processor 174. As noted above, voltage and current feedback data may be used as input to an algorithm for pre-distorting or modifying LUT waveform samples on a dynamic and ongoing basis. In certain aspects, this may require each stored voltage and current feedback data pair to be indexed based on, or otherwise associated with, a corresponding LUT sample that was output by the programmable logic device 166 when the voltage and current feedback data pair was acquired. Synchronization of the LUT samples and the voltage and current feedback data in this manner contributes to the correct timing and stability of the pre-distortion algorithm.

In certain aspects, the voltage and current feedback data may be used to control the frequency and/or amplitude (e.g., current amplitude) of the drive signals. In one aspect, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of ultrasonic distortion and correspondingly enhancing impedance phase measurement accuracy. The determination of phase impedance and a frequency control signal may be implemented in the processor 174, for example, with the frequency control signal being supplied as input to a DDS control algorithm implemented by the programmable logic device 166.

In another aspect, for example, the current feedback data may be monitored in order to maintain the current amplitude of the drive signal at a current amplitude setpoint. The current amplitude setpoint may be specified directly or determined indirectly based on specified voltage amplitude and power setpoints. In certain aspects, control of the current amplitude may be implemented by control algorithm, such as, for example, a proportional-integral-derivative (PID) or a proportional-integral (PI) control algorithm, in the processor 174. Variables controlled by the control algorithm to suitably control the current amplitude of the drive signal may include, for example, the scaling of the LUT waveform samples stored in the programmable logic device 166 and/or the full-scale output voltage of the DAC 168 (which supplies the input to the power amplifier 162) via a DAC 186.

The non-isolated stage 154 may further comprise a processor 190 for providing, among other things user interface (UI) functionality. In one aspect, the processor 190 may comprise an Atmel AT91 SAM9263 processor having an ARM 926EJ-S core, available from Atmel Corporation, San Jose, Calif., for example. Examples of UI functionality supported by the processor 190 may include audible and visual user feedback, communication with peripheral devices (e.g., via a Universal Serial Bus (USB) interface), communication with the footswitch 120, communication with an input device 145 (e.g., a touch screen display) and communication with an output device 146 (e.g., a speaker). The processor 190 may communicate with the processor 174 and the programmable logic device (e.g., via serial peripheral interface (SPI) buses). Although the processor 190 may primarily support UI functionality, it may also coordinate with the processor 174 to implement hazard mitigation in certain aspects. For example, the processor 190 may be programmed to monitor various aspects of user input and/or other inputs (e.g., touch screen inputs, footswitch 120 inputs, temperature sensor inputs) and may disable the drive output of the generator 102 when an erroneous condition is detected.

In certain aspects, both the processor 174 and the processor 190 may determine and monitor the operating state of the generator 102. For the processor 174, the operating state of the generator 102 may dictate, for example, which control and/or diagnostic processes are implemented by the processor 174. For the processor 190, the operating state of the generator 102 may dictate, for example, which elements of a user interface (e.g., display screens, sounds) are presented to a user. The processors 174, 190 may independently maintain the current operating state of the generator 102 and recognize and evaluate possible transitions out of the current operating state. The processor 174 may function as the master in this relationship and determine when transitions between operating states are to occur. The processor 190 may be aware of valid transitions between operating states and may confirm if a particular transition is appropriate. For example, when the processor 174 instructs the processor 190 to transition to a specific state, the processor 190 may verify that requested transition is valid. In the event that a requested transition between states is determined to be invalid by the processor 190, the processor 190 may cause the generator 102 to enter a failure mode.

The non-isolated stage 154 may further comprise a controller 196 for monitoring input devices 145 (e.g., a capacitive touch sensor used for turning the generator 102 on and off, a capacitive touch screen). In certain aspects, the controller 196 may comprise at least one processor and/or other controller device in communication with the processor 190. In one aspect, for example, the controller 196 may comprise a processor (e.g., a Mega168 8-bit controller available from Atmel) configured to monitor user input provided via one or more capacitive touch sensors. In one aspect, the controller 196 may comprise a touch screen controller (e.g., a QT5480 touch screen controller available from Atmel) to control and manage the acquisition of touch data from a capacitive touch screen.

In certain aspects, when the generator 102 is in a "power off" state, the controller 196 may continue to receive operating power (e.g., via a line from a power supply of the generator 102, such as the power supply 211 discussed below). In this way, the controller 196 may continue to monitor an input device 145 (e.g., a capacitive touch sensor located on a front panel of the generator 102) for turning the generator 102 on and off. When the generator 102 is in the power off state, the controller 196 may wake the power supply (e.g., enable operation of one or more DC/DC voltage converters 213 of the power supply 211) if activation of the "on/off" input device 145 by a user is detected. The controller 196 may therefore initiate a sequence for transitioning the generator 102 to a "power on" state. Conversely, the controller 196 may initiate a sequence for transitioning the generator 102 to the power off state if activation of the "on/off" input device 145 is detected when the generator 102 is in the power on state. In certain aspects, for example, the controller 196 may report activation of the "on/off" input device 145 to the processor 190, which in turn implements the necessary process sequence for transitioning the generator 102 to the power off state. In such aspects, the controller 196 may have no independent ability for causing the removal of power from the generator 102 after its power on state has been established.

In certain aspects, the controller 196 may cause the generator 102 to provide audible or other sensory feedback for alerting the user that a power on or power off sequence has been initiated. Such an alert may be provided at the beginning of a power on or power off sequence and prior to the commencement of other processes associated with the sequence.

In certain aspects, the isolated stage 152 may comprise an instrument interface circuit 198 to, for example, provide a communication interface between a control circuit of a surgical device (e.g., a control circuit comprising handpiece switches) and components of the non-isolated stage 154, such as, for example, the programmable logic device 166, the processor 174 and/or the processor 190. The instrument interface circuit 198 may exchange information with components of the non-isolated stage 154 via a communication link that maintains a suitable degree of electrical isolation between the stages 152, 154, such as, for example, an infrared (IR)-based communication link. Power may be supplied to the instrument interface circuit 198 using, for example, a low-dropout voltage regulator powered by an isolation transformer driven from the non-isolated stage 154.

In one aspect, the instrument interface circuit 198 may comprise a programmable logic device 200 (e.g., an FPGA) in communication with a signal conditioning circuit 202. The signal conditioning circuit 202 may be configured to receive a periodic signal from the programmable logic device 200 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical device control circuit (e.g., by using a conductive pair in a cable that connects the generator 102 to the surgical device) and monitored to determine a state or configuration of the control circuit. The control circuit may comprise a number of switches, resistors and/or diodes to modify one or more characteristics (e.g., amplitude, rectification) of the interrogation signal such that a state or configuration of the control circuit is uniquely discernable based on the one or more characteristics. In one aspect, for example, the signal conditioning circuit 202 may comprise an ADC for generating samples of a voltage signal appearing across inputs of the control circuit resulting from passage of interrogation signal therethrough. The programmable logic device 200 (or a component of the nonisolated stage 154) may then determine the state or configuration of the control circuit based on the ADC samples.

In one aspect, the instrument interface circuit 198 may comprise a first data circuit interface 204 to enable information exchange between the programmable logic device 200 (or other element of the instrument interface circuit 198) and a first data circuit disposed in or otherwise associated with a surgical device. In certain aspects, a first data circuit 206 may be disposed in a cable integrally attached to a surgical device handpiece, or in an adaptor for interfacing a specific surgical device type or model with the generator 102. In certain aspects, the first data circuit may comprise a non-volatile storage device, such as an electrically erasable programmable read-only memory (EEPROM) device. In certain aspects and referring again to FIG. 7, the first data circuit interface 204 may be implemented separately from the programmable logic device 200 and comprise suitable circuitry (e.g., discrete logic devices, a processor) to enable communication between the programmable logic device 200 and the first data circuit. In other aspects, the first data circuit interface 204 may be integral with the programmable logic device 200.

In certain aspects, the first data circuit 206 may store information pertaining to the particular surgical device with which it is associated. Such information may include, for example, a model number, a serial number, a number of operations in which the surgical device has been used, and/or any other type of information. This information may be read by the instrument interface circuit 198 (e.g., by the programmable logic device 200), transferred to a component of the non-isolated stage 154 (e.g., to programmable logic device 166, processor 174 and/or processor 190) for presentation to a user via an output device 146 and/or for controlling a function or operation of the generator 102. Additionally, any type of information may be communicated to first data circuit 206 for storage therein via the first data circuit interface 204 (e.g., using the programmable logic device 200). Such information may comprise, for example, an updated number of operations in which the surgical device has been used and/or dates and/or times of its usage.

A surgical instrument may be detachable from a handpiece to promote instrument interchangeability and/or disposability. In such cases, known generators may be limited in their ability to recognize particular instrument configurations being used and to optimize control and diagnostic processes accordingly. The addition of readable data circuits to surgical device instruments to address this issue is problematic from a compatibility standpoint, however. For example, designing a surgical device to remain backwardly compatible with generators that lack the requisite data reading functionality may be impractical due to, for example, differing signal schemes, design complexity and cost. Aspects of instruments may use data circuits that may be implemented in existing surgical instruments economically and with minimal design changes to preserve compatibility of the surgical devices with current generator platforms.

Additionally, aspects of the generator 102 may enable communication with instrument-based data circuits. For example, the generator 102 may be configured to communicate with a second data circuit contained in an instrument of a surgical device. The instrument interface circuit 198 may comprise a second data circuit interface 210 to enable this communication. In one aspect, the second data circuit interface 210 may comprise a tri-state digital interface, although other interfaces may also be used. In certain aspects, the second data circuit may generally be any circuit for transmitting and/or receiving data. In one aspect, for example, the second data circuit may store information pertaining to the particular surgical instrument with which it is associated. Such information may include, for example, a model number, a serial number, a number of operations in which the surgical instrument has been used, and/or any other type of information. Additionally or alternatively, any type of information may be communicated to second data circuit for storage therein via the second data circuit interface 210 (e.g., using the programmable logic device 200). Such information may comprise, for example, an updated number of operations in which the instrument has been used and/or dates and/or times of its usage. In certain aspects, the second data circuit may transmit data acquired by one or more sensors (e.g., an instrument-based temperature sensor). In certain aspects, the second data circuit may receive data from the generator 102 and provide an indication to a user (e.g., an LED indication or other visible indication) based on the received data.

In certain aspects, the second data circuit and the second data circuit interface 210 may be configured such that communication between the programmable logic device 200 and the second data circuit can be effected without the need to provide additional conductors for this purpose (e.g., dedicated conductors of a cable connecting a handpiece to the generator 102). In one aspect, for example, information may be communicated to and from the second data circuit using a 1-wire bus communication scheme implemented on existing cabling, such as one of the conductors used transmit interrogation signals from the signal conditioning circuit 202 to a control circuit in a handpiece. In this way, design changes or modifications to the surgical device that might otherwise be necessary are minimized or reduced. Moreover, because different types of communications can be implemented over a common physical channel (either with or without frequency-band separation), the presence of a second data circuit may be "invisible" to generators that do not have the requisite data reading functionality, thus enabling backward compatibility of the surgical device instrument. In certain aspects, the isolated stage 152 may comprise at least one blocking capacitor 296-1 connected to the drive signal output 160*b* to prevent passage of DC current to a patient. A single blocking capacitor may be required to comply with medical regulations or standards, for example. While failure in single-capacitor designs is relatively uncommon, such failure may nonetheless have negative consequences. In one aspect, a second blocking capacitor 296-2 may be provided in series with the blocking capacitor 296-1, with current leakage from a point between the blocking capacitors 296-1, 296-2 being monitored by, for example, an ADC 298 for sampling a voltage induced by leakage current. The samples may be received by the programmable logic device 200, for example. Based on changes in the leakage current (as indicated by the voltage samples in the aspect of FIG. 7), the generator 102 may determine when at least one of the blocking capacitors 296-1, 296-2 has failed. Accordingly, the aspect of FIG. 7 may provide a benefit over single-capacitor designs having a single point of failure.

In certain aspects, the non-isolated stage 154 may comprise a power supply 211 for outputting DC power at a suitable voltage and current. The power supply may comprise, for example, a 400 W power supply for outputting a 48 VDC system voltage. The power supply 211 may further comprise one or more DC/DC voltage converters 213 for receiving the output of the power supply to generate DC outputs at the voltages and currents required by the various components of the generator 102. As discussed above in connection with the controller 196, one or more of the DC/DC voltage converters 213 may receive an input from the controller 196 when activation of the "on/off" input device 145 by a user is detected by the controller 196 to enable operation of, or wake, the DC/DC voltage converters 213.

Figure 10A:
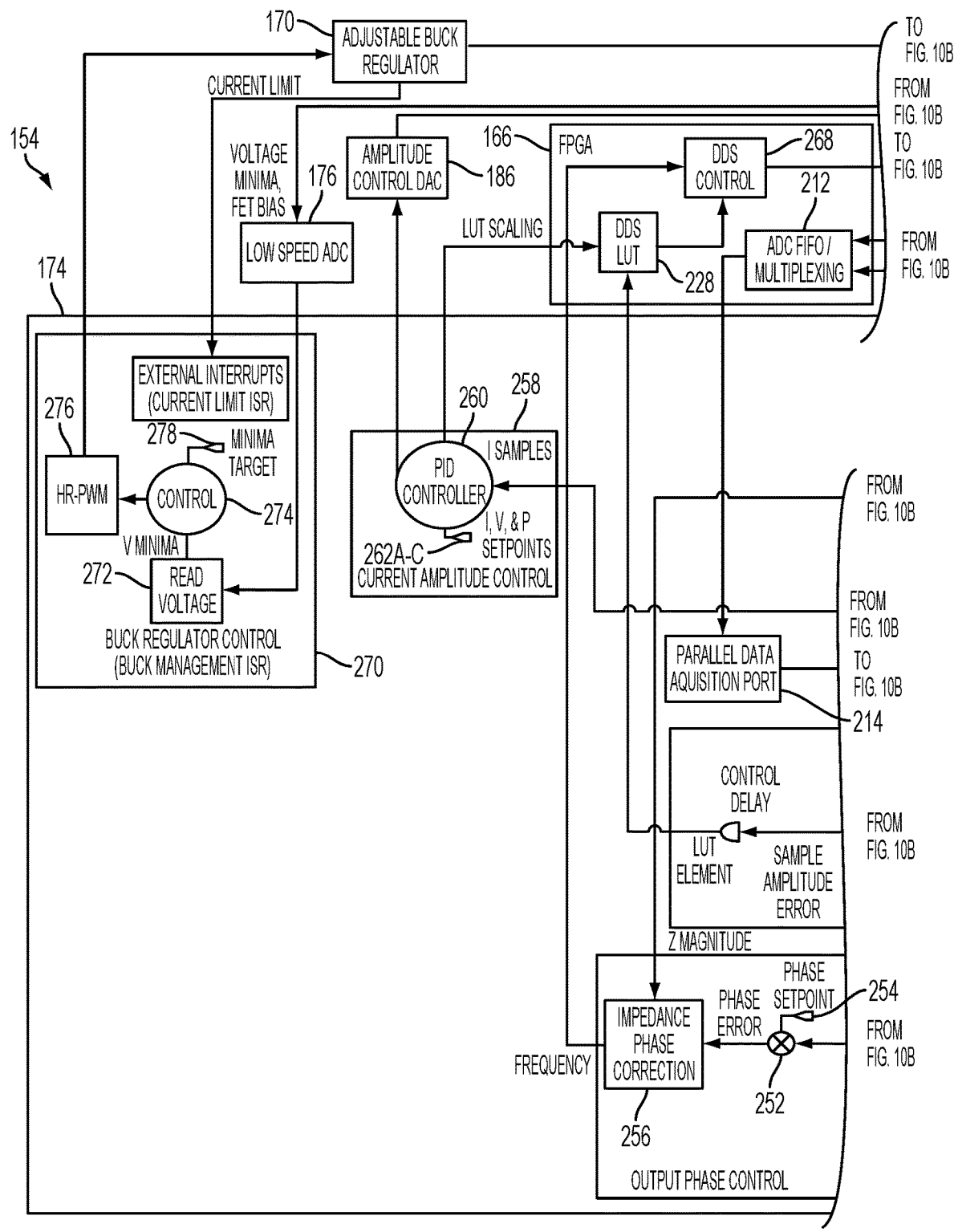
FIGS. 10A and 10B illustrate structural and functional aspects of one aspect of the generator in accordance with one aspect the present disclosure.
Figure 10B:
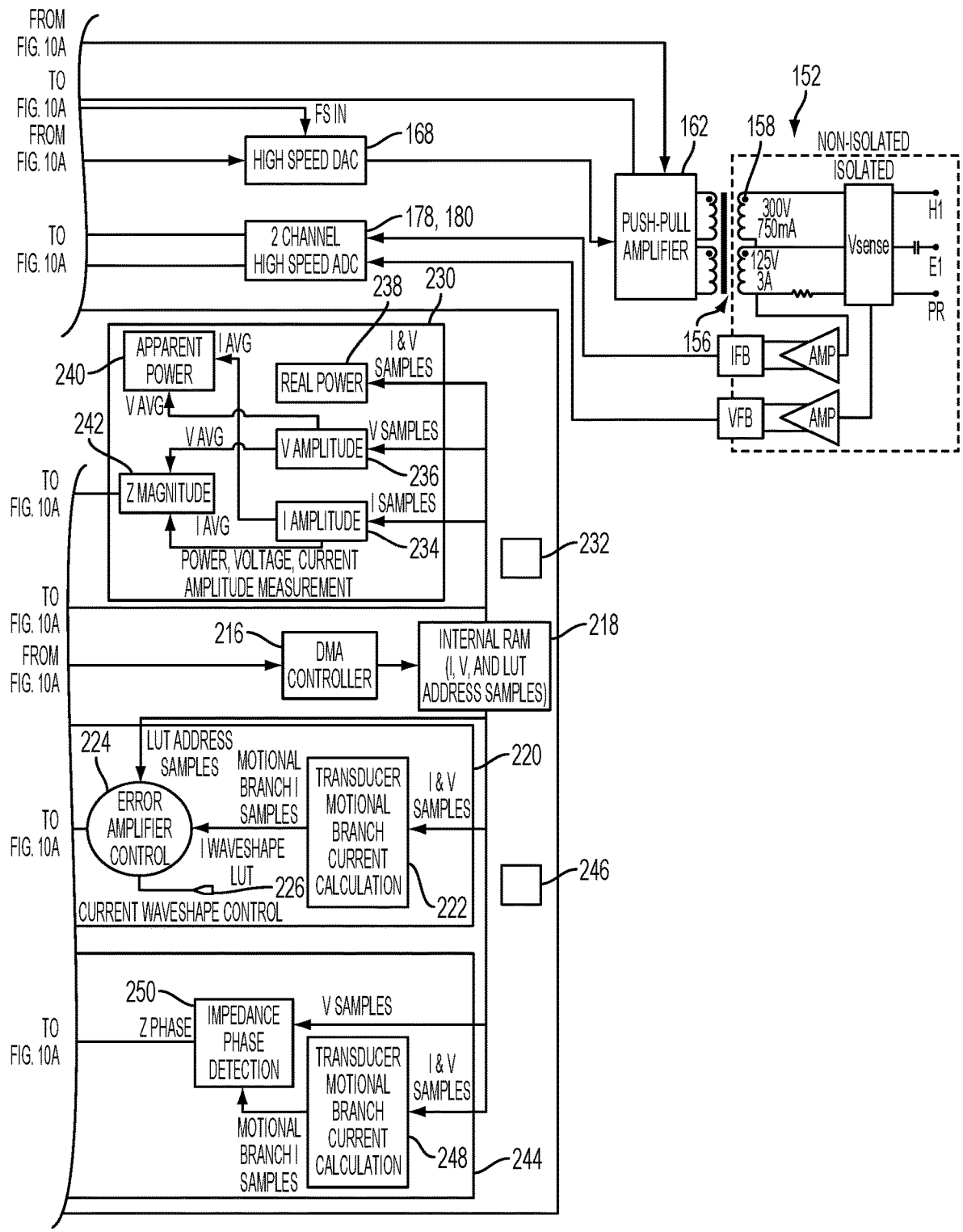

FIGS. 10A and 10B illustrate certain functional and structural aspects of one aspect of the generator 102. Feedback indicating current and voltage output from the secondary winding 158 of the power transformer 156 is received by the ADCs 178, 180, respectively. As shown, the ADCs 178, 180 may be implemented as a 2-channel ADC and may sample the feedback signals at a high speed (e.g., 80 Msps) to enable oversampling (e.g., approximately 200×oversampling) of the drive signals. The current and voltage feedback signals may be suitably conditioned in the analog domain (e.g., amplified, filtered) prior to processing by the ADCs 178, 180. Current and voltage feedback samples from the ADCs 178, 180 may be individually buffered and subsequently multiplexed or interleaved into a single data stream within block 212 of the programmable logic device 166. In the aspect of FIGS. 10A and 10B, the programmable logic device 166 comprises an FPGA.

The multiplexed current and voltage feedback samples may be received by a parallel data acquisition port (PDAP) implemented within block 214 of the processor 174. The PDAP may comprise a packing unit for implementing any of a number of methodologies for correlating the multiplexed feedback samples with a memory address. In one aspect, for example, feedback samples corresponding to a particular LUT sample output by the programmable logic device 166 may be stored at one or more memory addresses that are correlated or indexed with the LUT address of the LUT sample. In another aspect, feedback samples corresponding to a particular LUT sample output by the programmable logic device 166 may be stored, along with the LUT address of the LUT sample, at a common memory location. In any event, the feedback samples may be stored such that the address of an LUT sample from which a particular set of feedback samples originated may be subsequently ascertained. As discussed above, synchronization of the LUT sample addresses and the feedback samples in this way contributes to the correct timing and stability of the pre-distortion algorithm. A direct memory access (DMA) controller implemented at block 216 of the processor 174 may store the feedback samples (and any LUT sample address data, where applicable) at a designated memory location 218 of the processor 174 (e.g., internal RAM).

Block 220 of the processor 174 may implement a pre-distortion algorithm for pre-distorting or modifying the LUT samples stored in the programmable logic device 166 on a dynamic, ongoing basis. As discussed above, pre-distortion of the LUT samples may compensate for various sources of distortion present in the output drive circuit of the generator 102. The pre-distorted LUT samples, when processed through the drive circuit, will therefore result in a drive signal having the desired waveform shape (e.g., sinusoidal) for optimally driving the ultrasonic transducer.

At block 222 of the pre-distortion algorithm, the current through the motional branch of the ultrasonic transducer is determined. The motional branch current may be determined using Kirchoff's Current Law based on, for example, the current and voltage feedback samples stored at memory location 218, a value of the ultrasonic transducer static capacitance Co (measured or known a priori) and a known value of the drive frequency. A motional branch current sample for each set of stored current and voltage feedback samples associated with a LUT sample may be determined.

At block 224 of the pre-distortion algorithm, each motional branch current sample determined at block 222 is compared to a sample of a desired current waveform shape to determine a difference, or sample amplitude error, between the compared samples. For this determination, the sample of the desired current waveform shape may be supplied, for example, from a waveform shape LUT 226 containing amplitude samples for one cycle of a desired current waveform shape. The particular sample of the desired current waveform shape from the LUT 226 used for the comparison may be dictated by the LUT sample address associated with the motional branch current sample used in the comparison. Accordingly, the input of the motional branch current to block 224 may be synchronized with the input of its associated LUT sample address to block 224. The LUT samples stored in the programmable logic device 166 and the LUT samples stored in the waveform shape LUT 226 may therefore be equal in number. In certain aspects, the desired current waveform shape represented by the LUT samples stored in the waveform shape LUT 226 may be a fundamental sine wave. Other waveform shapes may be desirable. For example, it is contemplated that a fundamental sine wave for driving main longitudinal motion of an ultrasonic transducer superimposed with one or more other drive signals at other frequencies, such as a third order ultrasonic for driving at least two mechanical resonances for beneficial vibrations of transverse or other modes, could be used.

Each value of the sample amplitude error determined at block 224 may be transmitted to the LUT of the programmable logic device 166 (shown at block 228 in FIG. 10A) along with an indication of its associated LUT address. Based on the value of the sample amplitude error and its associated address (and, optionally, values of sample amplitude error for the same LUT address previously received), the LUT 228 (or other control block of the programmable logic device 166) may pre-distort or modify the value of the LUT sample stored at the LUT address such that the sample amplitude error is reduced or minimized. It will be appreciated that such pre-distortion or modification of each LUT sample in an iterative manner across the entire range of LUT addresses will cause the waveform shape of the generator's output current to match or conform to the desired current waveform shape represented by the samples of the waveform shape LUT 226.

Current and voltage amplitude measurements, power measurements and impedance measurements may be determined at block 230 of the processor 174 based on the current and voltage feedback samples stored at memory location 218. Prior to the determination of these quantities, the feedback samples may be suitably scaled and, in certain aspects, processed through a suitable filter 232 to remove noise resulting from, for example, the data acquisition process and induced ultrasonic components. The filtered voltage and current samples may therefore substantially represent the fundamental frequency of the generator's drive output signal. In certain aspects, the filter 232 may be a finite impulse response (FIR) filter applied in the frequency domain. Such aspects may use the fast Fourier transform (FFT) of the output drive signal current and voltage signals. In certain aspects, the resulting frequency spectrum may be used to provide additional generator functionality. In one aspect, for example, the ratio of the second and/or third order ultrasonic component relative to the fundamental frequency component may be used as a diagnostic indicator. At block 234, a root mean square (RMS) calculation may be applied to a sample size of the current feedback samples representing an integral number of cycles of the drive signal to generate a measurement Irms representing the drive signal output current.

At block 236, a root mean square (RMS) calculation may be applied to a sample size of the voltage feedback samples representing an integral number of cycles of the drive signal to determine a measurement Vrms representing the drive signal output voltage. At block 238, the current and voltage feedback samples may be multiplied point by point, and a mean calculation is applied to samples representing an integral number of cycles of the drive signal to determine a measurement Pr of the generator's real output power.

At block 240, measurement Pa of the generator's apparent output power may be determined as the product Vrms·Irms.

At block 242, measurement Zm of the load impedance magnitude may be determined as the quotient Vrms/Irms.

In certain aspects, the quantities Irms, Vrms, Pr, Pa, and Zm determined at blocks 234, 236, 238, 240 and 242 may be used by the generator 102 to implement any of number of control and/or diagnostic processes. In certain aspects, any of these quantities may be communicated to a user via, for example, an output device 146 integral with the generator 102 or an output device 146 connected to the generator 102 through a suitable communication interface (e.g., a USB interface). Various diagnostic processes may include, without limitation, handpiece integrity, instrument integrity, instrument attachment integrity, instrument overload, approaching instrument overload, frequency lock failure, over-voltage, over-current, over-power, voltage sense failure, current sense failure, audio indication failure, visual indication failure, short circuit, power delivery failure, blocking capacitor failure, for example.

Block 244 of the processor 174 may implement a phase control algorithm for determining and controlling the impedance phase of an electrical load (e.g., the ultrasonic transducer) driven by the generator 102. As discussed above, by controlling the frequency of the drive signal to minimize or reduce the difference between the determined impedance phase and an impedance phase setpoint (e.g., 0°), the effects of ultrasonic distortion may be minimized or reduced, and the accuracy of the phase measurement increased.

The phase control algorithm receives as input the current and voltage feedback samples stored in the memory location 218. Prior to their use in the phase control algorithm, the feedback samples may be suitably scaled and, in certain aspects, processed through a suitable filter 246 (which may be identical to filter 232) to remove noise resulting from the data acquisition process and induced ultrasonic components, for example. The filtered voltage and current samples may therefore substantially represent the fundamental frequency of the generator's drive output signal.

At block 248 of the phase control algorithm, the current through the motional branch of the ultrasonic transducer is determined. This determination may be identical to that described above in connection with block 222 of the pre-distortion algorithm. The output of block 248 may thus be, for each set of stored current and voltage feedback samples associated with a LUT sample, a motional branch current sample.

At block 250 of the phase control algorithm, impedance phase is determined based on the synchronized input of motional branch current samples determined at block 248 and corresponding voltage feedback samples. In certain aspects, the impedance phase is determined as the average of the impedance phase measured at the rising edge of the waveforms and the impedance phase measured at the falling edge of the waveforms.

At block 252 of the of the phase control algorithm, the value of the impedance phase determined at block 222 is compared to phase setpoint 254 to determine a difference, or phase error, between the compared values.

At block 256 of the phase control algorithm, based on a value of phase error determined at block 252 and the impedance magnitude determined at block 242, a frequency output for controlling the frequency of the drive signal is determined. The value of the frequency output may be continuously adjusted by the block 256 and transferred to a DDS control block 268 (discussed below) in order to maintain the impedance phase determined at block 250 at the phase setpoint (e.g., zero phase error). In certain aspects, the impedance phase may be regulated to a oo phase setpoint. In this way, any ultrasonic distortion will be centered about the crest of the voltage waveform, enhancing the accuracy of phase impedance determination.

Block 258 of the processor 174 may implement an algorithm for modulating the current amplitude of the drive signal in order to control the drive signal current, voltage and power in accordance with user specified setpoints, or in accordance with requirements specified by other processes or algorithms implemented by the generator 102. Control of these quantities may be realized, for example, by scaling the LUT samples in the LUT 228 and/or by adjusting the full-scale output voltage of the DAC 168 (which supplies the input to the power amplifier 162) via a DAC 186. Block 260 (which may be implemented as a PID controller in certain aspects) may receive as input current feedback samples (which may be suitably scaled and filtered) from the memory location 218. The current feedback samples may be compared to a "current demand" Id value dictated by the controlled variable (e.g., current, voltage or power) to determine if the drive signal is supplying the necessary current. In aspects in which drive signal current is the control variable, the current demand Id may be specified directly by a current setpoint 262A (Isp). For example, an RMS value of the current feedback data (determined as in block 234) may be compared to user-specified RMS current setpoint Isp to determine the appropriate controller action. If, for example, the current feedback data indicates an RMS value less than the current setpoint Isp, LUT scaling and/or the full-scale output voltage of the DAC 168 may be adjusted by the block 260 such that the drive signal current is increased. Conversely, block 260 may adjust LUT scaling and/or the full-scale output voltage of the DAC 168 to decrease the drive signal current when the current feedback data indicates an RMS value greater than the current setpoint Isp.

In aspects in which the drive signal voltage is the control variable, the current demand Id may be specified indirectly, for example, based on the current required to maintain a desired voltage setpoint 262B (Vsp) given the load impedance magnitude Zm measured at block 242 (e.g. Id=Vsp/Zm). Similarly, in aspects in which drive signal power is the control variable, the current demand Id may be specified indirectly, for example, based on the current required to maintain a desired power setpoint 262C (Psp) given the voltage Vrms measured at blocks 236 (e.g. Id=Psp/Vrms).

Block 268 may implement a DDS control algorithm for controlling the drive signal by recalling LUT samples stored in the LUT 228. In certain aspects, the DDS control algorithm be a numerically-controlled oscillator (NCO) algorithm for generating samples of a waveform at a fixed clock rate using a point (memory location)-skipping technique. The NCO algorithm may implement a phase accumulator, or frequency-to-phase converter, that functions as an address pointer for recalling LUT samples from the LUT 228. In one aspect, the phase accumulator may be a D step size, modulo N phase accumulator, where D is a positive integer representing a frequency control value, and N is the number of LUT samples in the LUT 228. A frequency control value of D=1, for example, may cause the phase accumulator to sequentially point to every address of the LUT 228, resulting in a waveform output replicating the waveform stored in the LUT 228. When D>1, the phase accumulator may skip addresses in the LUT 228, resulting in a waveform output having a higher frequency. Accordingly, the frequency of the waveform generated by the DDS control algorithm may therefore be controlled by suitably varying the frequency control value. In certain aspects, the frequency control value may be determined based on the output of the phase control algorithm implemented at block 244. The output of block 268 may supply the input of (DAC) 168, which in turn supplies a corresponding analog signal to an input of the power amplifier 162.

Block 270 of the processor 174 may implement a switch-mode converter control algorithm for dynamically modulating the rail voltage of the power amplifier 162 based on the waveform envelope of the signal being amplified, thereby improving the efficiency of the power amplifier 162. In certain aspects, characteristics of the waveform envelope may be determined by monitoring one or more signals contained in the power amplifier 162. In one aspect, for example, characteristics of the waveform envelope may be determined by monitoring the minima of a drain voltage (e.g., a MOSFET drain voltage) that is modulated in accordance with the envelope of the amplified signal. A minima voltage signal may be generated, for example, by a voltage minima detector coupled to the drain voltage. The minima voltage signal may be sampled by ADC 176, with the output minima voltage samples being received at block 272 of the switch-mode converter control algorithm. Based on the values of the minima voltage samples, block 274 may control a PWM signal output by a PWM generator 276, which, in turn, controls the rail voltage supplied to the power amplifier 162 by the switch-mode regulator 170. In certain aspects, as long as the values of the minima voltage samples are less than a minima target 278 input into block 262, the rail voltage may be modulated in accordance with the waveform envelope as characterized by the minima voltage samples. When the minima voltage samples indicate low envelope power levels, for example, block 274 may cause a low rail voltage to be supplied to the power amplifier 162, with the full rail voltage being supplied only when the minima voltage samples indicate maximum envelope power levels. When the minima voltage samples fall below the minima target 278, block 274 may cause the rail voltage to be maintained at a minimum value suitable for ensuring proper operation of the power amplifier 162.

Figure 32:
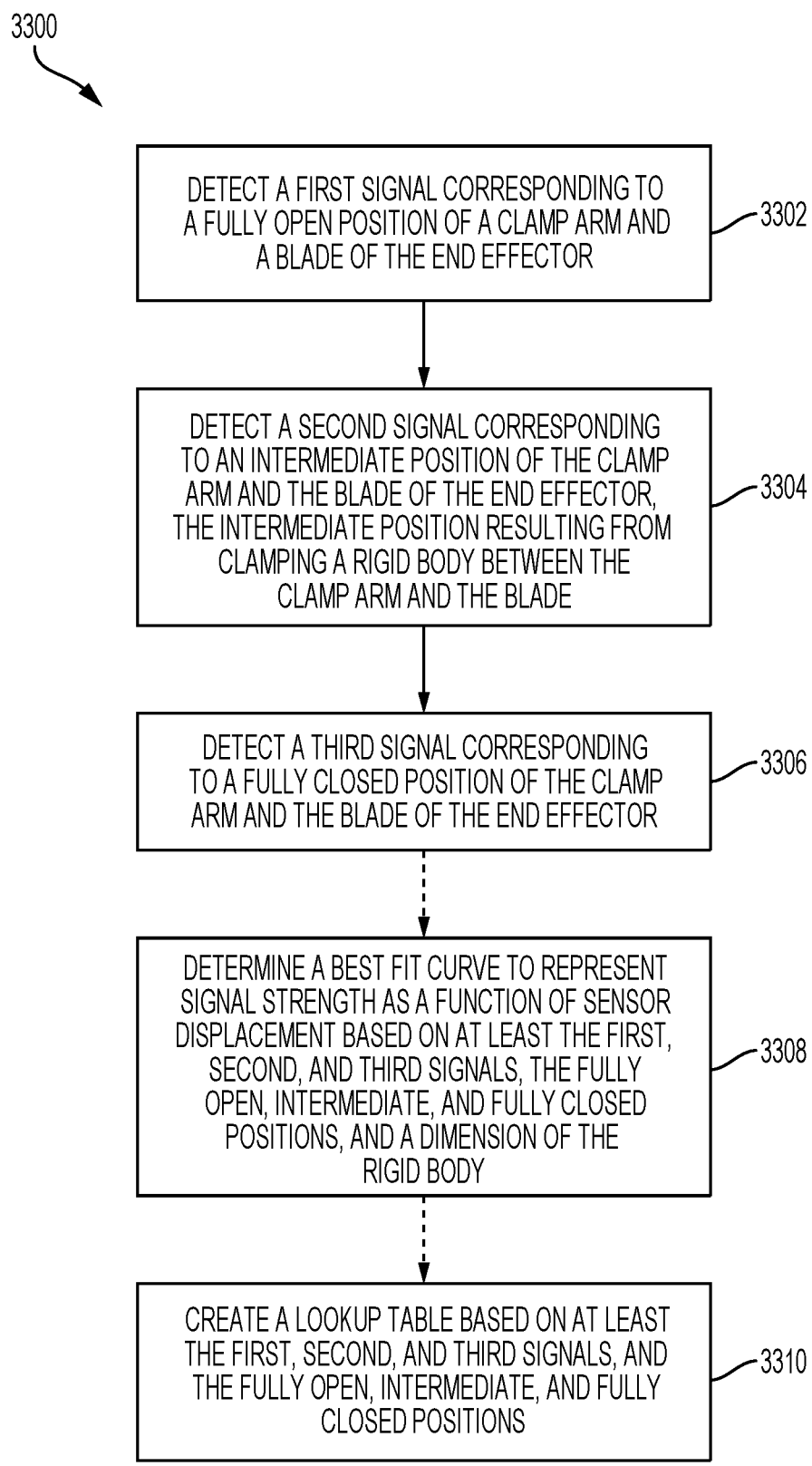
FIG. 32 is a logic diagram illustrating an example process for calibrating an apparatus for controlling for an end effector in accordance with one aspect of the present disclosure.

In one aspect, a method and/or apparatus may provide functionality for sensing a clamp arm position relative to a ultrasonic blade of an end effector, and a generator such as generator 102 and a controller such as control circuit 108 and/or controller 196 may be used to adjust a power output to the ultrasonic blade based on the clamp arm position. Referring now to FIG. 32, a process 3200 for controlling an end effector is shown. The process 3200 may be executed at least in part by a processor which may be in communication with or may be part of one or more of generator 102, control circuit 108, and/or controller 196. Referring now to FIG. 32, a process 3300 for calibrating a controller for an end effector is shown. The process 3200 may be executed at least in part by a processor which may be in communication with or may be part of one or more of generator 102, control circuit 108, and/or controller 196.

Figure 11:
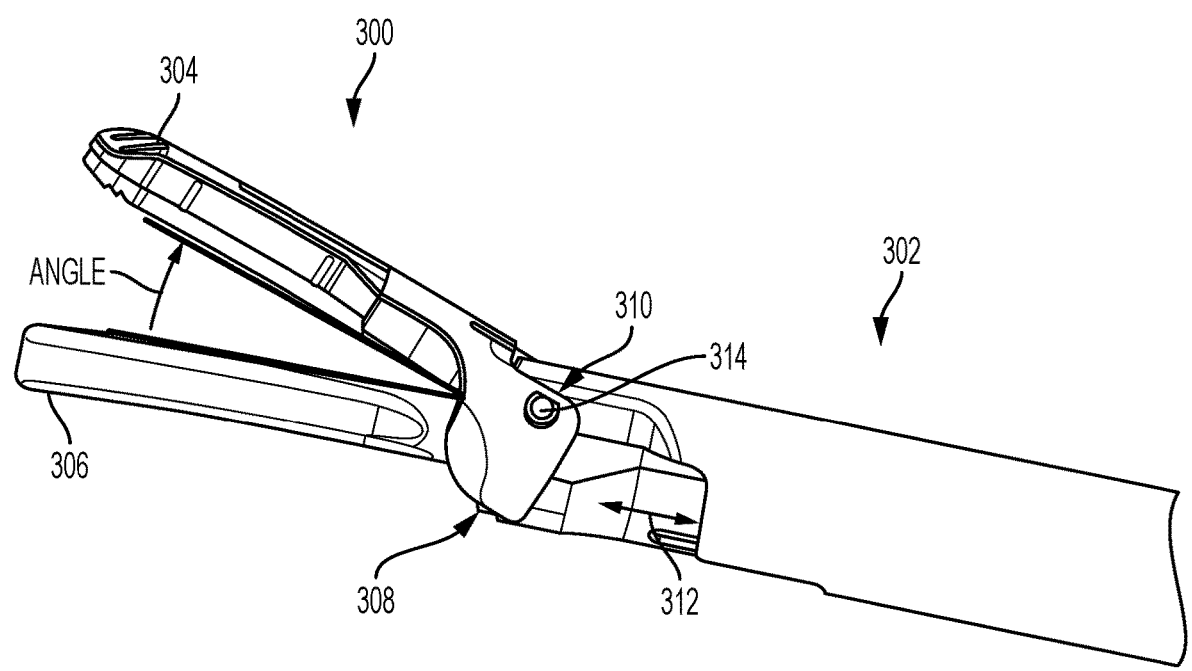
FIG. 11 illustrates an example end effectors and shaft of a surgical instrument in accordance with one aspect of the present disclosure.

Referring now to FIG. 11, an example end effector 300 and shaft 302 are shown. The clamp arm 304 may have a position (e.g., represented by the "angle" arrow or a displacement) relative to the ultrasonic blade 306, which may be measured using one or more sensors such as Hall-effect sensor. Sensing the position of the clamp arm relative to the ultrasonic blade may provide relevant device information enabling new capabilities such as the ability to sense thickness, quantity, or types of tissues clamped inside the jaws. In one aspect, the process 3200 of FIG. 32 may determine 3220 a type of tissue between the clamp arm and the ultrasonic blade based on a signal (from, e.g., a Hall-effect sensor). Further, using a processor and/or memory, one or more algorithms (e.g., for sealing a vessel without transection) may be chosen based on the thickness, quantity, or type of tissue determined to be clamped inside the jaws.

Ultrasonic blade 306 may deliver a tissue effect through mechanical vibration to tissues and/or blood vessels. Clamp arm 304 may pivot about point 314, which may represent a connection between the clamp arm and an outer tube 310. An inner tube 308 may move back and forth and may drive closure of the clamp arm 304 on ultrasonic blade 306. In various aspects, it may be desirable to measure the angle between the clamp arm 304 and the ultrasonic blade 306.

In one aspect, the position of clamp arm 304 relative to ultrasonic blade 306 (e.g., during activation) may be approximated through a coupling with the inner tube 308. The inner tube 308 may be linked to the clamp arm 304 and may be similar to the reciprocating tubular actuating member 58 located within the outer tubular sheath 56. The outer tube 310, which may be similar to the outer tubular sheath 56, and/or ultrasonic blade 306, may be used to determine a position and/or angle of the clamp arm 304 relative to ultrasonic blade 306. The outer tube 310 may be static and in one aspect may be linked to clamp arm 304. As result, using the techniques and features described herein, the movement (e.g., represented with the bidirectional arrow 312) of the inner tube 308 relative to the outer tube 310 may be measured and used to approximate the claim arm position.

Referring briefly to FIG. 32, process 3200 may detect 3202 a signal (e.g., at a Hall-effect sensor) in response to movement of a first tube relative to a second tube, the first tube driving movement of a clamp arm of the end effector. The first tube may be, for example, similar to reciprocating tubular actuating member 58 and the second tube may be, for example, similar to outer tubular sheath 56. In other words, as described in FIG. 32, the first tube may be an inner tube and the second tube is an outer tube. The inner tube may be moveable 3208 relative to the outer tube. The outer tube may be static relative to the inner tube. The process 3200 may detect 3210 the signal using a Hall-effect sensor and a magnet positioned on the first tube.

Use of Hall-effect sensors will be described herein with respect to various aspects of the present disclosure, however other types of sensors may be used to measure the movement 312. For example, linear variable differential transformers (LVDT), rotary variable differential transformer, piezoelectric transducers, potentiometers, photo electric sensors may be used to measure the movement 312. Furthermore, Hall-effect sensors and suitable equivalents may be used to measure the position of two bodies relative to one another through the use of a small electronic board and magnets.

Figure 12:
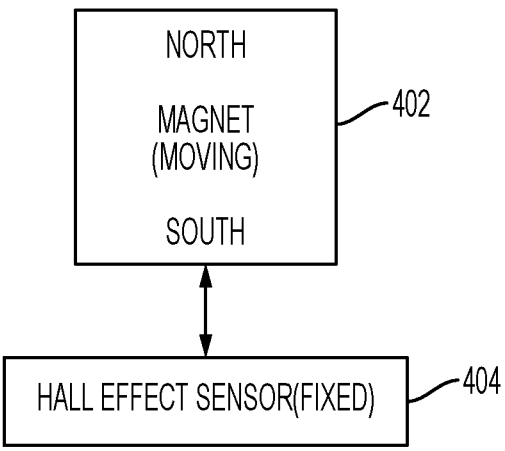
FIG. 12 illustrates an example Hall-effect sensor and magnet configuration in accordance with one aspect of the present disclosure where the Hall-effect sensor is fixed and the magnet moves in a line perpendicular to the face of the Hall sensor.
Figures 13A, 13B:
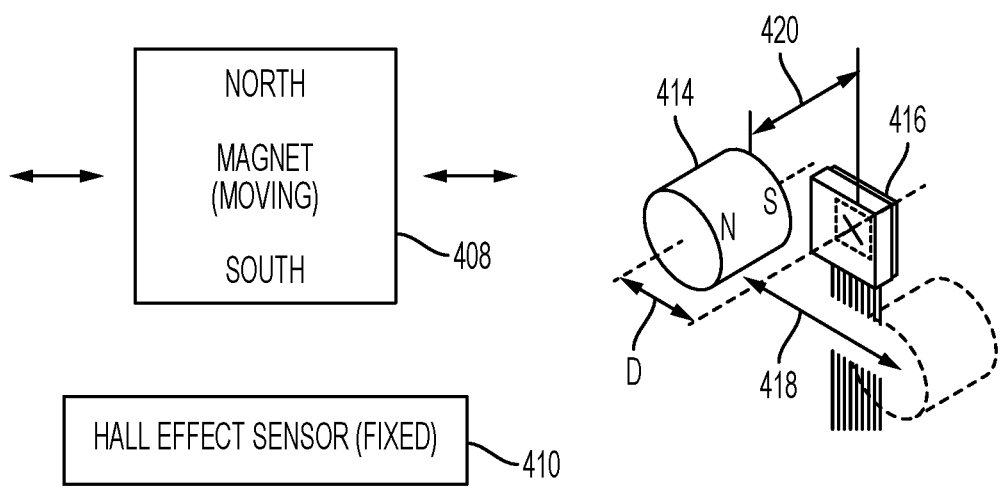
FIG. 13A illustrates an example Hall-effect sensor and magnet configuration in accordance with one aspect of the present disclosure where the Hall-effect sensor is fixed and the magnet moves in a line parallel to the face of the Hall-effect sensor.
FIG. 13B illustrates an example Hall-effect sensor and magnet configuration in accordance with one aspect of the present disclosure where the Hall-effect sensor is fixed and the magnet moves in a line parallel to the face of the Hall-effect sensor.

Referring now to FIG. 12, a representation of an example Hall-effect sensor is shown. A magnet 402 may have north and south poles which move in a line perpendicular to the face of the Hall sensor 404, which may be in a fixed position. Referring now to FIG. 13A, another representation of an example Hall-effect sensor is shown. A magnet 408 may have north and south poles moving in a line parallel to the face of the Hall-effect sensor 410, which may be in a fixed position. Referring now to FIG. 13B, another representation of an example Hall-effect sensor is shown. A magnet 414 may have north and south poles moving in a line (418) parallel to the face of the Hall-effect sensor 416, which may be in a fixed position. The magnet may have diameter D and the magnet and Hall-effect sensor 416 may have total effective air gap (TEAG) 420. This configuration may allow for a very sensitive measurement of movement over small distances with the appropriate magnet-sensor combination.

The Hall-effect sensor may include a small electronic chip which may sense magnetic fields and change its electrical output based on the relative proximity of the magnet or the strength of the magnetic fields to the Hall-effect sensor. As the magnet moves across the face of the Hall-effect sensor (e.g., marked "X") and gets closer to being directly in front of the face, an output signal of the Hall-effect sensor may change and be used to determine a position of the magnet relative to the Hall-effect sensor. In one aspect, the magnet may not cause much of a change in the output signal of the Hall-effect sensor. For example, using a magnet and Hall-effect sensor having particular characteristics, the magnet being more than 1.5 inches or further distances from the Hall-effect sensor may produce very little in terms of the output signal, but as the magnet moves closer and closer to the Hall-effect sensor, the electrical output changes more rapidly such that a very discernable signal change occurs in response to small motions of the magnet as it is moved closer to a critical position. The electrical response of the Hall-effect sensor at various positions of the magnet may be used to create a best fit curve. For example, the voltage output of the Hall-effect sensor as a function of the displacement of the magnet may be determined.

Figure 14A:
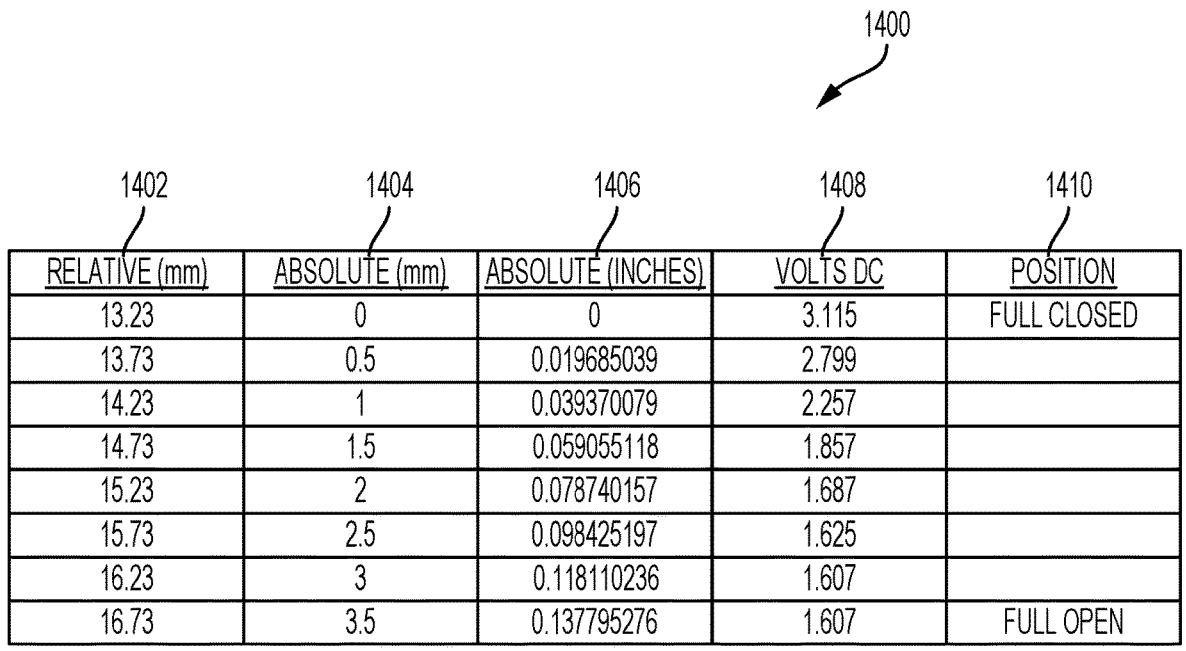
FIG. 14A is a table of output voltage of a Hall-effect sensor as a function of distance as a clamp arm moves from a fully closed position to a fully open position in accordance with one aspect the present disclosure.

FIG. 14A is a table 1400 of output voltage of a Hall-effect sensor as a function of distance as a clamp arm moves from a fully closed position to a fully open position in accordance with the present disclosure. Relative distance (mm) is listed in the first column 1402. Absolute distance (mm) is listed in the second column 1404 and absolute distance in inches is listed in the third column 1406. Output voltage of the Hall-effect sensor is listed in the fourth column 1408 and clamp arm position is listed in the fifth column 1410, where the uppermost cell indicates the clamp arm in the fully closed position and the lowermost cell indicates the clamp arm in the fully open position.

Figure 14B:
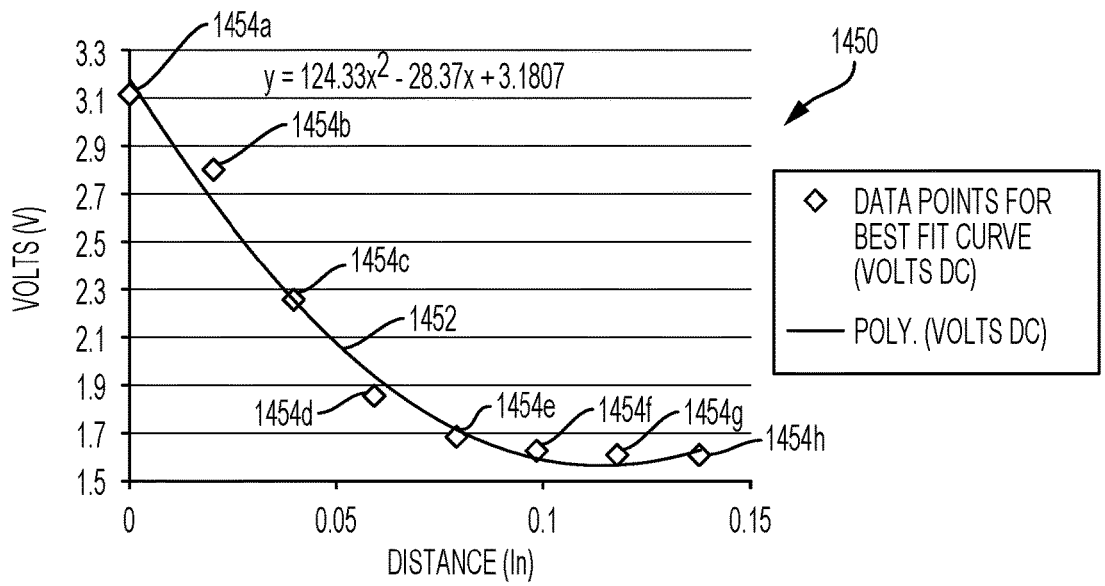
FIG. 14B is a graph of output voltage of a Hall-effect sensor as a function of distance as a clamp arm moves from a fully closed position to a fully open position in accordance with one aspect the present disclosure.

Referring now to FIGS. 14A and 14B, a table 1400 and a graph 1450 of the output voltage of a Hall-effect sensor (y-axis) as a function of the displacement (x-axis) and related data are shown. In this example, the sensitivity of a prototyped Hall-effect sensor/magnet combination is shown as a relatively small linear movement (e.g., 0.100") may result in a 1.5 volts signal change. This signal change may be read by a generator (e.g., generator 102) and used to make determinations about ultrasonic blade displacement, or provide auditory, tactile and/or other feedback to a user (e.g., via speaker 114 and/or visual display 116). A best fit curve 1452 may be determined from the plotted data points 145a-h (e.g., one or more of relative displacement, absolute displacement, voltage output, and position) and a polynomial equation for output voltage of the Hall-effect sensor (y-axis) as a function of the displacement (x-axis) of the magnet may result. The best fit curve may be of the 2nd, 3rd, 4th . . . nth order. The data points 1454a-h and/or the best fit curve 1452 may be used to create a lookup table stored in a memory and/or the resulting equation may be executed in a processor in order to determine, for example, a displacement for the magnet (and a corresponding clamp arm position) given a specific output voltage of the Hall-effect sensor. In this way, turning briefly to FIG. 32, the process 3200 may determine 3204 a clamp arm position of the end effector relative to a ultrasonic blade of the end effector based on the signal (from, e.g., Hall-effect sensor voltage output).

Figure 15A:
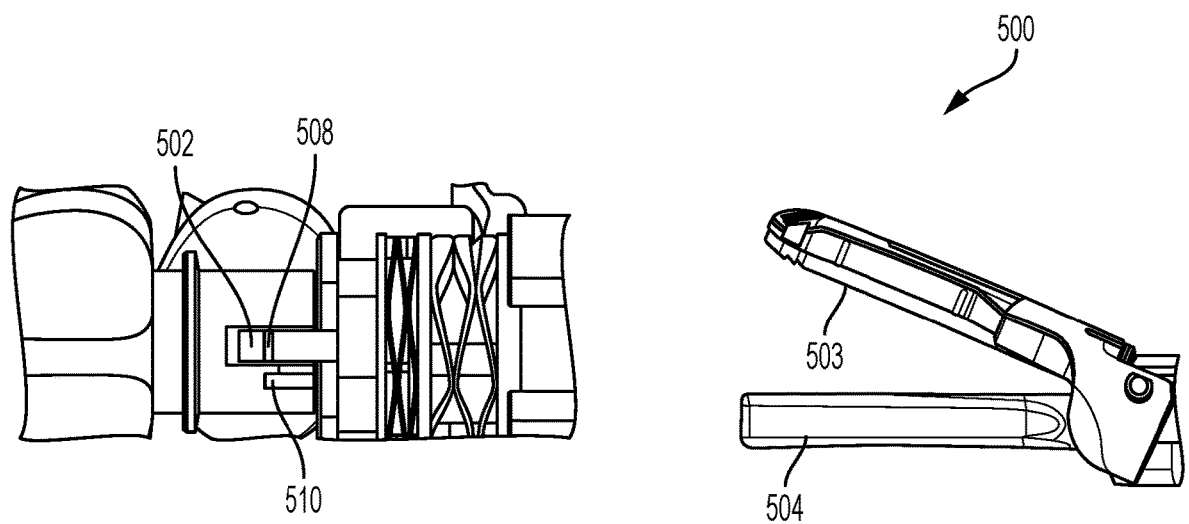
FIG. 15A is a top view of a Hall-effect sensor and magnet configurations in a surgical instrument and corresponding open jaws end effector position in accordance with one aspect of the present disclosure.
Figure 15B:
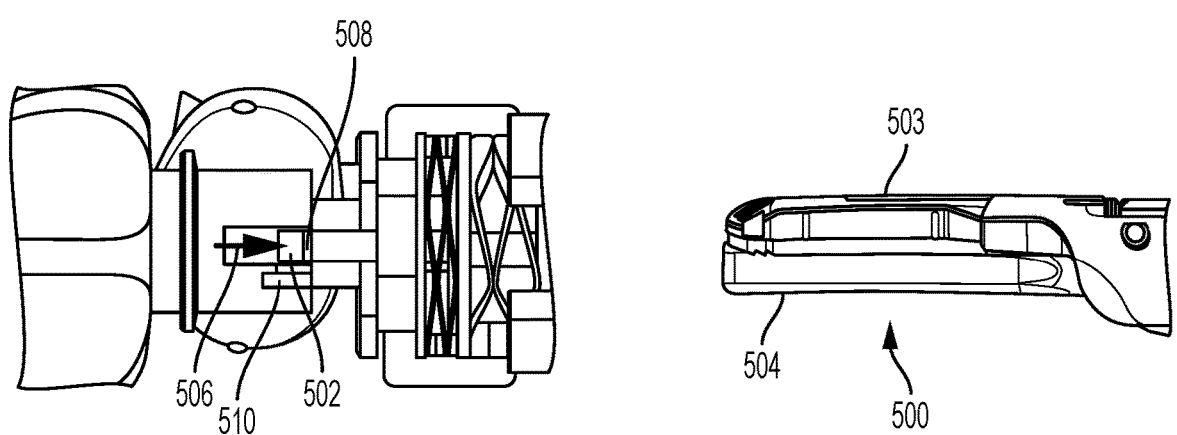
FIG. 15B is a top view of a Hall-effect sensor and magnet configurations in a surgical instrument and corresponding closed jaws end effector position in accordance with one aspect of the present disclosure.

Turning now to FIG. 15A there is shown a top view of a Hall-effect sensor 510 and magnet 508 configurations in a surgical instrument and corresponding open jaws end effector 500 position in accordance with one aspect of the present disclosure and FIG. 15B is a top view of the Hall-effect sensor 510 and magnet 508 configurations in a surgical instrument and corresponding closed jaws end effector 500 position in accordance with one aspect of the present disclosure. In one aspect, as shown in FIGS. 15A and 15B, the voltage output of the Hall-effect sensor 50 is 1.6 VDC when the jaws of the end effector 500 are open and 3.1 VDC when the jaws of the end effector 500 are closed.

Referring now to FIGS. 15A and 15B, one aspect of a Hall-effect sensor 510 and magnet 508 combination are shown as implemented in a surgical device such as one or more of those discussed herein. FIGS. 15A and 15B show two images of top-down views of the example. An inner threaded collar 502 may be attached to a magnet 508. As a trigger of the surgical device is closed, a clamp arm 504 of the end effector 500 comes into closer contact with a ultrasonic blade 504, and the magnet 508 moves further proximal as shown in the top-down views. As the magnet 508 moves (in a direction indicated by arrow 506), the voltage potential of the Hall-effect sensor 510 changes. The magnet 508 positioned on the first tube relative to the Hall-effect sensor 510 may move as the first tube drives movement of the clamp arm 503 of the end effector 500.

It should be noted that while various aspects discussed herein are described to include an outer tube that is static and an inner tube that drives motion of the clamp arm, other configurations are possible and within the scope of the present disclosure. For example, in various aspects, an outer tube may drive the motion of the clamp arm and the inner tube may be static. Additionally, while various aspects discussed herein are described to include a Hall-effect sensor 510 and/or integrated circuit (e.g., chip) that is static and a magnet 508 that moves as the clamp arm 500 moves, other configurations are possible and within the scope of the present disclosure. For example, in various aspects, the Hall-effect sensor 510 may move as the clamp arm 503 moves and the magnet may be static. Many combinations are possible, including a fixed outer tube and a moveable inner, a moving magnet 508 and a stationery Hall-effect sensor 510 or other sensing circuit, a moving Hall-effect sensor 510 or other sensing circuit and a stationary magnet 508, a moveable outer tube and a fixed inner tube, a fixed magnet in one of the inner and outer tubes, and/or a moving magnet in one of the inner and outer tubes. The Hall-effect sensor 510 or other circuit may be mounted to the moving part (e.g., inner or outer tube) or mounted to the stationary part (e.g., inner or outer tube), as long as flexible electrical connections are considered and motion can be achieved.

As shown in FIG. 15A, the inner threaded collar 502 with attached magnet 508 is positioned further left than in FIG. 15B, and the corresponding end effector 500 has an open jaw, e.g., open clamp arm 503. As the user pulls the trigger and closes the end effector 500, multiple springs and the inner threaded collar 502 move (in the direction indicated by arrow 506) the clamp arm 503 is driven closed or is driven to grafting tissue captured in between the clamp arm 503 and the ultrasonic blade 504. A Hall-effect sensor 510 and a magnet 508 is shown, which may be cylindrical, moves over the Hall-effect sensor 510, as the clamp arm 503 closes towards the ultrasonic blade 504.

Figure 16:
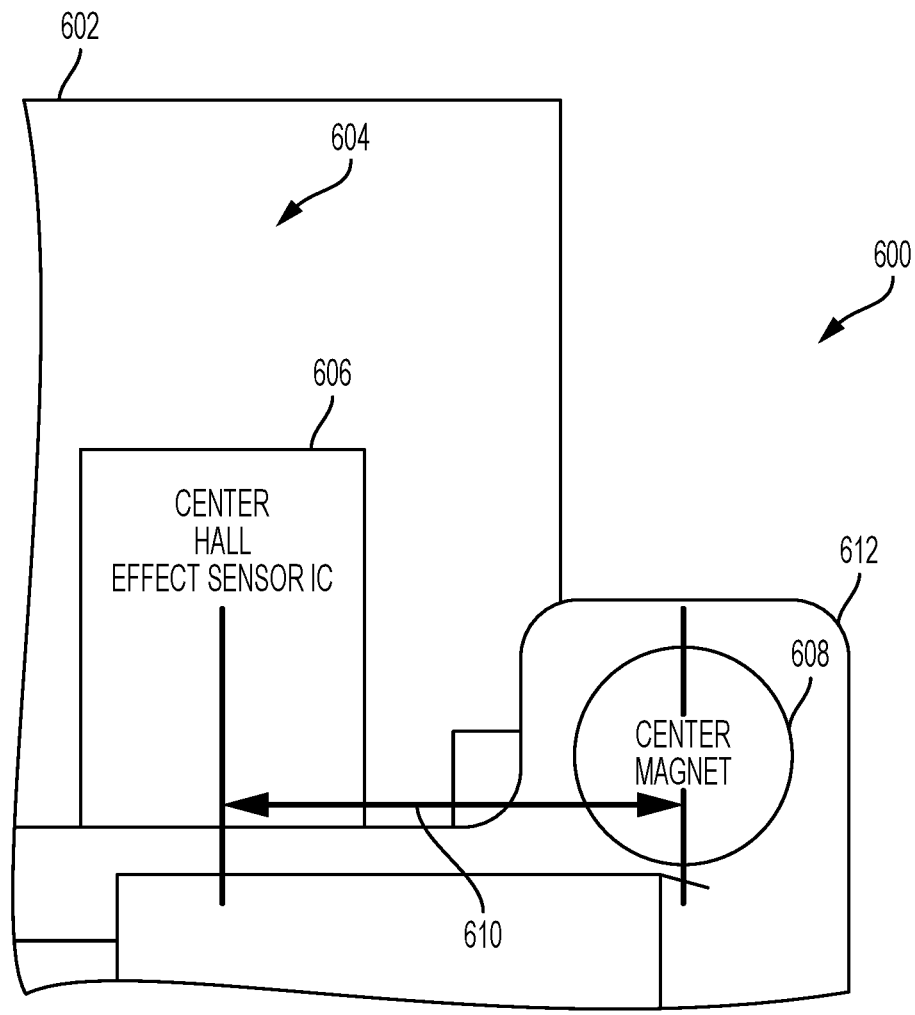
FIG. 16 illustrates a plan view of a system comprising a Hall-effect sensor and magnet configuration in a surgical instrument in accordance with one aspect of the present disclosure.

Referring now to FIG. 16, there is shown a plan view of a system 600 comprising a Hall-effect sensor 602 and magnet 606 arrangement. The Hall-effect sensor 602 includes a circuit board 604 and an integrated circuit 606. The magnet 608 moves back and forth along line 610 as the clamp arm is closed and opened. As the magnet 608 moves towards the center of the Hall effect integrated circuit 606 the sensitivity of the Hall-effect sensor 602 changes and the output signal increases. A carrier 612 for the magnet 608 may be coupled to the inner tube that drives the clamp arm. In one aspect, as the inner tube is pulled towards the handle of the surgical instrument (e.g., by the trigger), the jaw closes (e.g., clamp arm) closes. The magnet 608 is connected to an extended leg of the threaded inner collar of the outer tube.

Figure 17A:
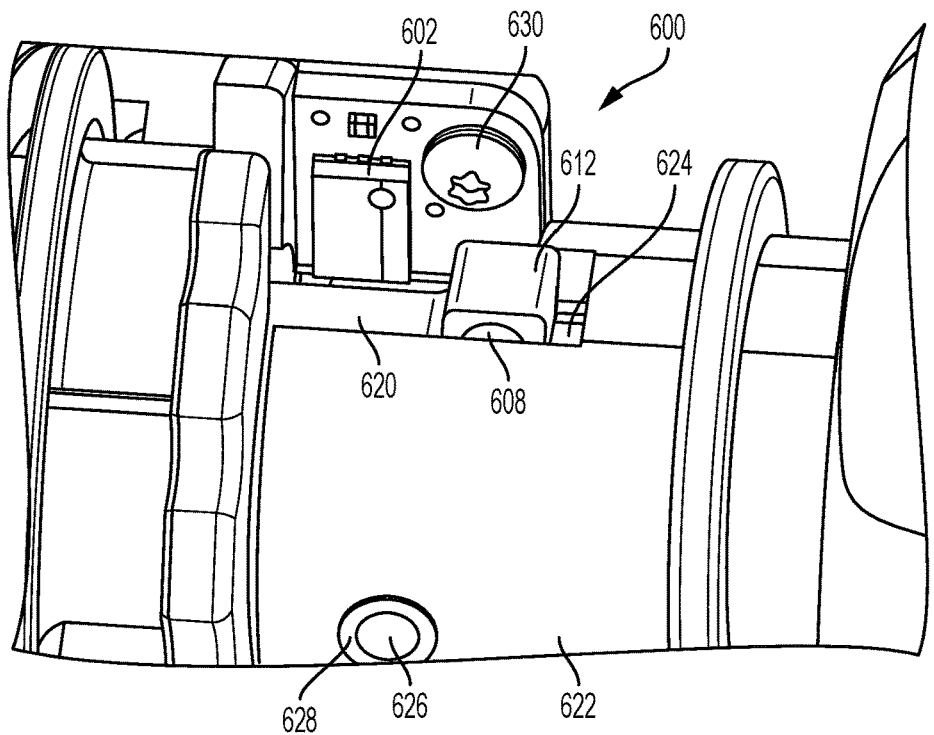
FIG. 17A illustrates a view of an Hall-effect sensor and magnet configurations in the context of a surgical instrument in accordance with one aspect of the present disclosure.
Figure 17B:
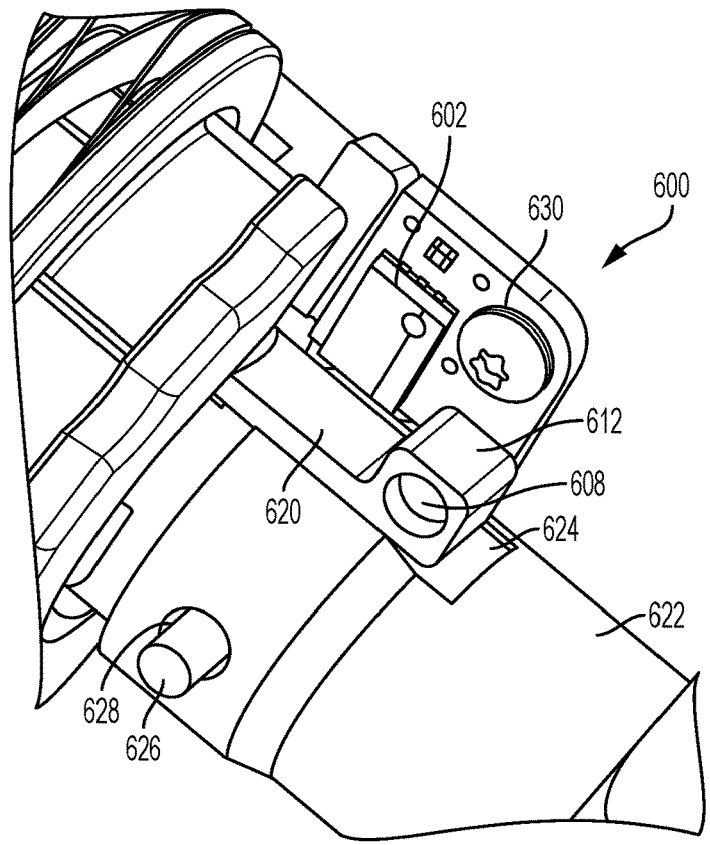
FIG. 17B illustrates a view of an Hall-effect sensor and magnet configurations in the context of a surgical instrument in accordance with one aspect of the present disclosure.

FIGS. 17A and 17B illustrates different views of the system 600 comprising a Hall-effect sensor 602 and magnet 608 configurations in the context of a surgical instrument in accordance with one aspect of the present disclosure. With reference to FIGS. 17A and 17B, the Hall-effect sensor 602 is shown positioned within a surgical instrument. The Hall-effect sensor 602 is positioned on the threaded inner collar 620 of the outer tube 622. A slot 624 is defined in a rotation knob of the outer tube 622 to allow the magnet 608 to travel. The magnet 608 is positioned within the carrier 612, which is slidably movable within the slot 624. For example, the Hall-effect sensor 602 as described herein may be static and is attached to a rotation knob such that it can rotate around the centerline of the ultrasonic blade. A pin 626 may be positioned within an aperture 628 through both the rotation knob and the Hall-effect sensor 602 and through a center ultrasonic blade portion. As a result, the ultrasonic blade does not move axially, but the inner tube is able to move axially right and left of the pin 626. A threaded connection 630 is made of nylon or any other suitable material with minimum magnetic flux.

Figure 18:
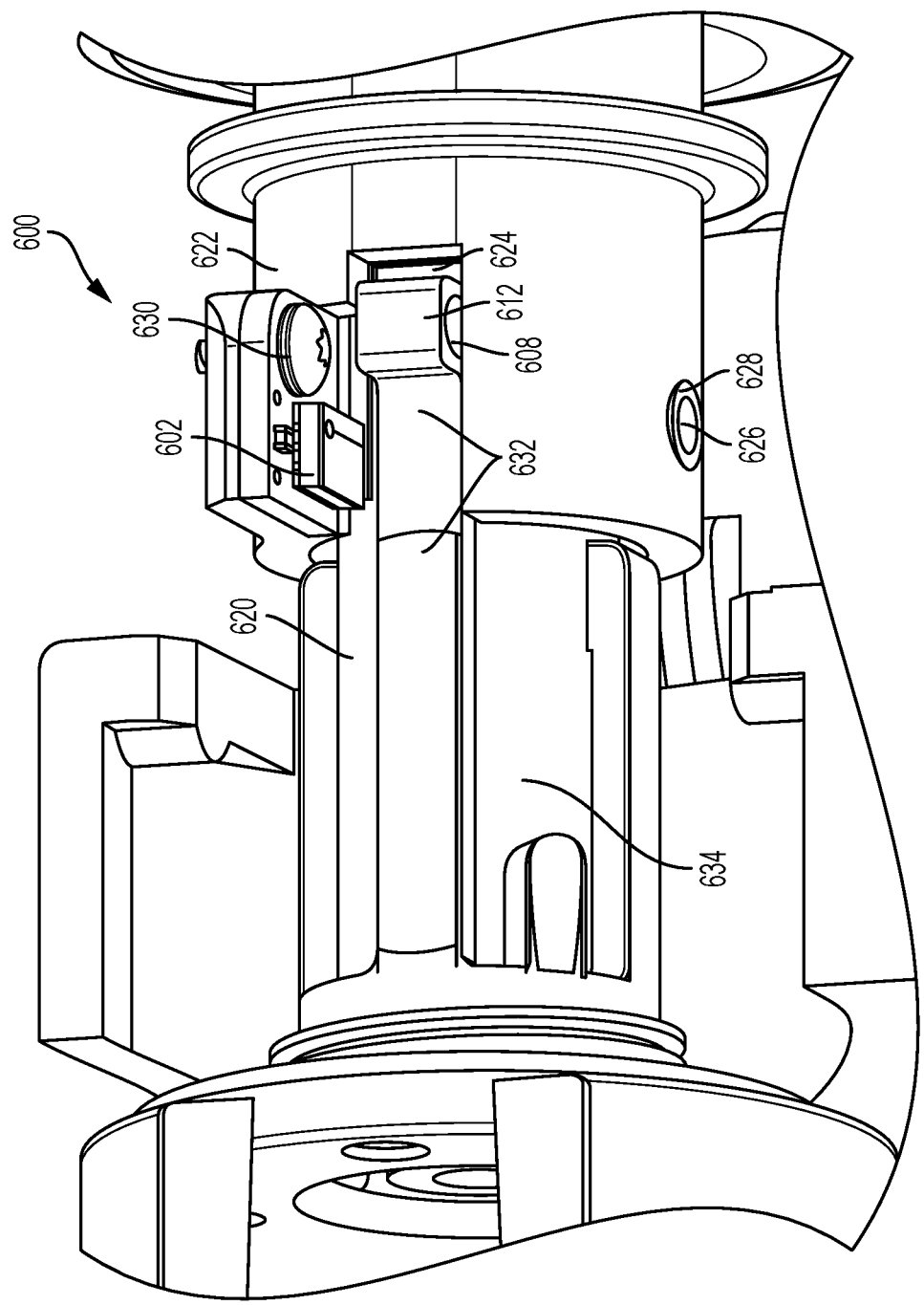
FIG. 18 illustrates a Hall-effect sensor and magnet configuration in a surgical instrument in accordance with one aspect of the present disclosure.

FIG. 18 illustrates a Hall-effect sensor 602 and magnet 608 configuration in the context of a surgical instrument in accordance with the present disclosure. Referring now to FIG. 18, a shaft of a surgical instrument is shown and the magnet 608 is positioned within the carrier 612. A magnet movement 632 is coupled to the inner tube 634. The magnet 608 may be coupled with snap fits to a threaded collar 638 of the inner tube 634. The Hall-effect sensor 602 as described herein is static and is attached to a rotation knob such that it can rotate around the centerline of the ultrasonic blade.

Figure 19A:
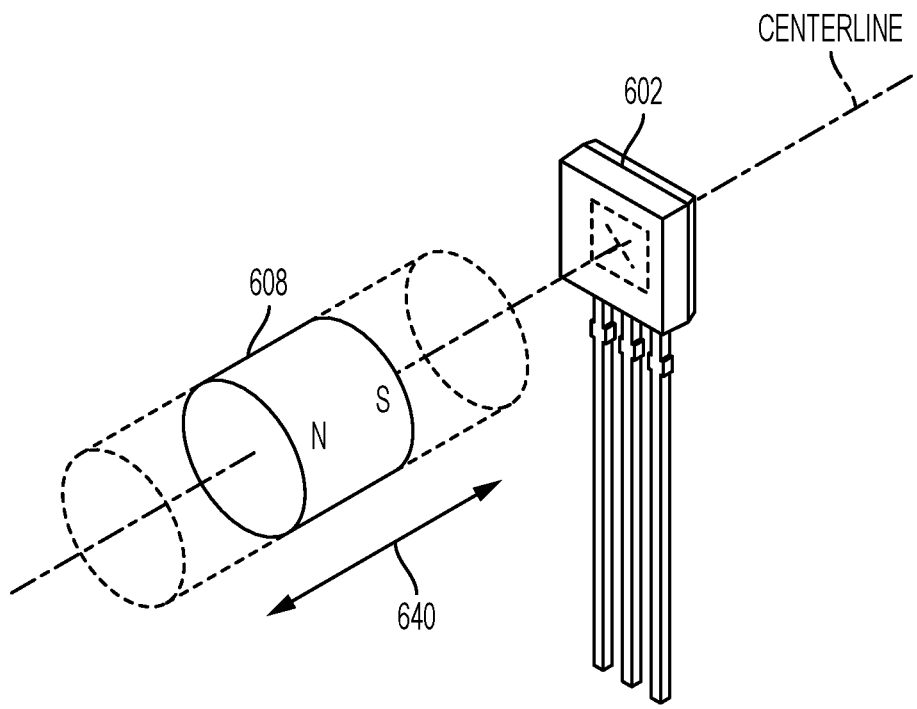
FIG. 19A illustrates a Hall-effect sensor and magnet configuration in accordance with one aspect of the present disclosure.
Figure 19B:
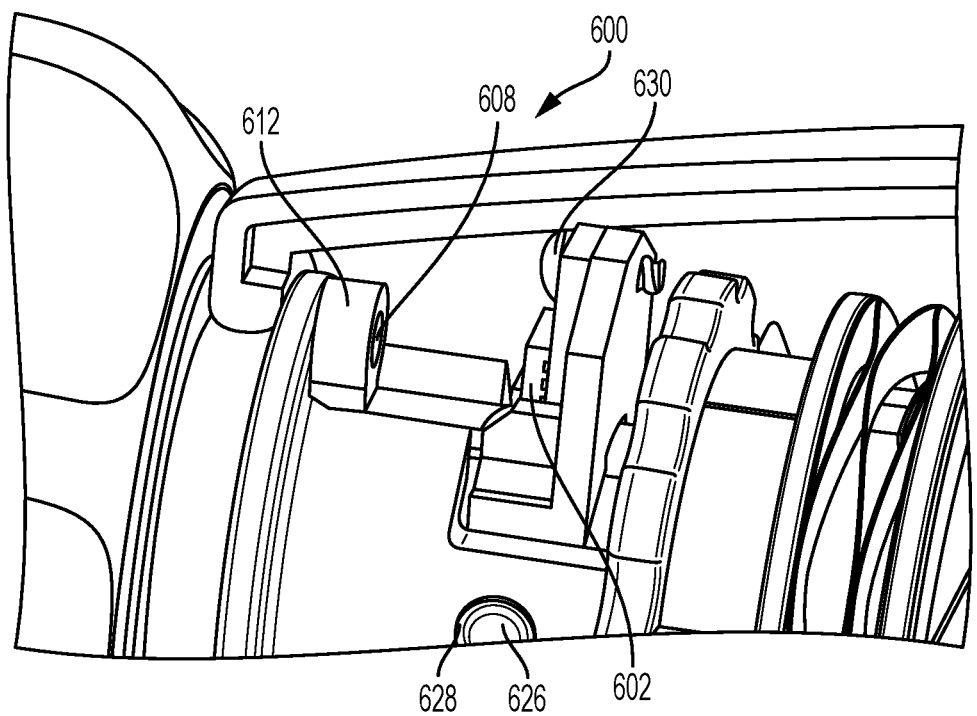
FIG. 19B illustrates Hall-effect sensor and magnet configurations in a surgical instrument in accordance with one aspect of the present disclosure.

FIG. 19A illustrates a Hall-effect sensor 602 and magnet 608 configuration in accordance with one aspect of the present disclosure. FIG. 19B is a detailed view of the Hall-effect sensor 602 and magnet 608 configuration in the context of a surgical instrument in accordance with the present disclosure. Referring now to FIGS. 19A and 19B, in one aspect the Hall-effect sensor 602 and magnet 608 configuration is located on a shaft of a surgical instrument. In one aspect, the pole faces of the magnet 608 and the Hall-effect sensor 602 move in line with one another. In FIGS. 17A, 17B, 19A, and 19B, the Hall-effect sensor 602 is stationary while the magnet 608 moves in connection with the clamp arm. In one aspect, the inner threaded collar is configure to carry the magnet 608 and may be directly connected to the inner tube. In this way, the Hall-effect sensor 602 may be positioned in a different way on the rotation knob such that the faces of the magnet 608 and the Hall-effect sensor 602 come together in a perpendicular manner as shown by the motion arrow 640.

In one aspect, an ultrasonic algorithm or process may be used to enable a surgical device to seal tissue without transection. The implementation of this algorithm or process may require measuring clamp arm position relative to the ultrasonic blade of an end effector. A method can be used to sense the clamp arm position relative to the ultrasonic blade as described herein and that positioning can be consistently calibrated during manufacturing, as will be described below, such that estimates of thickness of tissue can be made. For example, an algorithm or process that is fed information about quantity of tissue can react as that quantity changes. This may allow the surgical device to treat the tissue without completely transecting a vessel.

Turning now briefly to FIG. 32, once the clamp arm position relative to ultrasonic blade is known, how the ultrasonic blade vibrates can be adjusted to get different tissue effects. In this way, process 3200 may adjust 3206 a power output to the ultrasonic blade of the end effector based on the clamp arm position. For example, process 3200 may adjust 3214 the power output to the ultrasonic blade of the end effector using an ultrasonic transducer based on a voltage change in a Hall-effect sensor.

Typically, end effectors may be used to coagulate and cuts vessels at the same time. However, using the techniques and features described herein, an end effector may be used to seal a carotid or vessel without actually transecting it, as may be desired by a surgeon. With information on the clamp arm position, a Travel Ratio (TR) can be calculated, whereby if the clamp arm is in the completely closed position with nothing captured in the end effector, the sensor (e.g., Hall-effect sensor) may indicate a TR of 1. For example, for illustrative purposes only, let XT represent a relative clamp arm position at any given time in activation, X1 be a claim arm position when the surgical device is fully clamped with no tissue, and X2 be a clamp arm position at a beginning of activation, with tissue grasped in the end effector, where:

$$TR = \frac{X1 - XT}{X1 - X2}$$

Continuing with the example above, X1 may be a value programmed into the surgical device for the clamp arm position when the jaws are fully closed and nothing is captured in the end effector. X2 may be the clamp arm position at the start of an activation such that if a vessel is attached in the end effector and the clamp arm is closed all the way, the clamp arm may be squeezing the vessel down but with some distance to travel before the vessel is transected and the clamp arm is directly opposite the ultrasonic blade with full contact. XT may change dynamically as it is the clamp arm position at any given time.

For example, at the very beginning of activation TR may be zero, as X1 may be set to represent the clamp arm position being fully closed with nothing captured. X2, at the very beginning of the activation, when the clamp arm is touching a vessel, may provide a relative thickness before firing the ultrasonic blade. XT may be the value in the equation that is updating continuously with time as the clamp arm travels further and compresses and starts to cut the tissue. In one aspect, it may be desirable to deactivate (e.g., stop firing) the ultrasonic blade when the clamp arm has traveled 70% or 0.7. Thus, it may be empirically determined beforehand that a desired TR is 0.7 of the way between the clamp arm being closed with a full bite of tissue and being fully closed with nothing in between the clamp arm and ultrasonic blade.

Figure 20:
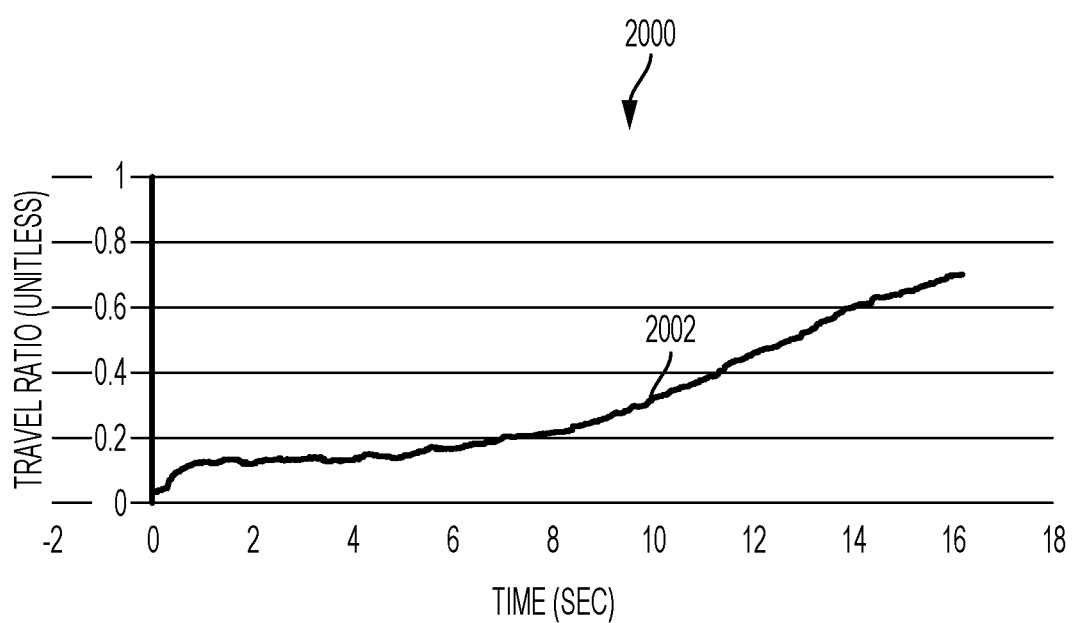
FIG. 20 is a graph of a curve depicting Travel Ratio (TR) along the y-axis, based on Hall-effect sensor output voltage, as a function of Time (Sec) along the x-axis in accordance with one aspect of the present disclosure.

The TR of 0.7 has been described for illustrative purposes only and may depend on many parameters. For example, the desired TR for the point at which the ultrasonic blade will be shut-off may be based on vessel size. The TR may be any value observed to work for treating a given tissue or vessel without transection. Once the desired position is known, the vibrating of the ultrasonic blade may be adjusted based on the desired position. FIG. 20 is a graph 2000 of a curve 2002 depicting Travel Ratio (TR) along the y-axis, based on Hall-effect sensor output voltage, as a function of Time (Sec) along the x-axis. As shown in FIG. 20, the desired TR is 0.7, meaning that the ultrasonic blade is deactivated (e.g., stop firing) when the clamp arm has traveled 70% or 0.7. This is relative to a clamp arm on a vessel with a ultrasonic blade firing where the desired end TR was 0.7. In the particular example of FIG. 20, the ultrasonic blade was activated (e.g., firing) on a carotid and shut off at the TR of 0.7 after about 16 seconds.

Figure 21:
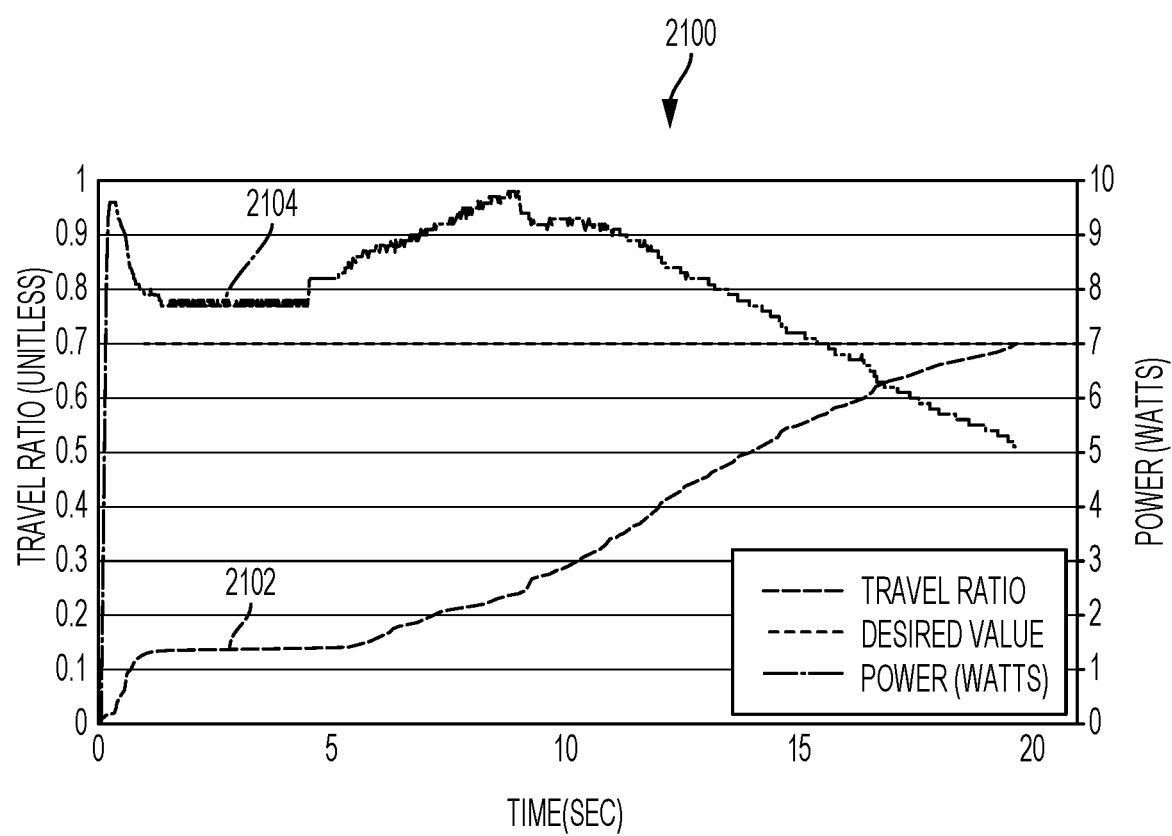
FIG. 21 illustrates a graph of a first curve depicting Travel Ratio (TR) along the left y-axis, based on Hall-effect sensor output voltage, as a function of Time (Sec) along the x-axis in accordance with one aspect of the present disclosure.

In one aspect, it may be desirable to use a proportional-integral controller. FIG. 21 is a graph 2100 of a first curve 2102 depicting Travel Ratio (TR) along the left y-axis, based on Hall-effect sensor output voltage, as a function of Time (Sec) along the x-axis. A second curve 2104 depicts Power (Watts) along the right y-axis as a function of Time (Sec) along the x-axis. The graph 2100 provides an example of what can be accomplished with a proportional-integral (PI) controller. The Travel Ratio (TR) curve 2102 is represented on the graph 2100 by the line marked "TRAVEL RATIO." The goal or Desired Value for the Travel Ratio may be 0.7, as shown by the line marked "DESIRED VALUE," although various other values may be used. The Power output curve 2104 represents power through the ultrasonic blade and is shown and marked "POWER (WATTS)."

Turning now briefly to FIG. 32, there is shown the process 3200 may adjust 3216 the power output to the ultrasonic blade of the end effector dynamically, based on the travel ratio that changes as the clamp arm approaches the ultrasonic blade. For example, as the clamp arm moves towards the ultrasonic blade and the Desired Value is approached, the amount of power output to the ultrasonic blade and into the tissue may be reduced. This is because the ultrasonic blade will cut the tissue with enough power. However, if the power being output is reduced over time as the Desired Value is approached (where a full transection may be represented by a Travel Ratio of 1), the chance that the tissue is transected may be drastically reduced. In this way, effective sealing may be achieved without cutting the tissue as may be desired by the surgeon.

Turning back to FIG. 21, there is shown the Power output curve 2104 shown in FIG. 21 may represent the power applied with a drive signal to a transducer stack to activate (e.g., fire) the ultrasonic blade. The Power value may be proportional to the movement of the clamp arm portion of the end effector and delivered to the tissue and the Power curve may represent voltage and current applied to the ultrasonic transducer. In one aspect, the ultrasonic generator (e.g., generator 102) may read the voltage output data from the Hall-effect sensor and, in response, send commands for how much voltage and current to provide to the transducer to drive the ultrasonic blade as desired. As the clamp arm portion of the end effector is moved and the desired value is approached, the ultrasonic blade may be forced to deliver less energy to the tissue and reduce the likelihood of cutting the tissue.

As the ultrasonic blade is powered, the ultrasonic blade will effect the tissue or the vessel such that friction at the interface of the ultrasonic blade and the tissue causes heat to drive the moisture from and dry out the tissue. During this process, the clamp arm portion is able to increasingly compress the tissue as the seal develops. As the TR increases over time the tissue flattens by applying more pressure with the clamp arm as the tissue dries out. In this way, a PI controller may be used to cook the tissue from a beginning point (where TR=0) to a certain second position by controlling power output to effectively seal large vessels. With the PI controller, as the TR approaches the Desired Value, the ultrasonic device drops the power delivery (to the ultrasonic blade) to smoothly control the compression and coagulation of the tissue. This process has shown an ability to effectively seal vessels without transection. In this way, process 3200 may adjust 3218 the power output to the ultrasonic blade of the end effector dynamically, using a proportional-integral (PI) controller, based on a travel ratio that changes as the clamp arm approaches the ultrasonic blade. It will be appreciated that PI control is not the only logic system through which power could be controlled. Many mathematical mappings exist to appropriately reduce power as a function of the Hall-effect sensor. Examples of other logic systems include PID controllers, proportional controllers, fuzzy logic, neural networks, polynomials, Bayesian networks, among others.

Figure 22:
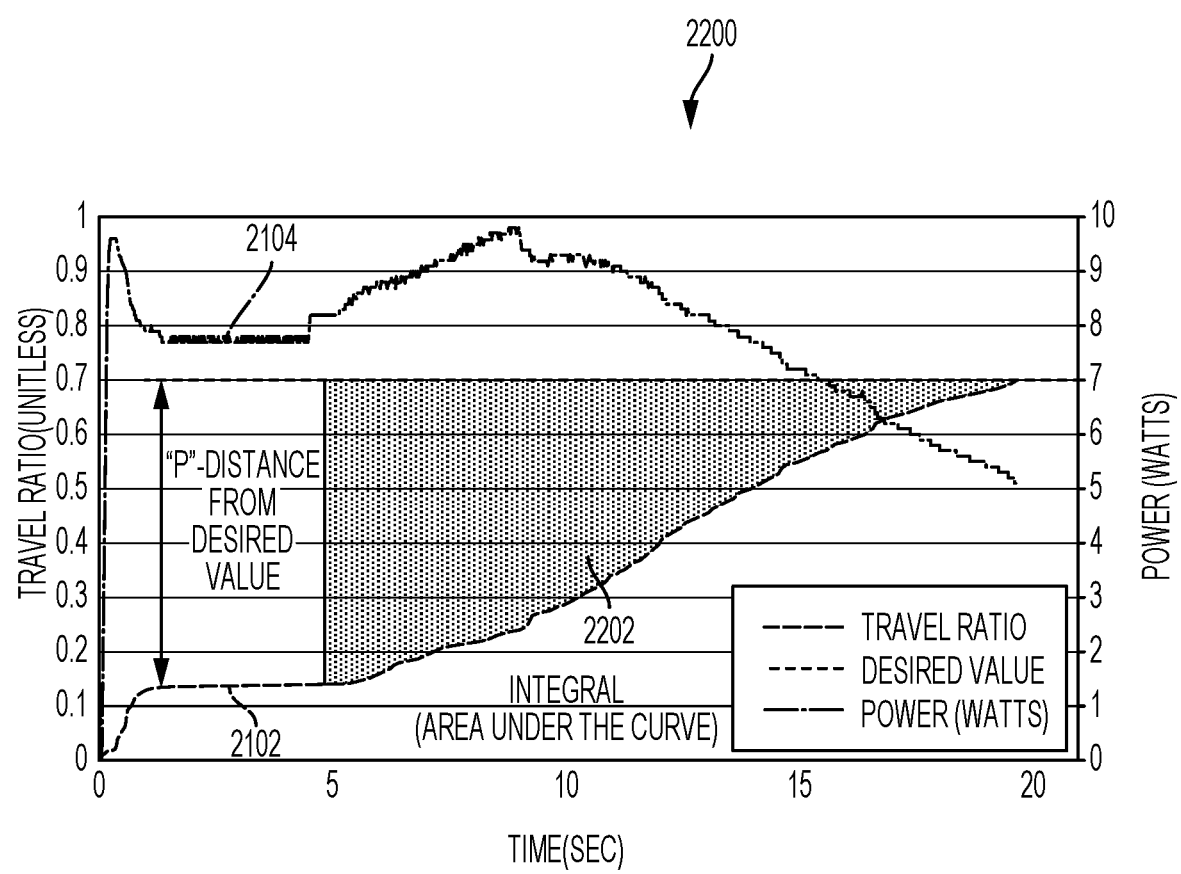
FIG. 22 illustrates charts showing Proportional-Integral control of power output to an ultrasonic blade in accordance with one aspect of the present disclosure.

FIG. 22 is a graph 2200 depicting how the PI controller works. The Proportional term may be an indication of the absolute difference between TR and the Desired Value for TR. TR approaches the Desired Value, the effect of the proportional term may shrink and as a result the ultrasonic power (e.g., delivered by the ultrasonic blade) may be reduced. The Integral term, shown as the area 2202 under the curve, may be an accumulation of error over a give section of time. For example, as shown above, the Integral term may not begin to accumulate until after 5 seconds. After 5 seconds, the Integral term may begin to take effect and the power to the ultrasonic blade may be increased. After about 9 seconds, the reduction of the effect in the Proportional term may outweigh the effect of the increase in the Integral term causing the power delivery to the ultrasonic blade to become reduced. In this example, a Desired Value of 0.7 for the TR was used, however, as discussed above, the TR value may be optimized for a specific device along with the Proportional and Integral terms of the controller.

In effect, the PI controller may indicate what the power output should be based on the distance at any given time between the Travel Ratio and the Desired Value. From that distance, the PI controller may output a certain value (e.g., 0.4). In the example of FIG. 22, at a moment in time (e.g., 1 second) the distance is based on the values assigned to the P and I. This distance may be multiplied it by a constant that represents P and result in 0.78. The generator may instruct the system to send out 0.78 or send out, for example, 7.8 watts of power when the distance between these two is a certain amount. As a result, the TR curve approaches the Desired Value curve, and the distance reduces. Over time, the amount of power the generator tells the system to send decreases, which may be the desired outcome. However, this could also mean that if only P and not I is used, when time approaches 15 seconds, there may not be enough power output to the tissue to complete the goal. This is where the I portion (integral portion) is calculated at a set period of time, which may be about five seconds. By calculating the area 2202 under the curve (shown in FIG. 22 by hashed lines, captured between the Desired Value and Travel Ratio over time) and in addition to the 0.78, shown between 0 and 5 seconds, the I portion starts to add its own amount of power to help the progression of the Travel Ratio to the Desired Value and make sure that it gets there in a somewhat timely manner. For example, at five seconds, the I portion is not active, but as time progresses the I portion starts to calculate the area captured between the two curves and adds that value (e.g., additional four watts) which is the area under the curve, in addition to the power coming from the Proportional value. Using these two calculations together may provide the Power curve (i.e., the power output) as shown in FIG. 22. The PI controller is configured to drive towards the seal effect in a somewhat timely manner.

In one aspect the techniques described herein may be employed to seal different sizes of vessels (e.g., 5 mm, 6 mm, and 7 mm round vessels). The strength of the seals may be tested until the seal bursts and recording the burst pressure. A higher burst pressure indicates a stronger seal. In the case of an actual surgery, if a surgical instrument or device as described herein is used to seal a vessel the seal will not leak if it has a high associated burst pressure. In one aspect, the burst pressures can be measured across different sizes of vessels, e.g., 5 mm, 6 mm, and 7 mm round vessels, respectively. Typically, smaller vessels have higher burst pressure with larger vessels, the burst pressure is decreased.

Figure 23:
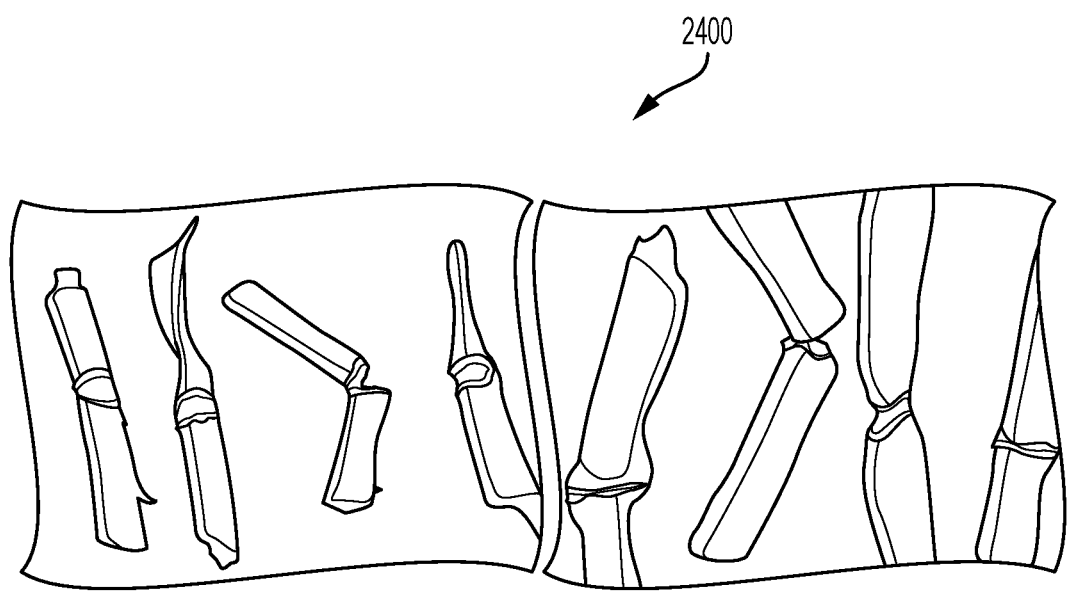
FIG. 23 illustrates several vessels that were sealed using the techniques and features described herein in accordance with one aspect of the present disclosure.

Turning now to FIG. 23, there is shown several vessels 2400 that were sealed using the techniques and features described herein (e.g., using an ultrasonic blade and a Hall-effect sensor). Using the PI controller as described above, 60 vessels were sealed. 58 vessels were sealed without transection.

In one aspect, it has been observed that activating a ultrasonic blade with the clamp arm open may help to release tissue that may have stuck to the ultrasonic blade while being coagulated. Detecting a change in signal from a Hall-effect sensor may indicate when the user is opening the clamp arm after device activation. This information may trigger the system to send a low level ultrasonic signal for a short period of time, in order to release any tissue stuck to the ultrasonic blade. This short, sub-therapeutic signal may reduce the level of sticking experienced by the user. This feature may be useful if a ultrasonic shear device were designed for multiple uses and the ultrasonic blade coating began to wear off. In this way, the techniques and features described herein may be used to reduce the amount of tissue sticking to the ultrasonic blade.

A method for calibrating an end effector and Hall-effect sensor may include calibrating the end effector and Hall-effect sensor during manufacturing of thereafter. As discussed above, process 3300 shown in FIG. 32, may be used to calibrate a controller for the end effector. For example, a clamp arm position of a ultrasonic device may be calibrated during assembly. As discussed herein, sensing the position of the clamp arm relative to the ultrasonic blade may provide relevant surgical device information that may enable new capabilities, including but not limited to the ability to sense a quantity or type of tissues which may be clamped inside the jaws. Further, determinations about various algorithms to execute (e.g., such sealing a vessel without transection) may be made based on sensing the position of the clamp arm. However, in various aspects, in order for this information to be useful and reliable, the surgical device must be calibrated in relation to a baseline such as when the clamp arm is fully open or when the clamp arm fully closed with zero material in the end effector.

As described above, determining a Travel Ratio (TR) may help in various processes to control an end effector. In determining TR, X1 is the clamp arm position when the device is fully closed with no tissue. Determining the value (e.g., Hall effect signal) corresponding to X1 may be done during manufacturing and may be part of the calibration process.

Figure 24:
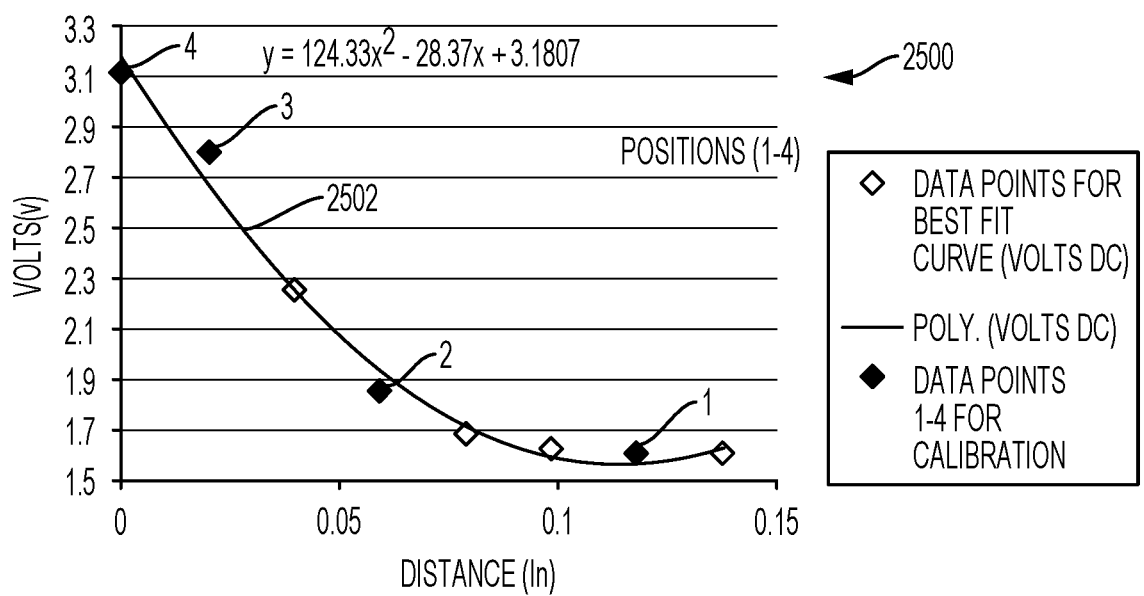
FIG. 24 illustrates a graph of a best fit curve of Hall-effect sensor output voltage as a function of distance for various positions of the clamp arm as the clamp arm moves between fully closed to a fully open positions in accordance with one aspect of the present disclosure.

Turning now to FIG. 24, there is shown a graph 2500 of a best fit curve 2502 of Hall-effect sensor output voltage along the y-axis as a function of absolute distance (in) along the x-axis for various positions of the clamp arm. The best fit curve 2502 is plotted based on the absolute distance (in) of the clamp arm from the ultrasonic blade as listed in the third column 1406 of the table 1400 shown in FIG. 14A and the corresponding Hall-effect sensor output voltage listed in the fourth column 1408 of the table 1400 shown in FIG. 14A as the clamp arm moves from a fully open position to a fully closed position in accordance with the present disclosure.

Still with reference to FIG. 24, there is shown an example electrical output of a Hall-effect sensor configured to sense clamp arm position is shown. The Hall-effect sensor signal strength plotted against displacement of the sensor (e.g., a magnet) may follow a parabolic shape as shown by the best fit curve 2502. To calibrate the Hall-effect sensor, several readings of the sensor are taken at known baseline locations. During calibration, the best fit curve 2502 as shown in FIG. 24 may be analyzed to confirm that the Hall-effect sensor is reading effectively based on readings made in a production setting. In this way, a Hall-effect sensor response corresponding to various positions of the clamp arm (e.g., fully open, fully closed, and discrete positions therebetween) may be recorded to create a best fit curve during production. Various data points may be recorded (e.g., four data points 1-4 as shown in FIG. 24 or more as may be necessary) to create the best fit curve 2502. For example, in a first position, a Hall-effect sensor response may be measured when the clamp arm is fully opened. In this way, turning briefly to FIG. 32, the process 3300 shown in FIG. 32 may detect 3302 a first measurement signal (e.g., a Hall-effect sensor response) corresponding to a fully open position of a clamp arm and a ultrasonic blade of the end effector.

Figure 25:
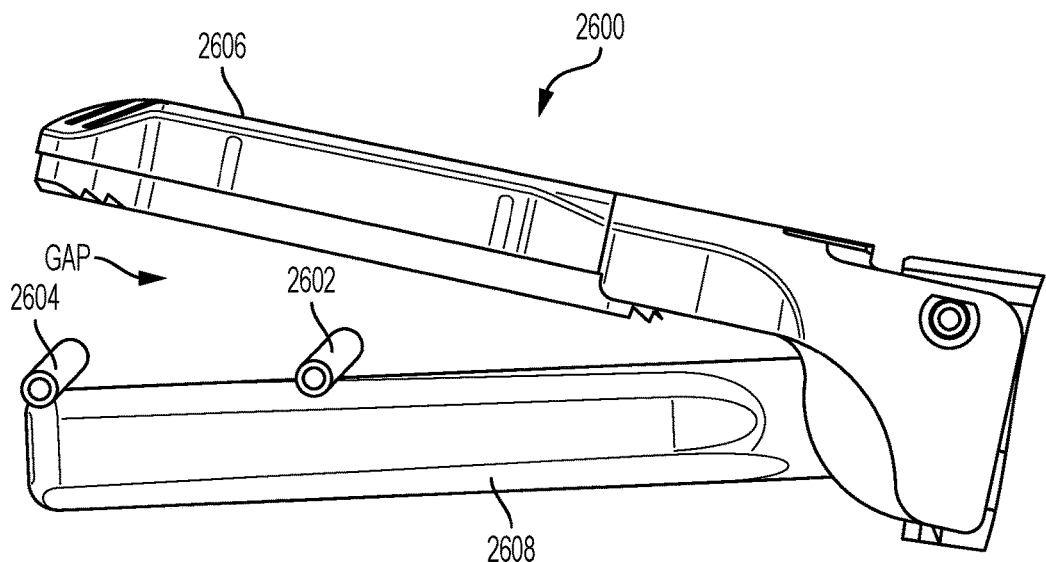
FIGS. 25-28 illustrate an end effector being calibrated in four different configurations in accordance with various aspects of the present disclosure using gage pins for two of the configurations for recording a Hall-effect sensor response corresponding to various positions of the clamp arm to record four data points (1-4) to create a best fit curve during production, where.

Turning back now to FIG. 24 in conjunction with FIG. 25, the four data points 1-4 represent voltage measured with a Hall-effect sensor as a function of the gap between the clamp arm 2606 and the ultrasonic blade 2608, as shown in FIG. 24. These data points 1-4 may be recorded as described in connection with FIGS. 25-28. The first data point (1) is recorded when the end effector 2600 is in the configuration shown in FIG. 25. The first data point (1) corresponds to the Hall-effect sensor output voltage recorded when the clamp arm 2606 is in the fully opened positon relative to the ultrasonic blade 2608.

Figure 26:
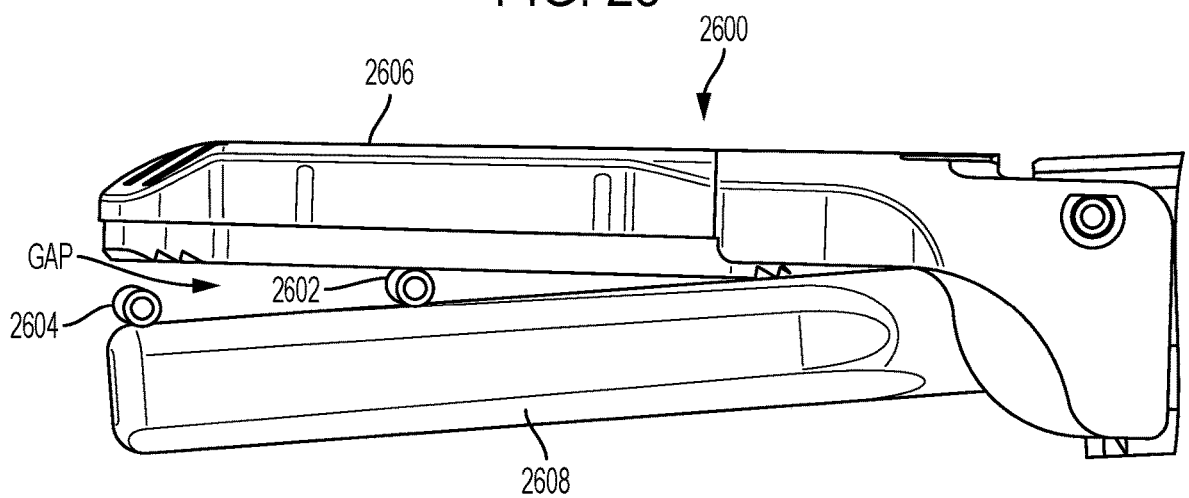

The second data point (2) is recorded when the end effector 2600 is in the configuration shown in FIG. 26. To obtain an accurate gap between the clamp arm 2606 and the ultrasonic blade 2808, a first gage pin 2602 of known diameter is placed at a predetermined location within the jaws of the end effector 2600, e.g., between the clamp arm 2606 and the ultrasonic blade 2608. As shown in FIG. 26, the first gage pin 2602 is positioned between the distal end and the proximal end of the ultrasonic blade 2608 and is grasped between the clamp arm 2606 and the ultrasonic blade 2608 to set an accurate gap between the clamp arm 2606 and the ultrasonic blade 2808. Once the clamp arm 2606 is closed to grasp the first gage pin 2602, the output voltage of the Hall-effect sensor is measured and recorded. The second data point (2) is correlated to the gap set between the clamp arm 2606 and the ultrasonic blade 2608 by the first gage pin 2602. In this way, the output voltage of the Hall-effect sensor is equated to the gap distance between the clamp arm 2606 and the ultrasonic blade 2608. The second data point (2) is one of several data points to develop the polynomial to generate the best fit curve 2502 shown in FIG. 24. The process 3300 described in FIG. 32 detects 3304 an actual Hall-effect sensor voltage and determines the gap between the clamp arm 2606 and the ultrasonic blade 2608 based on the best first curve 2502 (e.g., computing the polynomial).

Figure 27:
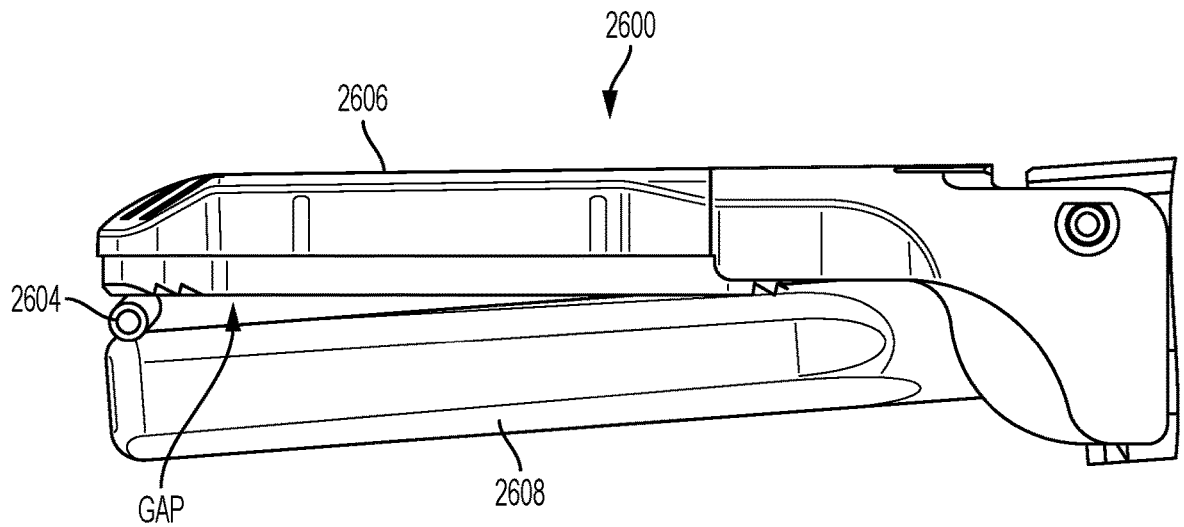

The third data point (3) is recorded when the end effector 2600 is in the configuration shown in FIG. 27. To obtain another accurate gap between the clamp arm 2606 and the ultrasonic blade 2808, the first gage pin 2602 is removed and a second gage pin 2604 of known diameter is placed at a predetermined location within the jaws of the end effector 2600, e.g., between the clamp arm 2606 and the ultrasonic blade 2608, that is different form the location of the first gage pin 2602. As shown in FIG. 27, the second gage pin 2604 is positioned between the distal end and the proximal end of the ultrasonic blade 2608 and is grasped between the clamp arm 2606 and the ultrasonic blade 2608 to set an accurate gap between the clamp arm 2606 and the ultrasonic blade 2808. Once the clamp arm 2606 is closed to grasp the second gage pin 2602, the output voltage of the Hall-effect sensor is measured and recorded. The third data point (3) is correlated to the gap set between the clamp arm 2606 and the ultrasonic blade 2608 by the second gage pin 2604. In this way, the output voltage of the Hall-effect sensor is equated to the gap distance between the clamp arm 2606 and the ultrasonic blade 2608. The third data point (3) is one of several data points to develop the polynomial to generate the best fit curve 2502 shown in FIG. 24. The process 3300 described in FIG. 32 detects 3304 an actual Hall-effect sensor voltage and determines the gap between the clamp arm 2606 and the ultrasonic blade 2608 based on the best first curve 2502 (e.g., computing the polynomial).

Figure 28:
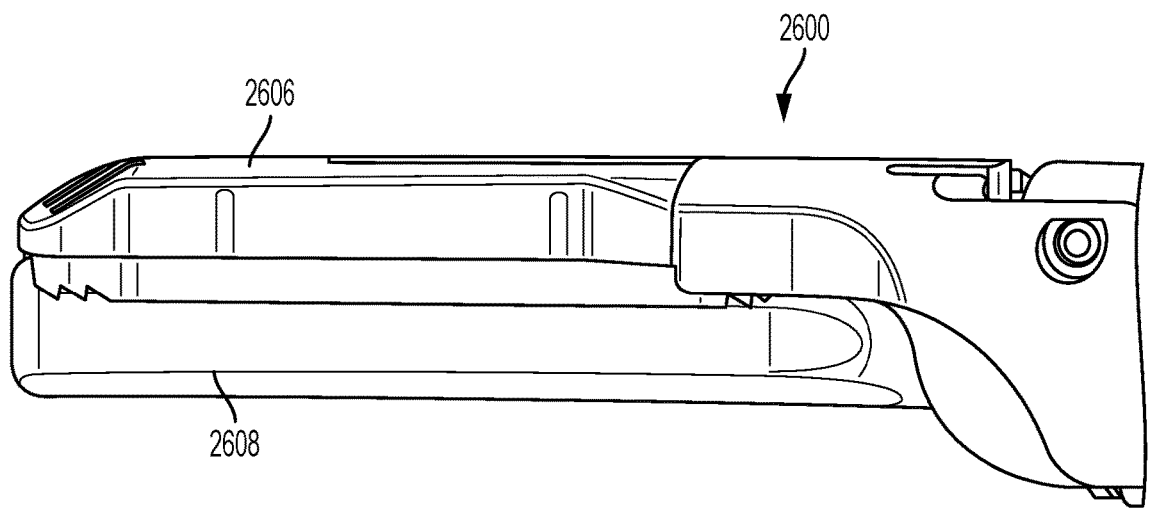

The fourth data point (4) is recorded when the end effector 2600 is in the configuration shown in FIG. 28. To obtain the fourth data point (4), there are no gage pins 2602, 2604 placed between the clamp arm 2606 and the ultrasonic blade 2608, but rather, the clamp arm 2606 is place in the fully closed position relative to the ultrasonic blade 2608. Once the clamp arm 2606 is placed in the fully closed position, the output voltage of the Hall-effect sensor is measured and recorded. The fourth data point (4) is correlated to the fully closed clamp arm 2606 position. In this way, the output voltage of the Hall-effect sensor is equated to the fully closed clamp arm 2606 position relative to the ultrasonic blade 2608. The fourth data point (4) is one of several data points to develop the polynomial to generate the best fit curve 2502 shown in FIG. 24. The process 3300 described in FIG. 32 detects 3304 an actual Hall-effect sensor voltage and determines the gap between the clamp arm 2606 and the ultrasonic blade 2608 based on the best first curve 2502 (e.g., computing the polynomial).

Various configurations of gage pins may create known displacements and/or angles between the clamp arm 2606 and the ultrasonic blade 2608 of the end effector 2600. Using kinematics of a given clamp arm/ultrasonic blade/shaft design and gage pins of known diameter, a theoretical displacement of the shaft assembly can be known at each of the, e.g., four or more positions. This information may be input, along with the voltage readings of the Hall-effect sensor, to fit a parabolic curve (e.g., best fit curve 2502 as shown in FIG. 24), which may become a characteristic of each individual surgical device. This information may be loaded onto the surgical device via an EEPROM or other programmable electronics configured to communicate with the generator (e.g., the generator 102 shown in FIG. 6) during use of the surgical device.

The Hall-effect sensor signal response at, for example, the four positions of the clamp arm described above may be graphed and the responses may be fit and entered into to a lookup table or developed into a polynomial which may be used to set/calibrate the Hall-effect sensor such that when used by a surgeon, the end effector delivers the tissue effect desired. In this way, process 3300 may determine 3308 a best fit curve to represent signal strength (e.g., from Hall-effect sensor) as a function of sensor displacement (e.g., magnet displacement) based on at least the first, second, and third signals, the fully open, intermediate, and fully closed positions, and a dimension of the rigid body. Process 3300 may also create 3310 a lookup table based on at least the first, second, and third signals, and the fully open, intermediate, and fully closed positions.

The positioning of the Hall-effect sensor/magnet arrangement in the configurations described above may be used to calibrate the surgical device such that the most sensitive movements of the clamp arm 2606 exist when the clamp arm 2606 is closest to the ultrasonic blade 2608. Four positions, corresponding to four data points (1-4), were chosen in the example described above, but any number of positions could be used at the discretion of design and development teams to ensure proper calibration.

In one aspect, the techniques and features described herein may be used to provide feedback to a surgeon to indicate when the surgeon should use hemostasis mode for the vessel sealing procedure prior to engaging the cutting procedure. For example, hemostasis mode algorithm may be dynamically changed based on the size of a vessel grasped by the end effector 2600 in order to save time. This may require feedback based on the position of the clamp arm 2606.

Figure 29A:
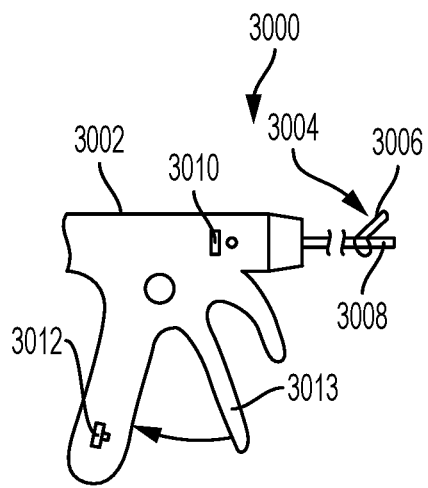
FIGS. 29A-D illustrate an example surgical instrument in accordance with one aspect of the present disclosure and charts showing example output power level in a hemostasis mode for small and large vessels, where.

FIG. 29A is a schematic diagram 3000 of surgical instrument 3002 configured to seal small and large vessels in accordance with one aspect of the present disclosure. The surgical instrument 3002 comprises an end effector 3004, where the end effector comprises a clamp arm 3006 and an ultrasonic blade 3008 for treating tissue including vessels of various sizes. The surgical instrument 3002 comprises a Hall-effect sensor 3010 to measure the position of the end effector 3004. A closure switch 3012 is provided to provide a feedback signal indicating whether the trigger handle 3013 of the surgical instrument is in a fully closed position.

Figure 29B:
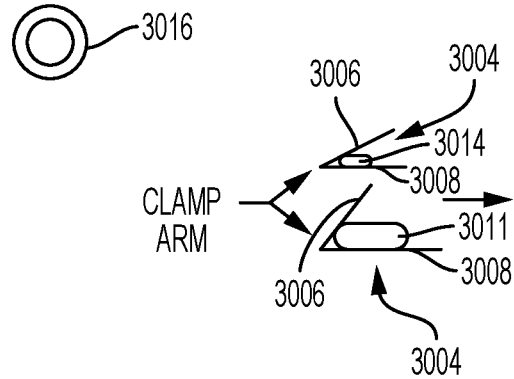

Turning now to FIG. 29B there is shown a diagram of an example range of a small vessel 3014 and a large vessel 3016 and the relative position of a clamp arm of the end effector in accordance with one aspect of the present disclosure. With reference to FIGS. 29A-B, The surgical instrument 3002 shown in FIG. 29A is configured to seal small vessels 3014 having a diameter <4 mm and large vessels 3016 having a diameter >4 mm and the relative position of the clamp arm 3006 when grasping small and large vessels 3014, 3016 and the different voltage readings provided by the end effector 3010 depending on the size of the vessel.

Figure 29C:
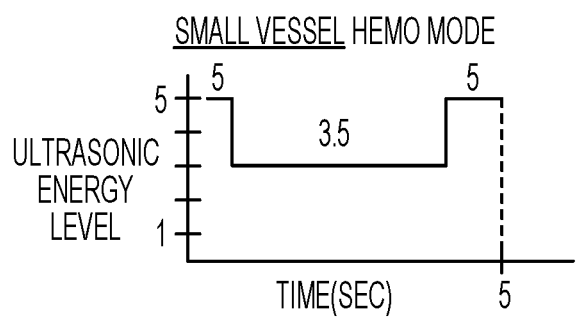
Figure 29D:
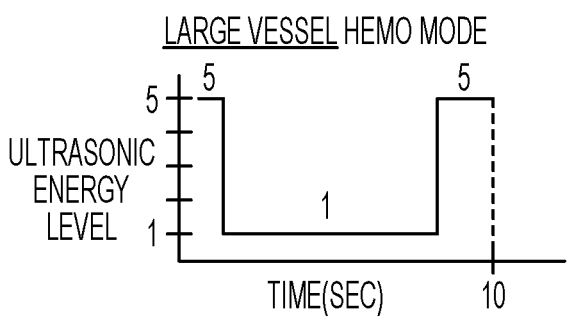

FIGS. 29C and 29D are two graphs 3020, 3030 that depicts two processes for sealing small and large vessels by applying various ultrasonic energy levels for a different periods of time in accordance with one aspect of the present disclosure. Ultrasonic energy level is shown along the y-axis and time (Sec) is shown along the x-axis. With reference now to FIGS. 29A-C, the first graph 3020 shown in FIG. 29C shows a process for adjusting the ultrasonic energy drive level of a ultrasonic blade to seal a small vessel 3014. In accordance with the process illustrated by the first graph 3020 for sealing and transecting a small vessel 3014, a high ultrasonic energy (5) is applied for a first period 3022. The energy level is then lowered to (3.5) for a second period 3024. Finally, the energy level is raised back to (5) for a third period 3026 to complete sealing the small vessel 3014 and achieve transection and then the energy level is turned off. The entire cycle lasting about 5 seconds.

With reference now to FIGS. 29A-D, the second graph 3030 shown in FIG. 29D shows a process for adjusting the ultrasonic energy drive level of a ultrasonic blade to seal a large vessel 3016. In accordance with the process illustrated by the second graph 3030 for sealing and transecting a large vessel 3016, a high ultrasonic energy (5) is applied for a first period 3032. The energy level is then lowered to (1) for a second period 3034. Finally, the energy level is raised back to (5) for a third period 3036 to complete sealing the large vessel 3016 and achieve transection and then the energy level is turned off. The entire cycle lasting about 10 seconds.

Smaller vessels 3014 may be easier to seal at high burst pressure levels. Thus, it may be desirable to sense and determine whether a smaller vessel 3014 (e.g., less than 4 mm) is clamped by the clamp arm 3006, and if so, the ultrasonic energy level may not need to be dropped to 1. Instead, the energy level could be dropped less, to about 3.5 for example, as shown by the first graph 3020 shown in FIG. 29C. This may allow the surgeon to get through the vessel, coagulate it, and cut the vessel more quickly with knowledge that the process can go faster because the vessel 3014 is slightly smaller. If the vessel 3016 is larger, (e.g., 4 mm or greater) a process that heats the vessel slower and over a longer period of time may be more desirable, as shown by the second graph 3030 in FIG. 29D.

Figure 30:
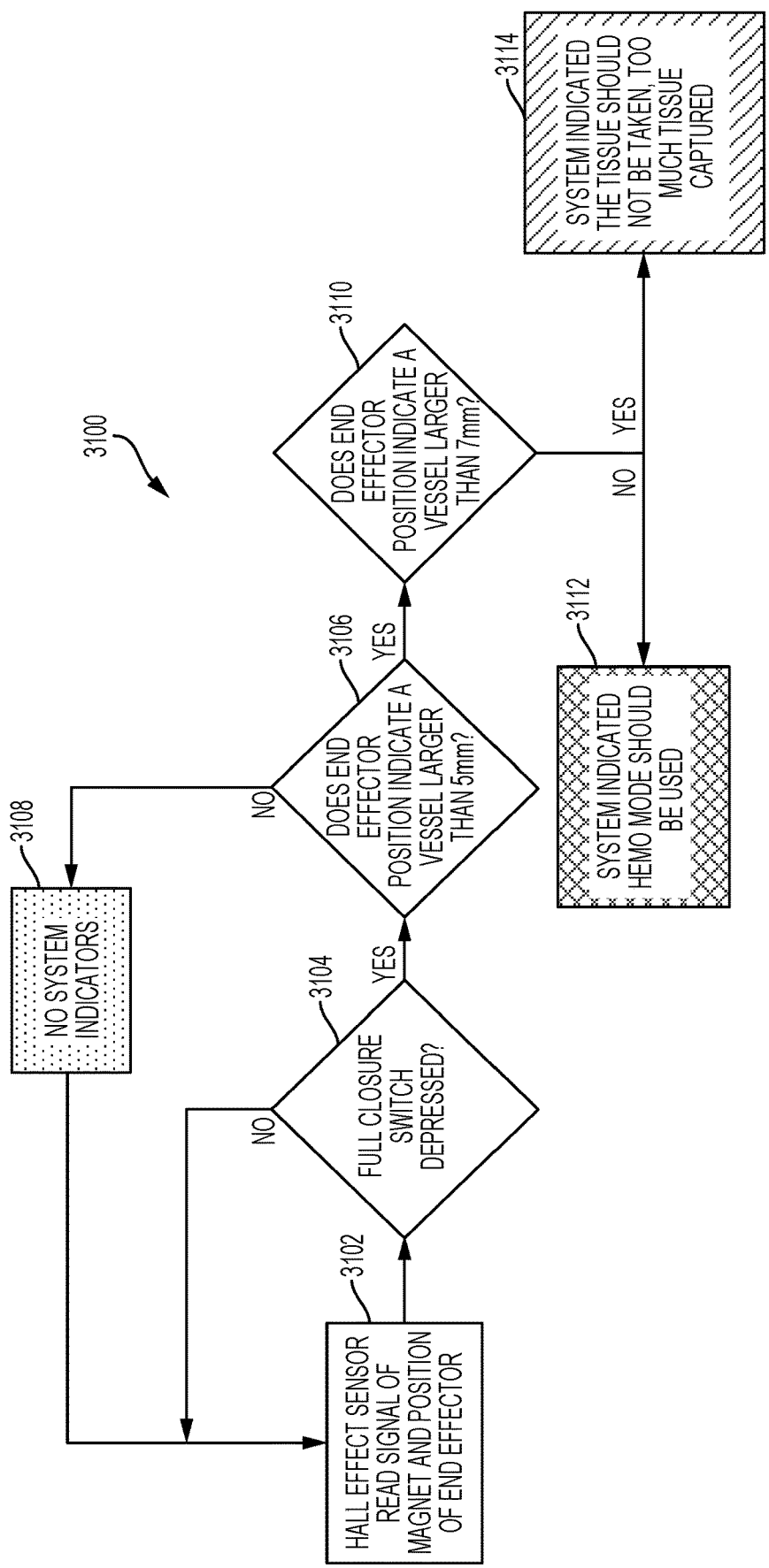
FIG. 30 is a logic diagram illustrating an example process for determining whether hemostasis mode should be used, in accordance with one aspect of the present disclosure.

FIG. 30 is a logic diagram illustrating an example process 3100 for determining whether hemostasis mode should be used, in accordance with one aspect of the present disclosure. At the outset, the process 3100 reads 3102 the signal from a Hall-effect sensor determine 3102 the position of an end effector. The process 3100 then determines 3104 if a full closure switch of the surgical device is depressed, or if the handle of the surgical device is fully closed. If the full closure switch of the surgical device is not depressed and/or if the handle of the surgical device is not fully closed, the process 3100 may continue to read 3102 the Hall-effect sensor to determine the position of the end effector. If the full closure switch of the surgical device is depressed, or if the handle of the surgical device is fully closed, the process 3100 determines 3106 if the end effector position indicates a vessel larger than 5 mm. If the end effector position does not indicate a vessel larger than 5 mm, and no system indicators are found 3108, the process 3100 may continue to read 3102 the Hall-effect sensor and determine the position of the end effector.

If the end effector position indicates a vessel larger than 5 mm, the process 3100 determines 3110 if the end effector position indicates a vessel larger than 7 mm. If the end effector position does not indicate a vessel larger than 7 mm, the process 3100 indicates 3112 that hemostasis mode should be used. This condition may be indicated using a variety of auditory, vibratory, or visual feedback techniques including, for example, a green LED located on the surgical device (e.g., on top of the handle) may be enabled. If the end effector position does indicate a vessel larger than 7 mm, the process 3100 indicates 3114 that the tissue should not be taken (i.e., hemostasis mode should not be used) because too much tissue has been captured by the end effector. This condition may be indicated using a variety of auditory, vibratory, or visual feedback techniques including, for example, a red LED on the surgical device (e.g., on top of the handle) may be enabled.

Figure 31:
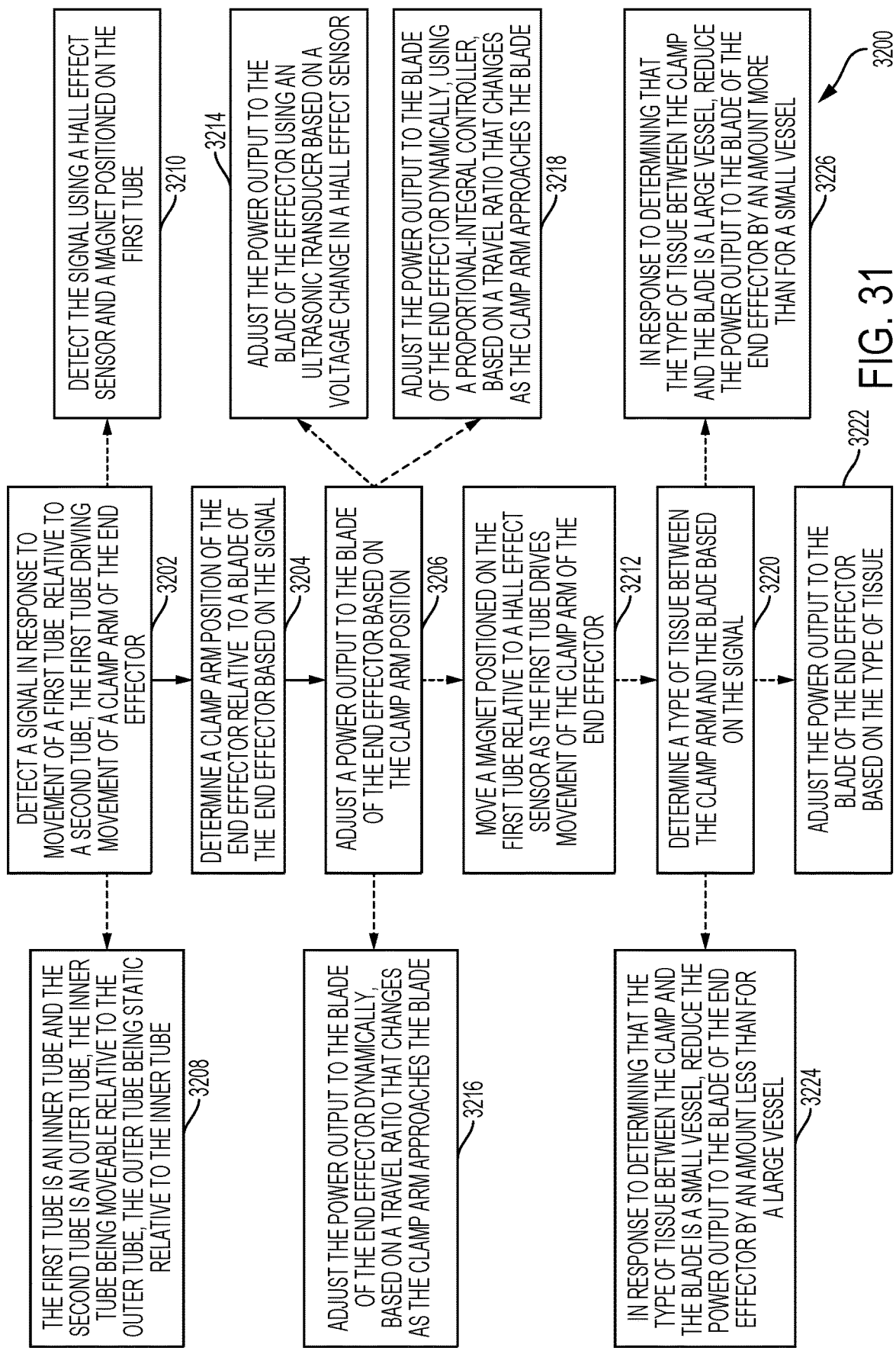
FIG. 31 is a logic diagram illustrating an example process for end effector control in accordance with one aspect of the present disclosure.

FIG. 31 is a logic diagram illustrating an example process 3200 for end effector control in accordance with one aspect of the present disclosure. In one aspect Referring to FIG. 31, process 3200 detects 3202 a signal (e.g., at a Hall-effect sensor) in response to movement of a first tube relative to a second tube, the first tube driving movement of a clamp arm of the end effector. The first tube may be, for example, similar to reciprocating tubular actuating member 58 (FIGS. 3 and 4) and the second tube may be, for example, similar to outer tubular sheath 56 (FIGS. 3 and 4). In other words, as described in FIG. 31, the first tube may be an inner tube and the second tube is an outer tube. The inner tube may be moveable 3208 relative to the outer tube. The outer tube may be static relative to the inner tube. The process 3200 detects 3210 the signal using a Hall-effect sensor and a magnet positioned on the first tube.

The process 3200 continues and determines 3204 a clamp arm position of the end effector relative to a ultrasonic blade of the end effector based on the signal (from, e.g., Hall-effect sensor voltage output). Once clamp arm position relative to ultrasonic blade is known, the vibrational mode of the ultrasonic blade can be adjusted to obtain different tissue effects. In this way, the process 3200 adjusts 3206 a power output to the ultrasonic blade of the end effector based on the clamp arm position. For example, the process 3200 may adjust 3214 the power output to the ultrasonic blade of the end effector using an ultrasonic transducer based on a voltage change in a Hall-effect sensor. Alternatively, the process can effectively seal vessels without transection. In this way, the process 3200 may adjust 3218 the power output to the ultrasonic blade of the end effector dynamically, using a proportional-integral controller, based on a travel ratio that changes as the clamp arm approaches the ultrasonic blade.

In another aspect, the process 3200 may adjust 3216 the power output to the ultrasonic blade of the end effector dynamically, based on the travel ratio that changes as the clamp arm approaches the ultrasonic blade. For example, as the clamp arm moves towards the ultrasonic blade and a Desired Value (FIGS. 21 and 22) is approached, the amount of power output to the ultrasonic blade and into the tissue may be reduced. This is because the ultrasonic blade will cut the tissue with enough power. However, if the power being output is reduced over time as the Desired Value is approached (where a full transection may be represented by a Travel Ratio of 1), the chance that the tissue is transected may be drastically reduced. In this way, effective sealing may be achieved without cutting the tissue as may be desired by the surgeon.

In one aspect, the process 3200 of FIG. 31 moves 3212 a magnet positioned on the first tube relative to a Hall-effect sensor as the first tube drives movement of the clamp arm of the end effector. The process 3200 then determines 3220 a type of tissue between the clamp arm and the ultrasonic blade based on a signal (from, e.g., a Hall-effect sensor). Further, using a processor and/or memory, one or more algorithms (e.g., for sealing a vessel without transection) may be chosen based on the thickness, quantity, or type of tissue determined to be clamped inside the jaws. In response to determining that the type of tissue between the clamp and the ultrasonic blade is a large vessel, the process 3200 may reduce 3226 the power output to the ultrasonic blade of the end effector by an amount more than for a small vessel. Further, in response to determining that the type of tissue between the clamp and the ultrasonic blade is a small vessel, the process 3200 may reduce 3224 the power output to the ultrasonic blade of the end effector by an amount less than for a large vessel. In one aspect, instead of changing algorithms for small vessels as described above, an indicator may be provided to the surgeon to indicate the thickness of the tissue captured in the end effector. In one aspect, the process 3200 adjusts 3222 the power output to the ultrasonic blade of the end effector based on the type of tissue.

FIG. 32 is a logic diagram illustrating an example process 3300 for calibrating an apparatus for controlling for an end effector in accordance with one aspect of the present disclosure. In one aspect, the process 3300 detects 3302 a first signal corresponding to a fully open position of a clamp arm and a blade of the end effector. The process 3300 then detects 3304 a second signal corresponding to an intermediate position of the clamp arm and the blade of the end effector, the intermediate position resulting from clamping a rigid body between the clamp arm and the blade. The process detects 3306 a third signal corresponding to a fully closed position of the clamp arm and the blade of the end effector. Once the three signals are detected, the process 3300 determines 3308 a best fit curve to represent signal strength as a function of sensor displacement based on at least the first, second, and third signals corresponding to the fully open, intermediate, and fully closed positions, respectively, and a dimension of the rigid body. An example of a best fit curve in this context is shown in FIGS. 14B and 24. Finally, the process 3300 creates 3310 a lookup table based on at least the first, second, and third signals corresponding to the fully open, intermediate, and fully closed positions, respectively.

As described hereinabove, the position of the clamp arm portion of the end effector can be measured with a Hall-effect sensor/magnet arrangement. A tissue pad, usually made of TEFLON, may be positioned on the clamp arm to prevent tissue from sticking to the clamp arm. As the end effector is used and the tissue pad is worn, it will be necessary to track the drift of the Hall-effect sensor output signal and establish changing thresholds to maintain the integrity of the tissue treatment algorithm selection and the end of cut trigger points feedback to the tissue treatment algorithms.

Accordingly, a control system is provided. The output of the Hall-effect sensor in the form of counts can be used to track the aperture of the end effector clamp arm. The reader may refer to FIGS. 34 and 35 for ADC systems 3500, 3600 that can employ the counter output of an ADC. The clamp arm position, with or without a tissue pad, can be calibrated using the techniques described herein. Once the clamp arm position is calibrated, the position of the clamp arm and wear of the tissue pad can be monitored. In one aspect, the control system determines that the clamp arm is in a closed position by monitoring for a rise in acoustic impedance that occurs when the ultrasonic blade contacts either tissue or the tissue pad. Thus, a specific number of ADC counter will accumulate a specific number of counts from the time the clamp arm goes from a fully open position to a fully closed position. In one implementation, based on the configuration of the Hall-effect sensor, the Hall-effect sensor ADC counts increase as the clamp arm closes towards the ultrasonic blade. As the tissue pad wears, the counter will accumulate an incremental additional number of counts due to the additional rotational travel experienced by the clamp arm due to tissue pad wear. By tracking the new count value for a closed clamp arm position, the control system can adjust the trigger threshold for an end of cut and better predict the total range of aperture of the clamp arm that has occurred.

Furthermore, the Hall-effect sensor ADC counts may be employed to determine the tissue coefficient of friction ($\mu$) of the tissue under treatment based on the aperture of the clamp arm by employing predetermined $\mu$ values stored in a look-up table. For example, the specific tissue treatment algorithm can be dynamically adjusted or changed during an ultrasonic treatment cycle (e.g., firing sequence or activation of ultrasonic energy) to optimize the tissue cut based on the tissue type (e.g., fatty tissue, mesentery, vessel) or the tissue quantity or thickness.

Figure 33:
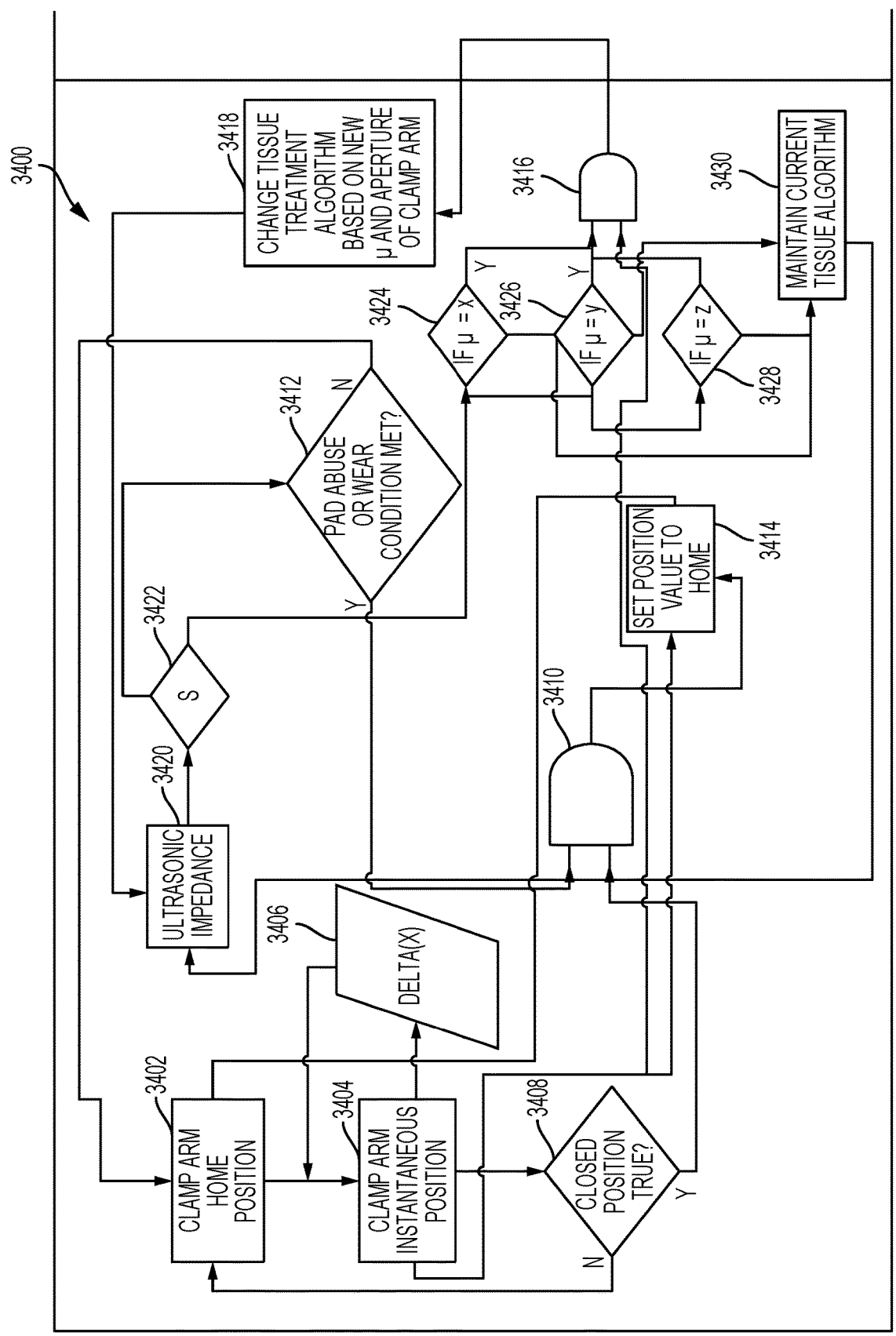
FIG. 33 is a logic diagram of a process for tracking wear of the tissue pad portion of the clamp arm and compensating for resulting drift of the Hall-effect sensor and determining tissue coefficient of friction in accordance with one aspect of the present disclosure.

FIG. 33 is a logic diagram of a process 3400 for tracking wear of the tissue pad portion of the clamp arm and compensating for resulting drift of the Hall-effect sensor and determining tissue coefficient of friction, according to one aspect of the present disclosure. The process 3400 may be implemented in software, hardware, firmware, or a combination thereof, employing the generator circuit environment illustrated in connection with FIGS. 6-10.

In one aspect, the process 3400 may be implemented by a circuit may comprising a controller comprising one or more processors (e.g., microprocessor, microcontroller) coupled to at least one memory circuit. The at least one memory circuit stores machine executable instructions that when executed by the processor, cause the processor to execute the process 3400.

The processor may be any one of a number of single or multi-core processors known in the art. The memory circuit may comprise volatile and non-volatile storage media. In one aspect, the processor may include an instruction processing unit and an arithmetic unit. The instruction processing unit may be configured to receive instructions from the one memory circuit.

In one aspect, a circuit may comprise a finite state machine comprising a combinational logic circuit configured to implement the process 3400 described herein. In one aspect, a circuit may comprise a finite state machine comprising a sequential logic circuit comprising a combinational logic circuit and at least one memory circuit, for example. The at least one memory circuit can store a current state of the finite state machine. The sequential logic circuit or the combinational logic circuit can be configured to implement the process 3400 described herein. In certain instances, the sequential logic circuit may be synchronous or asynchronous.

In other aspects, the circuit may comprise a combination of the processor and the finite state machine to implement the compression and decompression techniques described herein. In other embodiments, the finite state machine may comprise a combination of the combinational logic circuit and the sequential logic circuit.

As described herein, the position of the clamp arm is sensed by a Hall-effect sensor relative to a magnet located in a closure tube of a surgical instrument. Turning now to the process 3400, the initial home position of the clamp arm, e.g., the position of the Hall-effect sensor located on the closure tube, is stored 3402 in memory. As the closure tube is displaced in a distal direction, the clamp arm is closed towards the ultrasonic blade and the instantaneous position of the clamp arm is stored 3404 in memory. The difference, delta (x), between the instantaneous position and the home position of the clamp arm is calculated 3406. The difference, delta (x), may be used to determine a change in displacement of the tube, which can be used to calculate the angle and the force applied by the clamp arm to the tissue located between the clamp arm and the ultrasonic blade. The instantaneous position of the clamp arm is compared 3408 to the closed position of the clamp arm determine whether the clamp arm is in a closed position. While the clamp arm is not yet in a closed position, the process 3400 proceeds along the no path (N) and compares the instantaneous position of the clamp arm with the home position of the clamp arm until the clamp reaches a closed position.

When the clamp arm reaches a closed position, the process 3400 continues along the yes path (Y) and the closed position of the clamp arm is applied to one input of a logic AND function 3410. The logic AND function 3410 is a high level representation of a logic operation, which may comprise boolean AND, OR, XOR, and NAND operations implemented either in software, hardware, or a combination thereof. When a tissue pad abuse or wear condition is determined based on acoustic impedance measurements, the current clamp arm closed position is set 3414 as the new home position of the clamp arm to compensate for the abuse or wear condition. If no tissue pad abuse or wear is determined, the home position of the clamp arm remains the same. Abuse or wear of the clamp arm tissue pad is determined by monitoring 3420 the impedance 3422 of the ultrasonic blade. The tissue pad/ultrasonic blade interface impedance id s determined 3422 and compared 3412 to a tissue pad abuse or wear condition. When the impedance corresponds to a tissue pad abuse or wear condition, the process 3400 proceeds along the yes path (Y) and the current closed position of the clamp arm is set 3414 as the new home position of the clamp arm to compensate for the abuse or wear condition of the tissue pad. When the impedance does not correspond to a tissue pad abuse or wear condition, the process 3400 proceeds along the no path (N) and the home position of the clamp arm remains the same.

The stored 3404 instantaneous position of the clamp arm is also provided to the input of another logic AND function 3416 to determine the quantity and thickness of the tissue clamped between the clamp arm and the ultrasonic blade. The tissue/ultrasonic blade interface impedance is determined 3422 and is compared 3424, 34267, 3428 to multiple tissue coefficients of friction $\mu=x$, $\mu=y$, or $\mu=z$. Thus, when the tissue/ultrasonic blade interface impedance corresponds to one of the tissue coefficients of friction $\mu=x$, $\mu=y$, or $\mu=z$ based on the tissue quantity or thickness, e.g., the aperture of the clamp arm, the current tissue algorithm is maintained 3430 and the current algorithm is used for monitoring 3420 the impedance 3422 of the ultrasonic blade. If the tissue coefficient of friction $\mu=x$, $\mu=y$, or $\mu=z$ based on the tissue quantity or thickness, e.g., the aperture of the clamp arm, changes, the current tissue algorithm is changed 3418 based on the new tissue coefficient of friction $\mu$ and the tissue quantity or thickness, e.g., the aperture of the clamp arm and the new algorithm is used for monitoring 3420 the impedance 3422 of the ultrasonic blade.

Accordingly, the current clamp arm aperture is used to determine the current tissue coefficient of friction $\mu$ based on the quantity and thickness of tissue as measured by the aperture of the clamp arm. Thus, an initial algorithm may be based on an initial aperture of the clamp arm. The impedance of the ultrasonic blade is compared 3424, 3426, 3428 to several tissue coefficients of friction $\mu=x$, $\mu=y$, or $\mu=z$, which are stored in a look-up table, and correspond to fatty tissue, mesentery tissue, or vessel tissue, for example. If no match occurs between the impedance of the ultrasonic blade and the tissue coefficient of friction, the process 3400 proceeds along the no paths (N) of any of the tissue impedance comparisons 3424, 3426, 3428 and the current tissue algorithm is maintained. If any one of the outputs of the comparison 3424, 3426, 3428 functions is true, the processor switches to a different tissue treatment algorithm based on the new tissue impedance and clamp arm aperture. Accordingly, a new tissue treatment algorithm is loaded in the ultrasonic instrument. The process 3400 continues by monitoring 3420 the impedance of the ultrasonic blade, clamp arm aperture, and tissue pad abuse or wear.

Figure 34:
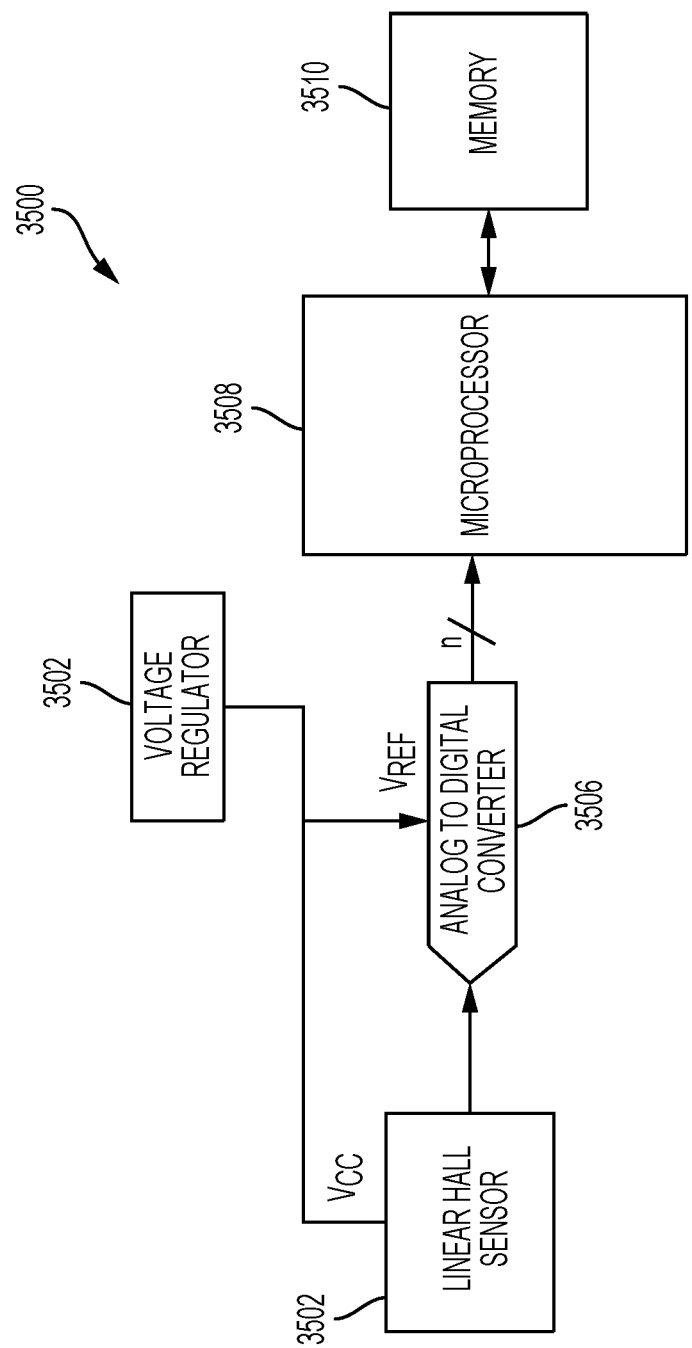
FIG. 34 illustrates a Hall-effect sensor system that can be employed with the process of FIG. 33 in accordance with one aspect of the present disclosure.

FIG. 34 illustrates a Hall-effect sensor system 3500 that can be employed with the process 3400 of FIG. 33, according to one aspect of the present disclosure. In connection with the process 3400 described in FIG. 33, the Hall-effect sensor system 3500 of FIG. 34 includes a Hall-effect sensor 3502 powered by a voltage regulator 3504. The output of the Hall-effect sensor 3502 is an analog voltage proportional to the position of the clamp arm, which is applied to an analog-to-digital converter 3506 (ADC). The n-bit digital output of the ADC 3506 is applied to a microprocessor 3508 coupled to a memory 3510. The microprocessor 3508 is configured to process and determine the position of the clamp arm based on the n-bit digital input from the ADC 3505. It will be appreciated that the digital output of the ADC 3506 may be referred to as a count.

As described herein, the analog output of the Hall-effect sensor is provided to an internal or an external analog-to-digital converter such as the ADC 3506 shown in FIG. 34 or any of the analog-to-digital converter circuits located in the generator. The transducer 104 shown in FIG. 6 may comprise an Hall-effect sensor comprising and analog-to-digital converter circuit whose output is applied to the control circuit 108. In one aspect, the generator 102 shown in FIG. 7 comprises several analog-to-digital converter circuits such as ADCs 176, 178, 180, which can be adapted and configured to receive the analog voltage output of the Hall-effect sensor and convert it into digital forms to obtain counts and to interface the Hall-effect sensor with a DSP processor 174, microprocessor 190, a logic device 166, and/or a controller 196.

Figure 35:
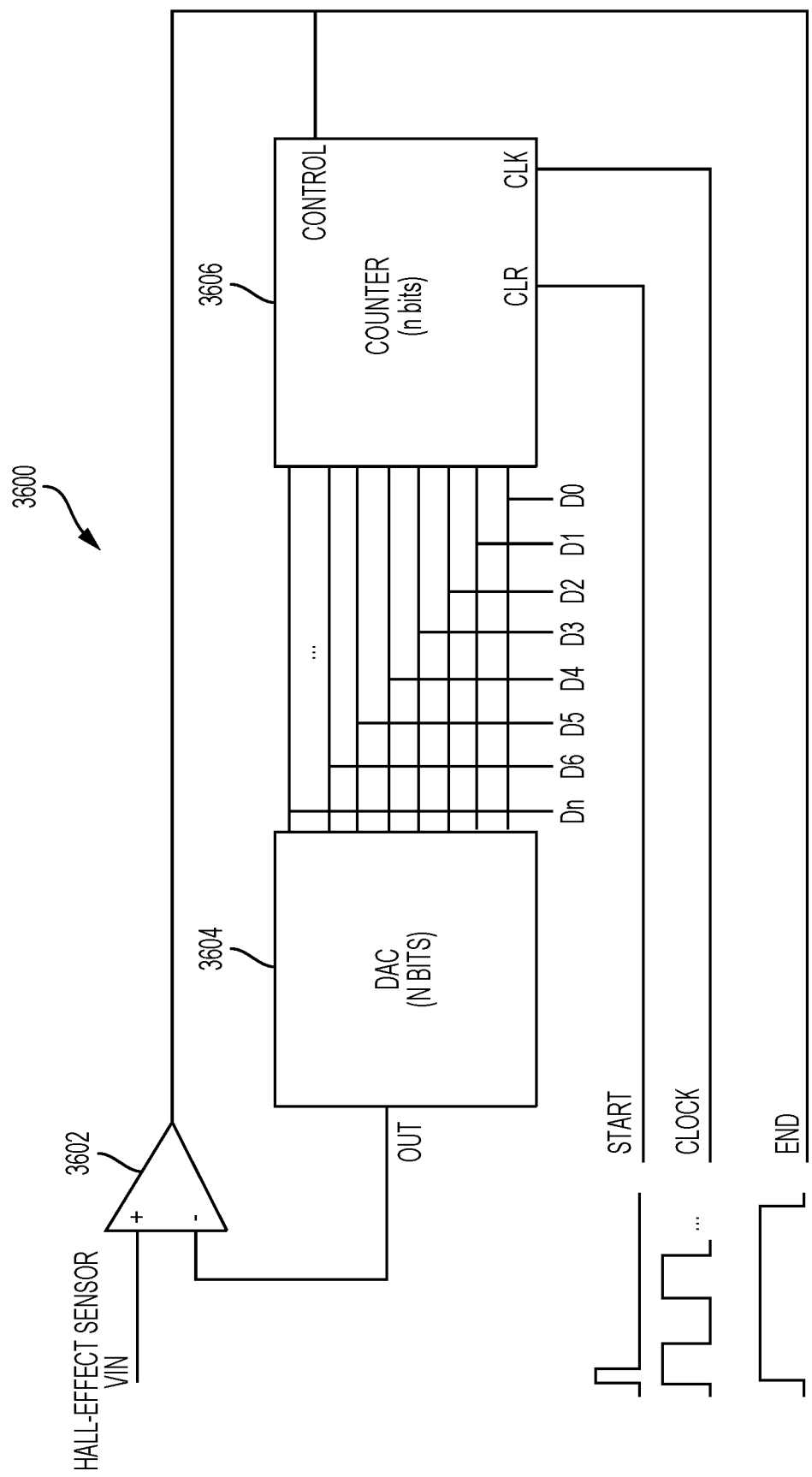
FIG. 35 illustrates one aspect of a ramp type counter analog-to-digital converter (ADC) that may be employed with the Hall-effect sensor system of FIG. 34 in accordance with one aspect of the present disclosure.

FIG. 35 illustrates one aspect of a ramp type counter analog-to-digital converter 3600 (ADC) that may be employed with the Hall-effect sensor system 3500 of FIG. 34, according to one aspect of the present disclosure. The digital ramp ADC 3600 receives an analog input voltage from a Hall-effect sensor at the Vin positive input terminal of a comparator 3602 and Dn through D0 (Dn-D0) are the digital outputs (n-bits). The control line found on a counter 3606 turns on the counter 3606 when it is low and stops the counter 3606 when it is high. In operation, the counter 3606 is increased until the value found on the counter 3606 matches the value of the analog input signal at Vin. The digital output Dn-D0 is applied to a digital-to-analog converter 3604 (DAC) and the analog output is applied to the negative terminal of the comparator 3602 and it is compared to the analog input voltage at Vin. When this condition is met, the value on the counter 3606 is the digital equivalent of the analog input signal at Vin.

A START pulse is provided for each analog input voltage Vin to be converted into a digital signal. The END signal represents the end of the conversion for each individual analog input voltage found at Vin (each sample), and not for the entire analog input signal. Each clock pulse increments the counter 3606. Supposing an 8-bit ADC, for converting the analog value for "128" into digital, for example, it would take 128 clock cycles. The ADC 3600 counts from 0 to the maximum possible value (2n−1) until the correct digital output Dn-D0 value is identified for the analog input voltage present at Vin. When this is true, the END signal is given and the digital value for Vin is for at Dn-D0.

While various aspects have been described herein, it should be apparent, however, that various modifications, alterations and adaptations to those aspects may occur to persons skilled in the art with the attainment of some or all of the advantages of the invention. The disclosed aspects are therefore intended to include all such modifications, alterations and adaptations without departing from the scope and spirit of the invention. Accordingly, other aspects and implementations are within the scope of the following claims. For example, the actions recited in the claims can be performed in a different order and still achieve desirable results.

While various details have been set forth in the foregoing description, it will be appreciated that the various aspects of the techniques for operating a generator for digitally generating electrical signal waveforms and surgical instruments may be practiced without these specific details. One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

For conciseness and clarity of disclosure, selected aspects of the foregoing disclosure have been shown in block diagram form rather than in detail. Some portions of the detailed descriptions provided herein may be presented in terms of instructions that operate on data that is stored in one or more computer memories or one or more data storage devices (e.g. floppy disk, hard disk drive, Compact Disc (CD), Digital Video Disk (DVD), or digital tape). Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. In one form, several portions of the subject matter described herein may be implemented via an application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In some instances, one or more elements may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other. It is to be understood that depicted architectures of different components contained within, or connected with, different other components are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components, and/or electrically interacting components, and/or electrically interactable components, and/or optically interacting components, and/or optically interactable components.

In other instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present disclosure have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "one form," or "a form" means that a particular feature, structure, or characteristic described in connection with the aspect is included in at least one aspect. Thus, appearances of the phrases "in one aspect," "in an aspect," "in one form," or "in an form" in various places throughout the specification are not necessarily all referring to the same aspect. Furthermore, the particular features, structures or characteristics may be combined in any suitable manner in one or more aspects.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

Various aspects of the subject matter described herein are set out in the following numbered clauses:

1. A method for controlling an end effector, the method comprising: detecting a signal in response to movement of a first tube relative to a second tube, the first tube driving movement of a clamp arm of the end effector; determining a clamp arm position of the end effector relative to a ultrasonic blade of the end effector based on the signal; and adjusting a power output to the ultrasonic blade of the end effector based on the clamp arm position.

2. The method of clause 1, wherein adjusting the power output to the ultrasonic blade is achieved by manipulating the electrical current sent to the handpiece.

3. The method of clause 1 or 2, wherein the first tube is an inner tube and the second tube is an outer tube, the inner tube being moveable relative to the outer tube, the outer tube being static relative to the inner tube.

4. The method of any one of clause 1 or 2, wherein the first tube is an inner tube and the second tube is an outer tube, the outer tube being moveable relative to the inner tube, the inner tube being static relative to the inner tube.

5. The method of any one of clauses 1-4 further comprising detecting the signal using a Hall-effect sensor and a magnet positioned on the first tube.

6. The method of any one of clauses 1-5, further comprising moving a magnet positioned on the first tube relative to a Hall-effect sensor as the first tube drives movement of the clamp arm of the end effector.

7. The method of any one of clauses 1-6, further comprising adjusting the power output to the ultrasonic blade of the end effector using an ultrasonic transducer based on a voltage change in a Hall-effect sensor.

8. The method of any one of clauses 1-7, further comprising adjusting the power output to the ultrasonic blade of the end effector dynamically, based on a travel ratio that changes as the clamp arm approaches the ultrasonic blade.

9. The method of any one of clauses 1-8, further comprising adjusting the power output to the ultrasonic blade of the end effector dynamically, using a proportional-integral controller, based on a travel ratio that changes as the clamp arm approaches the ultrasonic blade.

10. The method of any one of clauses 1-9, further comprising switching off completely the power output to the ultrasonic blade of the end effector once a travel ratio threshold has been met.

11. The method of any one of clauses 1-10, further comprising: determining a quantity or thickness of tissue between the clamp arm and the ultrasonic blade based on the signal; and adjusting the power output to the ultrasonic blade of the end effector based on the quantity or thickness of tissue.

12. The method of clause 11, further comprising in response to determining that the quantity or thickness of tissue between the clamp arm and the ultrasonic blade is less than a predetermined threshold, reducing the power output to the ultrasonic blade of the end effector by an amount less than for a larger quantity or thickness of tissue.

13. The method of clause 11 or 12, further comprising in response to determining that the quantity or thickness of tissue between the clamp arm and the ultrasonic blade is above a predetermined threshold, reducing the power output to the ultrasonic blade of the end effector by an amount more than for a smaller quantity or thickness of tissue.

14. An apparatus for controlling an end effector, the apparatus comprising: a sensor configured to detect a signal in response to movement of a first tube relative to a second tube, the first tube driving movement of a clamp arm of the end effector; a processor configured to determine a clamp arm position of the end effector relative to a ultrasonic blade of the end effector based on the signal; and a transducer configured to adjust a power output to the ultrasonic blade of the end effector based on the clamp arm position.

15. The apparatus of clause 14, wherein the first tube is an inner tube and the second tube is an outer tube, the outer tube being moveable relative to the inner tube, the inner tube being static relative to the outer tube.

16. The apparatus of clause 14, wherein the first tube is an inner tube and the second tube is an outer tube, the inner tube being moveable relative to the outer tube, the outer tube being static relative to the inner tube.

17. The apparatus of any one of clauses 14-16, further comprising: a magnet positioned on the first tube; and wherein the sensor is a Hall-effect sensor used to detect the signal based on a position of the magnet.

18. The apparatus of any one of clauses 14-17, wherein the magnet positioned on the first tube moves relative to a Hall-effect sensor as the first tube drives movement of the clamp arm of the end effector.

19. The apparatus of any one of clauses 14-18, wherein the transducer is an ultrasonic transducer configured to adjust the power output to the ultrasonic blade of the end effector based on a voltage change in a Hall-effect sensor.

20. The apparatus of any one of clauses 14-19, wherein the transducer is configured to adjust the power output to the ultrasonic blade of the end effector dynamically, based on a travel ratio that changes as the clamp arm approaches the ultrasonic blade.

21. The apparatus of any one of clauses 14-20, further comprising: a proportional-integral controller configured to adjust the power output to the ultrasonic blade of the end effector dynamically, based on a travel ratio that changes as the clamp arm approaches the ultrasonic blade.

22. A method for calibrating an apparatus for controlling an end effector, the method comprising: detecting a first signal corresponding to a fully open position of a clamp arm and a ultrasonic blade of the end effector; detecting a second signal corresponding to an intermediate position of the clamp arm and the ultrasonic blade of the end effector, the intermediate position resulting from clamping a rigid body between the clamp arm and the ultrasonic blade; and detecting a third signal corresponding to a fully closed position of the clamp arm and the ultrasonic blade of the end effector.

23. The method of clause 22, further comprising: determining a best fit curve to represent signal strength as a function of sensor displacement based on at least the first, second, and third signals, the fully open, intermediate, and fully closed positions, and a dimension of the rigid body.

24. The method of clause 22 or 23, further comprising: creating a lookup table based on at least the first, second, and third signals, and the fully open, intermediate, and fully closed positions.

The invention claimed is:

1. An apparatus for controlling an end effector comprising a clamp arm, the apparatus comprising:
    a sensor configured to generate signals in response to movement of a first tube relative to a second tube, the first tube driving movement of the clamp arm of the end effector; and
    a control circuit configured to:
        receive a first signal, second signal, and a third signal from the sensor, wherein the first signal, the second signal, and the third signal are associated with positions of the clamp arm of the end effector as it moves;
        generate a fit curve based on the first signal, the second signal, and the third signal;
        receive a fourth signal from the sensor, wherein the fourth signal is associated with a current position of the clamp arm of the end effector as it moves; and
        generate a conclusion associated with a relative position of the clamp arm based on the fourth signal and the generated fit curve.

2. The apparatus of claim 1, wherein the end effector further comprises an ultrasonic blade, and wherein the control circuit is further configured to:
    determine an impedance of the ultrasonic blade in contact with tissue; and
    determine a type of the tissue based on the impedance.

3. The apparatus of claim 2, wherein the generated conclusion comprises an estimated gap between the clamp arm and the ultrasonic blade.

4. The apparatus of claim 3, further comprising a transducer configured to dynamically adjust a power output to the ultrasonic blade of the end effector during an ultrasonic treatment, to adjust a tissue cut based on the estimated gap and the type of the tissue.

5. The apparatus of claim 2, wherein the first signal is associated with an open position of the clamp arm relative to the ultrasonic blade, wherein the second signal is associated with an intermediate position of the clamp arm relative to the ultrasonic blade, and wherein the third signal is associated with a closed position of the clamp arm relative to the ultrasonic blade.

6. The apparatus of claim 1, wherein the control circuit is further configured to calibrate signals generated by the sensor during movement of the clamp arm of the end effector based on the generated fit curve to confirm that the sensor is generating accurate signals.

7. The apparatus of claim 6, wherein the calibration comprises a comparison of the fourth signal to the generated fit curve.

8. The apparatus of claim 1, wherein generation of the fit curve comprises computing a polynomial based on the first signal, the second signal, and the third signal.

9. The apparatus of claim 8, wherein generation of the conclusion comprises computing a polynomial based on the generated fit curve and the fourth signal.

10. The apparatus of claim 9, wherein the fit curve comprises a parabola.

11. The apparatus of claim 1, wherein the sensor is a Hall-effect sensor, and wherein the first signal, the second signal, the third signal, and the fourth signal correspond to voltages detected by the Hall-effect sensor.

12. An apparatus for controlling an end effector comprising a clamp arm and an ultrasonic blade, the apparatus comprising:
    a sensor configured to generate signals in response to movement of a first tube relative to a second tube, the first tube driving movement of the clamp arm of the end effector; and
    a control circuit configured to:
        receive a first signal, a second signal, and a third signal from the sensor, wherein the first signal, the second signal, and the third signal are associated with positions of the clamp arm of the end effector as it moves;
        generate a fit curve based on the first signal, the second signal, and the third signal;
        receive a fourth signal from the sensor, wherein the fourth signal is associated with a current position of the clamp arm of the end effector as it moves;
        generate a conclusion associated with a relative position of the clamp arm based on the fourth signal and the generated fit curve;
        determine an impedance of the ultrasonic blade in contact with tissue; and
        determine a type of the tissue based on the impedance.

13. The apparatus of claim 12, wherein the generated conclusion comprises an estimated gap between the clamp arm and the ultrasonic blade.

14. The apparatus of claim 12, further comprising a transducer configured to dynamically adjust a power output to the ultrasonic blade of the end effector during an ultrasonic treatment to adjust a tissue cut based on the estimated gap and the type of the tissue.

15. The apparatus of claim 12, wherein the first signal is associated with an open position of the clamp arm relative to the ultrasonic blade, wherein the second signal is associated with an intermediate position of the clamp arm relative to the ultrasonic blade, and wherein the third signal is associated with a closed position of the clamp arm relative to the ultrasonic blade.

16. The apparatus of claim 12, wherein the control circuit is further configured to calibrate signals generated by the sensor during movement of the clamp arm of the end effector based on the generated fit curve to confirm that the sensor is generating accurate signals.

17. The apparatus of claim 16, wherein the calibration comprises a comparison of the fourth signal to the generated fit curve.

18. The apparatus of claim 12, wherein generation of the fit curve comprises computing a polynomial based on the first signal, the second signal, and the third signal.

19. The apparatus of claim 12, wherein generation of the conclusion comprises computing a polynomial based on the generated fit curve and the fourth signal.

20. The apparatus of claim 12, wherein the fit curve comprises a parabola.

21. A computer-implemented method of controlling an end effector comprising a clamp arm and an ultrasonic blade, the method comprising:
- receiving, via a control circuit, a first signal, a second signal, and a third signal from a sensor configured to generate signals in response to movement of a first tube of the end effector relative to a second tube of the end effector, the first tube driving movement of the clamp arm of the end effector, wherein the first signal, the second signal, and the third signal are associated with positions of the clamp arm of the end effector as it moves;
- generating, via the control circuit, a fit curve based on the first signal, the second signal, and the third signal;
- receiving, via the control circuit, a fourth signal from the sensor, wherein the fourth signal is associated with a current position of the clamp arm of the end effector as it moves;
- generating, via the control circuit, a conclusion associated with a relative position of the clamp arm based on the fourth signal and the generated fit curve;
- determining, via the control circuit, a thickness of a tissue based on the generated conclusion;
- determining, via the control circuit, an impedance of the ultrasonic blade in contact with the tissue; and
- determining, via the control circuit, a type of the tissue based on the impedance.

* * * * *